(12) United States Patent
Paul et al.

(10) Patent No.: US 6,855,804 B2
(45) Date of Patent: Feb. 15, 2005

(54) COVALENTLY REACTIVE TRANSITION STATE ANALOGS AND METHODS OF USE THEREOF

(75) Inventors: Sudhir Paul, Missouri City, TX (US); Yasuhiro Nishiyama, Houston, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 0 days.

(21) Appl. No.: 10/114,716

(22) Filed: Apr. 1, 2002

(65) Prior Publication Data

US 2003/0078203 A1 Apr. 24, 2003

Related U.S. Application Data

(60) Continuation of application No. 09/862,849, filed on May 22, 2001, which is a division of application No. 09/046,373, filed on Mar. 23, 1998, now Pat. No. 6,235,714.
(60) Provisional application No. 60/280,624, filed on Mar. 31, 2001.

(51) Int. Cl.[7] ............................................. C07K 14/00
(52) U.S. Cl. ..................... 530/324; 530/350; 435/188.5
(58) Field of Search ................................. 530/350, 322, 530/324; 435/188.5

(56) References Cited

U.S. PATENT DOCUMENTS 5,420,328 A * 5/1995 Campbell .................... 558/110
5,952,462 A * 9/1999 Powell et al. ................ 530/317

FOREIGN PATENT DOCUMENTS

WO     WO 95/29691     * 11/1995

OTHER PUBLICATIONS

Paul, S., et al. (2003) J. Biol. Chem. 278(22), 20429–20435.*
Hanson, J.E., et al. (1989) Biochem. 28, 6294–6305.*
Hirschmann, R., et al. (1994) Science 265, 234–237.*
Takahashi, N. et al. "Improved Generation of Catalytic Antibodies by MRL/MPJ–Ipr/Ipr Autoimmune Mice"; Journal of Immunological Methods; 235;(2000) 113–120.
Wirsching, P., et al. "Reactive Immunization Science"; 270 Dec. 15, 1995 1775–1782.
Mei, S. et al. "Vasoactive Intestinal Peptide Hydrolysis by Antibody Light Chains" The Journal of Biological Chemistry; 226; 24, Aug. 25, 1991; 15571–15574.

* cited by examiner

Primary Examiner—Charles L. Patterson, Jr.
(74) Attorney, Agent, or Firm—Dann, Dorfman, Herrell and Skillman

(57) ABSTRACT

Improved methods for the production, selection and inhibition of catalytic antibodies are disclosed.

10 Claims, 21 Drawing Sheets

Figure 1:
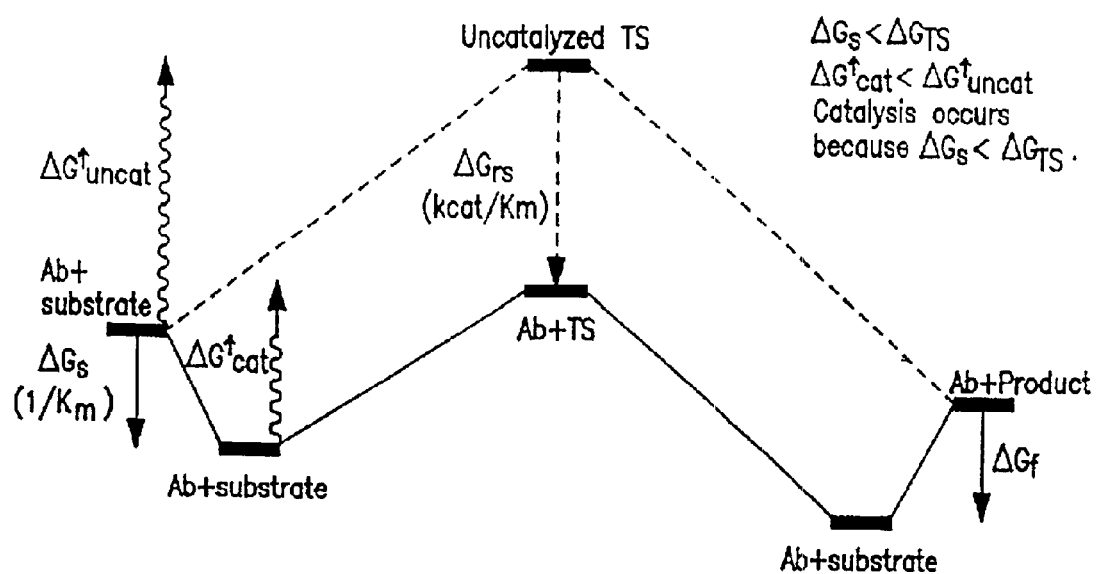

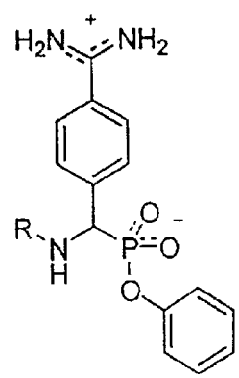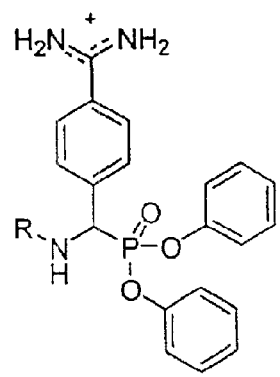
2, R=R₁
3, R=R₂
4, R=R₃
1, R=R₁
5, R=R₂
R₁ 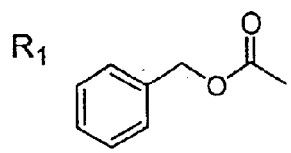
R₂ 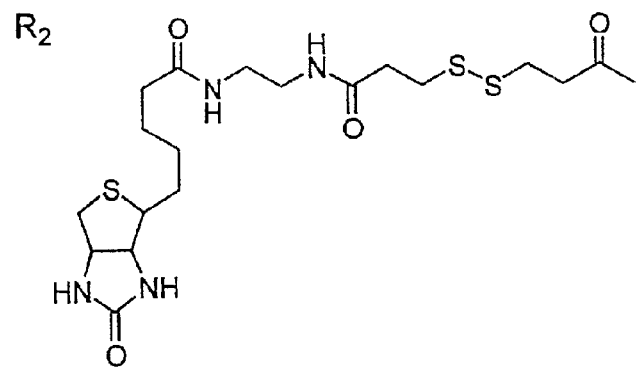
R₃ 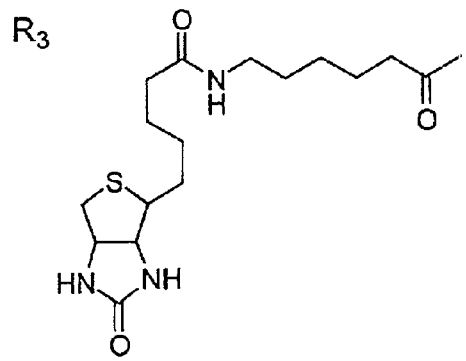
Figure 2

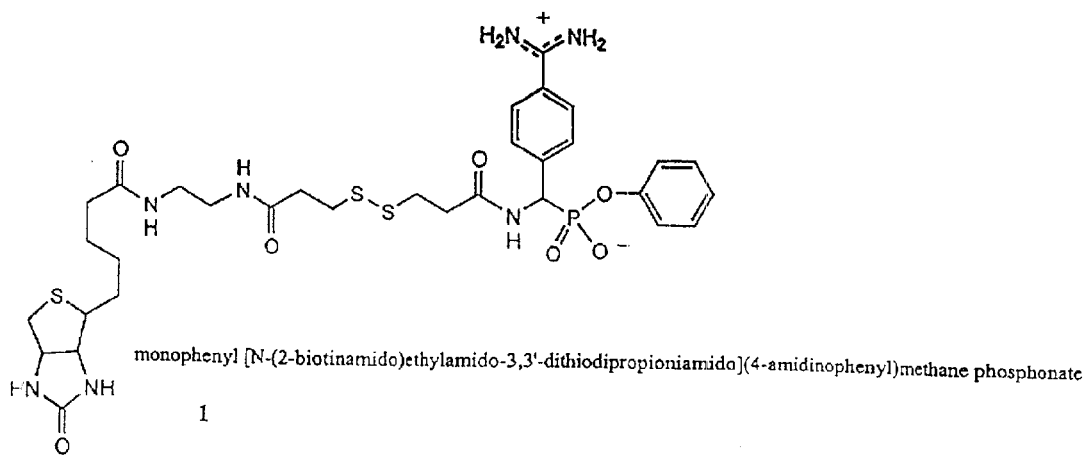

monophenyl [N-(2-biotinamido)ethylamido-3,3'-dithiodipropioniamido](4-amidinophenyl)methane phosphonate
1

Structure of CRTAs

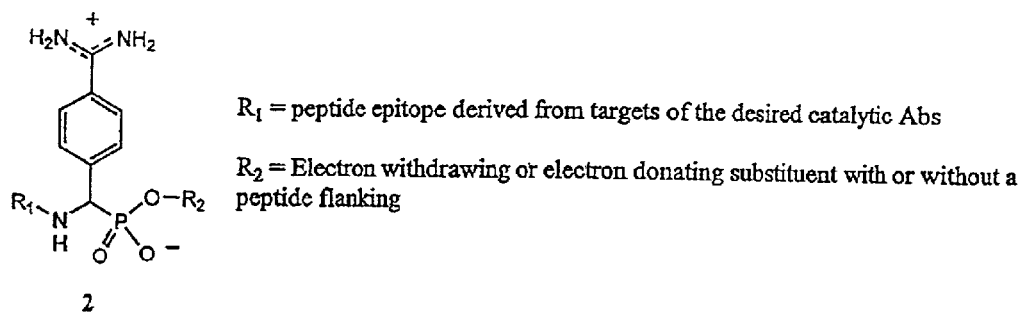

$R_1$ = peptide epitope derived from targets of the desired catalytic Abs $R_2$ = Electron withdrawing or electron donating substituent with or without a peptide flanking

2

Examples of $R_2$ to increase the covalent reactivity of CRTAs

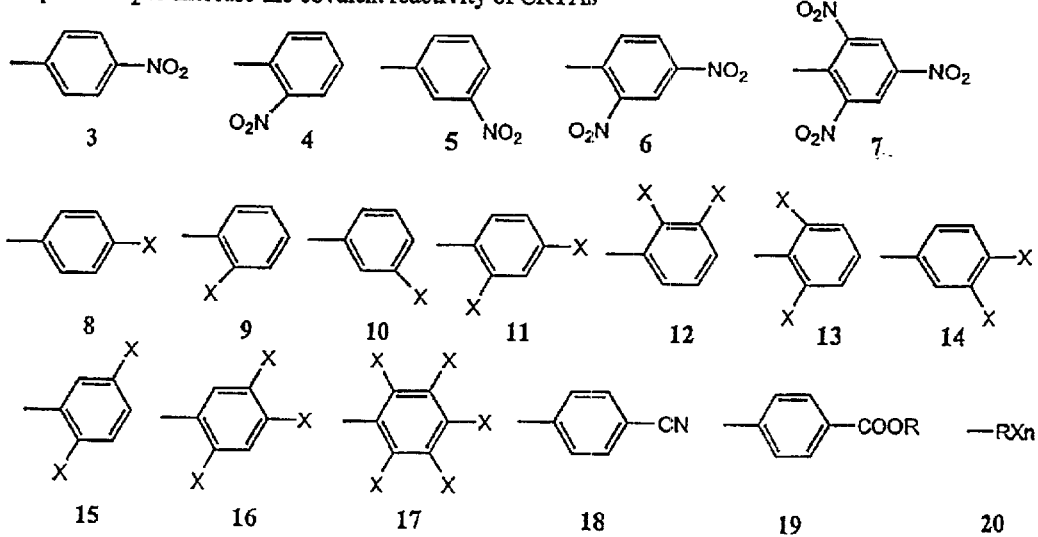

X=halogens
R=H, alkyl or aryl

Figure 16

Examples of R₂ to decrease the covalent reactivity
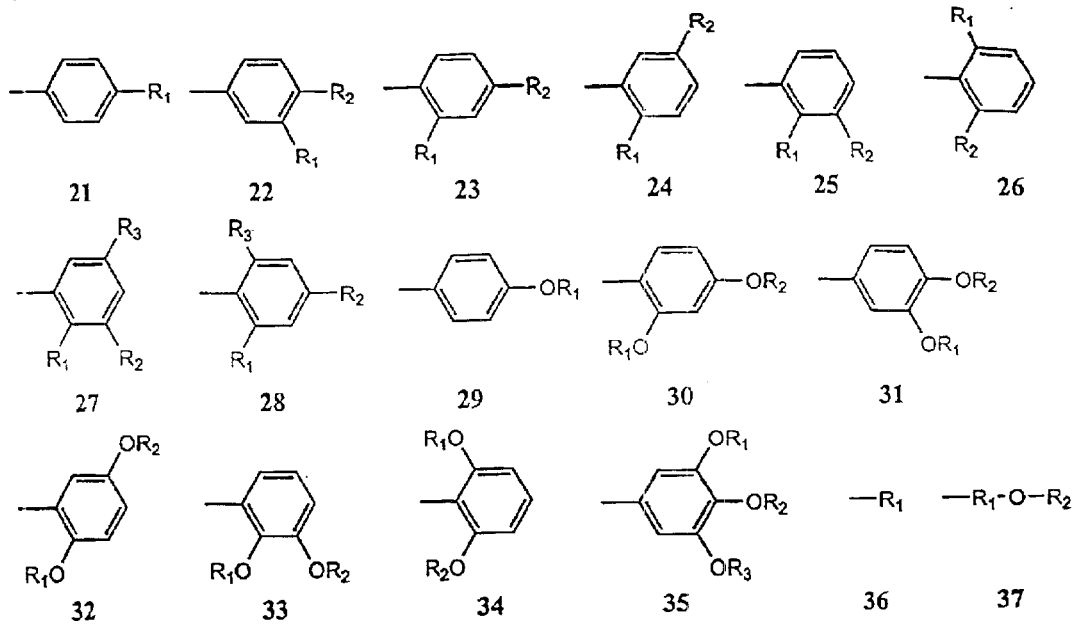
$R_n$ = H, alkyl or aryl
Examples of R₂ with peptide extention
A. Electron withdrawing substituents with peptide extension
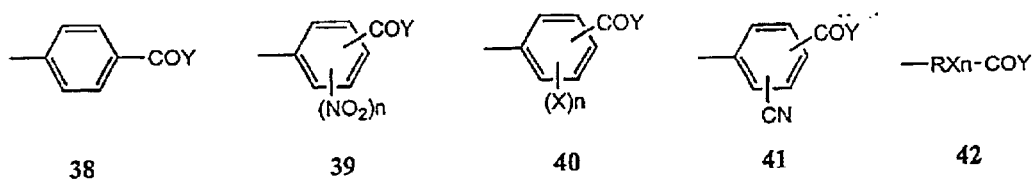
X: halogen
Y: peptide
R: alkyl or aryl
B. Electron withdrawing substituents with peptide extension
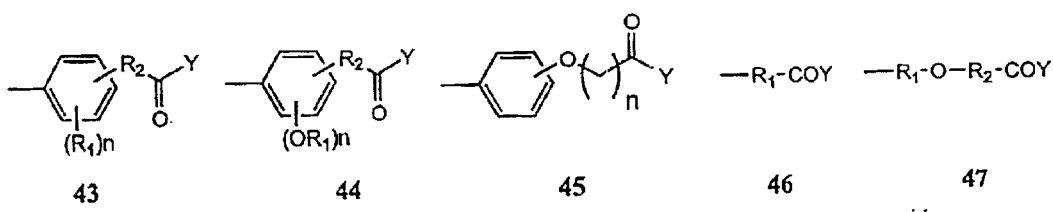
Y: peptide
R: alkyl or aryl
Figure 17

| Target Antigen | Disease Indications |
| --- | --- |
| CD4 | Rheumatoid Arthritis, Asthma, Transplantation, Autoimmune Disease |
| HER2 | Carcinoma |
| EGFR | Carcinoma |
| Macrophage Inhibitory Factor | Inflammatory and Autoimmune Disease |
| CD80 (B7-1) | Inflammatory and Autoimmune Disease, Atherosclerosis |
| CD86 (B7-2) | Inflammatory and Autoimmune Disease, Atherosclerosis |
| CD28 | Inflammatory and Autoimmune Disease, Atherosclerosis |
| CD70 | Inflammatory and Autoimmune Disease, Atherosclerosis |
| CD11b/CD18 | Arthritis, Inflammatory and Autoimmune Disease |
| CD23 | Arthritis, Inflammatory and Autoimmune Disease |
| ICAM-1 | Inflammatory and Autoimmune Disease, Rheumatoid Arthritis, Inflammatory Bowel Disease, Organ Transplant Rejection, Psoriasis, Atherosclerosis |
| VLA-4 Intgrin Receptor | Inflammatory and Autoimmune Disease |
| TNF-alpha | Rheumatoid Arthritis, Autoimmune Disease, Neurotropic Pain, Ischemia-reperfusion Injury, Septic Shock, SIRS, ARDS, Multiple Sclerosis, AIDS |
| Complement Component C5 | Autoimmune Disease, Immunosuppression |

FIG. 19A

| Target Antigen | Disease Indications |
|---|---|
| IL-1 beta Receptor | Rheumatoid Arthritis, Autoimmune Disease, Neurotropic Pain, Ischemia-reperfusion Injury, Septic Shock, SIRS, ARDS |
| IL-1 beta | Rheumatoid Arthritis, Autoimmune Disease, Neurotropic Pain, Ischemia-reperfusion Injury, Septic Shock, SIRS, ARDS |
| GPIIb/IIIa Receptor | Anti-thrombotic, Use in combination with Angioplasty, Percutaneous Coronary Intervention, Unstable Angina, Stroke |
| Clotting Factor VII | Anti-coagulant |
| Plasminogen Activator Inhibitor (PAI-1) | Thrombolytic |
| IL-4 | Asthma |
| IL-4 Receptor | Asthma |
| IL-5 | Allergy |
| IL-5 Receptor | Allergy |
| IgE | Allergic Asthma and Allergic Rhinitis |
| Eotaxin | Allergic Inflammatory Disease, Allergic Asthma |
| Eotaxin Receptor | Allergic Inflammatory Disease, Allergic Asthma |
| PDGF | Vascular Disease, Restinosis |
| PDGF beta Receptor | Vascular Disease, Restenosis |
| alpha.v.beta.3 Integrin | Inhibit Pathologic Bone Resorption |

FIG. 19B

R₁ = Peptide epitope derived from targets of the desired catalytic Abs

R₂ = Electron withdrawing or electron donating substituent with or without a peptide flanking R₃ = Electron withdrawing or electron donating substituent

SEQUENCE LISTING

<160> NUMBER OF SEQ ID NOS: 57

<210> SEQ ID NO 1
<211> LENGTH: 16
<212> TYPE: PRT
<213> ORGANISM: Human Immunodeficiency Virus-1

<400> SEQUENCE: 1

Lys Gln Ile Ile Asn Met Trp Gln Glu Val Gly Lys Ala Met Tyr Ala
1               5                   10                  15

<210> SEQ ID NO 2
<211> LENGTH: 15
<212> TYPE: PRT
<213> ORGANISM: Clostridium tetani

<400> SEQUENCE: 2

Gln Tyr Ile Lys Ala Asn Ser Lys Phe Ile Gly Ile Thr Glu Leu
1               5                   10                  15

<210> SEQ ID NO 3
<211> LENGTH: 28
<212> TYPE: PRT
<213> ORGANISM: Vasoactive intestinal peptide

<400> SEQUENCE: 3

His Ser Asp Ala Val Phe Thr Asp Asn Tyr Thr Arg Leu Arg Lys Gln
 1               5                  10                  15

Met Ala Val Lys Lys Tyr Leu Asn Ser Ile Leu Asn
            20                  25

<210> SEQ ID NO 4
<211> LENGTH: 56
<212> TYPE: DNA
<213> ORGANISM: Homo sapiens

<400> SEQUENCE: 4
gtcctcgcaa ctgcggccca gccggccatg gccgacatcc agatgaccca gtctcc       56

<210> SEQ ID NO 5
<211> LENGTH: 56
<212> TYPE: DNA
<213> ORGANISM: Homo sapiens

<400> SEQUENCE: 5
gtcctcgcaa ctgcggccca gccggccatg gccgatgttg tgatgactca gtctcc       56

<210> SEQ ID NO 6
<211> LENGTH: 56
<212> TYPE: DNA
<213> ORGANISM: Homo sapiens

<400> SEQUENCE: 6
gtcctcgcaa ctgcggccca gccggccatg gccgaaattg tgttgacgca gtctcc       56

<210> SEQ ID NO 7
<211> LENGTH: 56
<212> TYPE: DNA
<213> ORGANISM: Homo sapiens

<400> SEQUENCE: 7
gtcctcgcaa ctgcggccca gccggccatg gccgacatcg tgatgaccca gtctcc       56

<210> SEQ ID NO 8
<211> LENGTH: 56
<212> TYPE: DNA
<213> ORGANISM: Homo sapiens

<400> SEQUENCE: 8
gtcctcgcaa ctgcggccca gccggccatg gccgaaacga cactcacgca gtctcc       56

<210> SEQ ID NO 9
<211> LENGTH: 56
<212> TYPE: DNA
<213> ORGANISM: Homo sapiens

<400> SEQUENCE: 9
gtcctcgcaa ctgcggccca gccggccatg gccgaaattg tgctgactca gtctcc       56

<210> SEQ ID NO 10
<211> LENGTH: 39
<212> TYPE: DNA
<213> ORGANISM: Homo sapiens

<400> SEQUENCE: 10
ccatcctgcg gccgcacact ctcccctgtt gaagctctt       39

<210> SEQ ID NO 11
<211> LENGTH: 48
<212> TYPE: DNA
<213> ORGANISM: Homo sapiens

<400> SEQUENCE: 11
gcctgaaccg cctccaccac tcgagcgttt gatttccacc ttggtccc         48

<210> SEQ ID NO 12
<211> LENGTH: 48
<212> TYPE: DNA
<213> ORGANISM: Homo sapiens

<400> SEQUENCE: 12
gcctgaaccg cctccaccac tcgagcgttt gatctccagc ttggtccc         48

<210> SEQ ID NO 13
<211> LENGTH: 48
<212> TYPE: DNA
<213> ORGANISM: Homo sapiens

<400> SEQUENCE: 13
gcctgaaccg cctccaccac tcgagcgttt gatatccact ttggtccc         48

<210> SEQ ID NO 14
<211> LENGTH: 48
<212> TYPE: DNA
<213> ORGANISM: Homo sapiens

<400> SEQUENCE: 14
gcctgaaccg cctccaccac tcgagcgttt gatctccacc ttggtccc         48

<210> SEQ ID NO 15
<211> LENGTH: 48
<212> TYPE: DNA
<213> ORGANISM: Homo sapiens

<400> SEQUENCE: 15
gcctgaaccg cctccaccac tcgagcgttt aatctccagt cgtgtccc         48

<210> SEQ ID NO 16
<211> LENGTH: 56
<212> TYPE: DNA
<213> ORGANISM: Homo sapiens

<400> SEQUENCE: 16
gtcctcgcaa ctgcggccca gccggccatg gcccagtctg tgttgacgca gccgcc   56

<210> SEQ ID NO 17
<211> LENGTH: 56
<212> TYPE: DNA
<213> ORGANISM: Homo sapiens

<400> SEQUENCE: 17
gtcctcgcaa ctgcggccca gccggccatg gcccagtctg ccctgactca gcctgc   56

<210> SEQ ID NO 18
<211> LENGTH: 56
<212> TYPE: DNA
<213> ORGANISM: Homo sapiens

<400> SEQUENCE: 18
gtcctcgcaa ctgcggccca gccggccatg gcctcctatg tgctgactca gccacc   56

```
<210> SEQ ID NO 19
<211> LENGTH: 56
<212> TYPE: DNA
<213> ORGANISM: Homo sapiens

<400> SEQUENCE: 19
gtcctcgcaa ctgcggccca gccggccatg gcctcttctg agctgactca ggaccc       56

<210> SEQ ID NO 20
<211> LENGTH: 56
<212> TYPE: DNA
<213> ORGANISM: Homo sapiens

<400> SEQUENCE: 20
gtcctcgcaa ctgcggccca gccggccatg gcccacgtta tactgactca accgcc       56

<210> SEQ ID NO 21
<211> LENGTH: 56
<212> TYPE: DNA
<213> ORGANISM: Homo sapiens

<400> SEQUENCE: 21
gtcctcgcaa ctgcggccca gccggccatg gcccaggctg tgctcactca gccgtc       56

<210> SEQ ID NO 22
<211> LENGTH: 56
<212> TYPE: DNA
<213> ORGANISM: Homo sapiens

<400> SEQUENCE: 22
gtcctcgcaa ctgcggccca gccggccatg gccaatttta tgctgactca gcccca       56

<210> SEQ ID NO 23
<211> LENGTH: 48
<212> TYPE: DNA
<213> ORGANISM: Homo sapiens

<400> SEQUENCE: 23
gcctgaaccg cctccaccac tcgagcctag gacggtgacc ttggtccc               48

<210> SEQ ID NO 24
<211> LENGTH: 48
<212> TYPE: DNA
<213> ORGANISM: Homo sapiens

<400> SEQUENCE: 24
gcctgaaccg cctccaccac tcgagcctag gacggtcagc ttggtccc               48

<210> SEQ ID NO 25
<211> LENGTH: 48
<212> TYPE: DNA
<213> ORGANISM: Homo sapiens

<400> SEQUENCE: 25
gcctgaaccg cctccaccac tcgagcctaa aacggtgagc tgggtccc               48

<210> SEQ ID NO 26
<211> LENGTH: 27
<212> TYPE: DNA
<213> ORGANISM: Homo sapiens

<400> SEQUENCE: 26
tgaagattct gtaggggcca ctgtctt                                      27
```

<210> SEQ ID NO 27
<211> LENGTH: 41
<212> TYPE: DNA
<213> ORGANISM: Homo sapiens

<400> SEQUENCE: 27
catgaccaca gtgcacttca ggtgcagctg gtgcagtctg g         41

<210> SEQ ID NO 28
<211> LENGTH: 41
<212> TYPE: DNA
<213> ORGANISM: Homo sapiens

<400> SEQUENCE: 28
catgaccaca gtgcacttca ggtcaactta agggagtctg g         41

<210> SEQ ID NO 29
<211> LENGTH: 41
<212> TYPE: DNA
<213> ORGANISM: Homo sapiens

<400> SEQUENCE: 29
catgaccaca gtgcacttga ggtgcagctg gtggagtctg g         41

<210> SEQ ID NO 30
<211> LENGTH: 41
<212> TYPE: DNA
<213> ORGANISM: Homo sapiens

<400> SEQUENCE: 30
catgaccaca gtgcacttca ggtgcagctg caggagtcgg g         41

<210> SEQ ID NO 31
<211> LENGTH: 41
<212> TYPE: DNA
<213> ORGANISM: Homo sapiens

<400> SEQUENCE: 31
catgaccaca gtgcacttca ggtgcagctg ttgcagtctg c         41

<210> SEQ ID NO 32
<211> LENGTH: 41
<212> TYPE: DNA
<213> ORGANISM: Homo sapiens

<400> SEQUENCE: 32
catgaccaca gtgcacttca ggtacagctg cagcagtcag g         41

<210> SEQ ID NO 33
<211> LENGTH: 42
<212> TYPE: DNA
<213> ORGANISM: Homo sapiens

<400> SEQUENCE: 33
gagtcattct gcggccgcgg ggaagacsga tgggcccttg gt         42

<210> SEQ ID NO 34
<211> LENGTH: 42
<212> TYPE: DNA
<213> ORGANISM: Homo sapiens

<400> SEQUENCE: 34

```
<210> SEQ ID NO 35
<211> LENGTH: 57
<212> TYPE: DNA
<213> ORGANISM: Mus musculus

<400> SEQUENCE: 35
gtcctcgcaa ctgcggccca gccggccatg gccgatgttt tgatgaccca aactcca    57

<210> SEQ ID NO 36
<211> LENGTH: 57
<212> TYPE: DNA
<213> ORGANISM: Mus musculus

<400> SEQUENCE: 36
gtcctcgcaa ctgcggccca gccggccatg gccgatattg tgataaccca ggatgaa    57

<210> SEQ ID NO 37
<211> LENGTH: 57
<212> TYPE: DNA
<213> ORGANISM: Mus musculus

<400> SEQUENCE: 37
gtcctcgcaa ctgcggccca gccggccatg gccgacattg tgctraccca gtctcca    57

<210> SEQ ID NO 38
<211> LENGTH: 57
<212> TYPE: DNA
<213> ORGANISM: Mus musculus
<220> FEATURE:
<221> NAME/KEY: misc_feature
<222> LOCATION: (0)...(0)
<223> OTHER INFORMATION: N = A, T, C, or G

<400> SEQUENCE: 38
gtcctcgcaa ctgcggccca gccggccatg gccgacatcc agatgacnca gtctcca    57

<210> SEQ ID NO 39
<211> LENGTH: 57
<212> TYPE: DNA
<213> ORGANISM: Mus musculus

<400> SEQUENCE: 39
gtcctcgcaa ctgcggccca gccggccatg gcccaaattg ttctcaccca gtctcca    57

<210> SEQ ID NO 40
<211> LENGTH: 57
<212> TYPE: DNA
<213> ORGANISM: Mus musculus

<400> SEQUENCE: 40
gtcctcgcaa ctgcggccca gccggccatg gccgaaaatg tgctcaccca gtctcca    57

<210> SEQ ID NO 41
<211> LENGTH: 42
<212> TYPE: DNA
<213> ORGANISM: Mus musculus

<400> SEQUENCE: 41
gagtcattct gcggccgcct cattcctgtt gaagctcttg ac    42

<210> SEQ ID NO 42
<211> LENGTH: 110
```
gagtcattct gcggccgcgg ggaaaagggt tggggcggat gc    42

<212> TYPE: PRT
<213> ORGANISM: Mus musculus domesticus

<400> SEQUENCE: 42

Asp Val Leu Met Thr Gln Ser Pro Leu Ser Leu Pro Val Ser Leu Gly
 1               5                  10                  15

Asp Gln Ala Ser Ile Ser Cys Arg Ser Ser Gln Ser Ile Val His Ser
            20                  25                  30

Asn Gly Asn Thr Tyr Leu Glu Trp Tyr Leu Gln Lys Pro Gly Gln Ser
        35                  40                  45

Pro Lys Leu Leu Ile Tyr Lys Val Ser Asn Arg Phe Ser Gly Val Pro
50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

Ser His Val Pro Tyr Thr Phe Gly Gly Gly Thr Gly Lys
            100                 105                 110

<210> SEQ ID NO 43
<211> LENGTH: 330
<212> TYPE: DNA
<213> ORGANISM: Mus musculus domesticus

<400> SEQUENCE: 43
gatgttttga tgacccaatc tccactctcc ctgcctgtca gtcttggaga tcaagcctcc      60
atctcttgca gatctagtca gagcattgta catagtaatg gaaacaccta tttagaatgg     120
tacctgcaga aaccaggcca gtctccaaag ctcctgatct acaaagtttc caaccgattt     180
tctggggtcc cagacaggtt cagtggcagt ggatcaggga cagatttcac actcaagatc     240
agcagagtgg aggctgagga tctgggagtt tattactgct ttcaaggttc acatgttccg     300
tacacgttcg gagggggcca aactggaaaa                                       330

<210> SEQ ID NO 44
<211> LENGTH: 102
<212> TYPE: PRT
<213> ORGANISM: Mus musculus domesticus

<400> SEQUENCE: 44

Gln Asn Val Leu Thr Gln Ser Pro Ala Leu Met Ser Ala Ser Pro Gly
 1               5                  10                  15

Glu Lys Val Thr Ile Thr Cys Ser Ala Ser Pro Ser Val Ser Tyr Met
            20                  25                  30

His Trp Phe Gln Gln Lys Pro Gly Thr Ser Pro Lys Leu Trp Ile Tyr
        35                  40                  45

Ser Thr Ser Asn Leu Ala Ser Gly Val Pro Ala Arg Phe Ser Gly Ser
50                  55                  60

Gly Ser Gly Thr Ser Tyr Ser Leu Thr Ile Ser Arg Met Glu Ala Glu
65                  70                  75                  80

Asp Ala Ala Thr Tyr Tyr Cys Gln Gln Arg Ser Ser Tyr Pro Trp Thr
                85                  90                  95

Phe Gly Gly Ala Pro Ser
            100

<210> SEQ ID NO 45
<211> LENGTH: 307
<212> TYPE: DNA

<213> ORGANISM: Mus musculus domesticus

<400> SEQUENCE: 45

```
caaaatgttc tcacccagtc tccagcactc atgtctgcat ctccagggga gaaggtcacc    60
ataacctgca gtgccagccc aagtgtaagt tacatgcact ggttccagca gaagccaggc   120
acttctccca aactctggat ttatagcaca tccaacctgg cttctggagt ccctgctcgc   180
ttcagtggca gtggatctgg gacctcttac tctctcacaa tcagccgaat ggaggctgaa   240
gatgctgcca cttattactg ccagcaaagg agtagttacc cgtggacgtt cggtggagca   300
ccaagct                                                              307
```

<210> SEQ ID NO 46
<211> LENGTH: 264
<212> TYPE: PRT
<213> ORGANISM: Artificial Sequence
<220> FEATURE:
<223> OTHER INFORMATION: Synthetic construct

<400> SEQUENCE: 46

```
Gln Val Lys Leu Gln Gln Ser Gly Pro Glu Leu Val Lys Pro Gly Ala
  1               5                  10                  15
Ser Val Lys Ile Ser Cys Lys Ala Ser Gly Tyr Thr Phe Thr Asp Tyr
                 20                  25                  30
Thr Met Asp Trp Val Lys Gln Ser His Gly Lys Ser Leu Glu Trp Ile
             35                  40                  45
Gly Tyr Ile Tyr Pro Asn Asn Gly Gly Thr Gly Tyr Asn Gln Lys Phe
         50                  55                  60
Lys Ser Lys Ala Thr Leu Thr Val Asp Lys Ser Ser Ser Thr Ala Tyr
 65                  70                  75                  80
Met Glu Leu His Ser Leu Thr Ser Glu Asp Ser Ala Val Tyr Tyr Cys
                 85                  90                  95
Ala Arg Phe Ser Ser Phe Asp Tyr Trp Gly Gln Gly Thr Thr Val Thr
                100                 105                 110
Val Ser Ser Gly Gly Gly Gly Ser Gly Gly Val Gly Ser Gly Gly Gly
            115                 120                 125
Gly Ser Asp Ile Gln Met Thr Gln Ser Pro Ser Ser Leu Ser Ala Ser
        130                 135                 140
Leu Gly Asp Thr Ile Thr Ile Thr Cys His Ala Ser Gln Asn Ile Asn
145                 150                 155                 160
Val Trp Leu Ser Trp Tyr Gln Gln Lys Pro Gly Asn Ile Pro Lys Leu
                165                 170                 175
Leu Ile Tyr Arg Ala Ser Asn Leu His Thr Gly Val Pro Ser Arg Phe
            180                 185                 190
Ser Gly Ser Gly Ser Gly Thr Gly Phe Thr Leu Thr Ile Ser Ser Leu
        195                 200                 205
Gln Pro Glu Asp Ile Ala Thr Tyr Tyr Cys Gln Gln Gly Gln Ser Tyr
    210                 215                 220
Pro Leu Thr Phe Gly Thr Gly Thr Lys Leu Glu Ile Lys Arg Ala Ala
225                 230                 235                 240
Ala His His His His His Gly Ala Ala Glu Gln Lys Leu Ile Ser
                245                 250                 255
Glu Glu Asp Leu Asn Gly Ala Ala
            260
```

<210> SEQ ID NO 47

```
<211> LENGTH: 795
<212> TYPE: DNA
<213> ORGANISM: Artificial Sequence
<220> FEATURE:
<223> OTHER INFORMATION: Synthetic construct

<400> SEQUENCE: 47
caggtgaaac tgcagcagtc aggacctgaa ctggtgaagc ctggggcttc agtgaagata      60
tcctgcaagg cttctggtta cacattcact gactacacca tggactgggt gaagcagagc     120
catggaaaga gccttgagtg gattggatat atttatccta caatggtgg tactggctac      180 aaccagaagt tcaagagcaa ggccacattg actgtagaca gtcctccag cacagcctac      240 atggagctcc acagcctgac atctgaggac tctgcagtct attactgtgc aagattttcc     300
tcttttgact actggggcca aggaccacg gtcaccgtct cctcaggtgg aggcggttca      360
ggcggagttg gctctggcgg tggcggatcg gacatccaga tgactcagtc tccatccagt    420
ctgtctgcat cccttggaga cacaattacc atcacttgcc atgccagtca gaacattaat    480
gtttggttaa gctggtacca gcagaaacca ggaaatattc ctaaactatt gatctatagg    540
gcttccaact gcacacaggg cgtcccatca aggtttagtg gcagtggatc tggaacaggt    600
ttcacattaa ccatcagcag cctgcagcct gaagacattg ccacttacta ctgtcaacag    660
ggtcaaagtt atcctctcac gttcggcacg ggcaccaagc tggaaatcaa acgggcggcc    720
gcacatcatc atcaccatca cggggccgca gaacaaaaac tcatctcaga agaggatctg    780
aatggggccg catag                                                     795

<210> SEQ ID NO 48
<211> LENGTH: 113
<212> TYPE: PRT
<213> ORGANISM: Homo sapiens

<400> SEQUENCE: 48

Asp Ile Gln Met Thr Gln Ser Pro Ser Thr Leu Ser Ala Ser Val Gly
 1               5                  10                  15

Asp Thr Val Thr Ile Ala Cys Arg Ala Ser Gln Ser Ile Asn Gly Tyr
             20                  25                  30

Leu Ala Trp Tyr Gln Gln Lys Pro Gly Lys Ala Pro Asn Leu Leu Ile
         35                  40                  45

Phe Lys Ala Ser Thr Leu Gln Ser Gly Val Pro Ser Arg Phe Ser Gly
     50                  55                  60

Ser Gly Tyr Ala Arg Glu Phe Thr Leu Thr Ile Ser Ser Leu Gln Pro
65                  70                  75                  80

Asp Asp Phe Ala Thr Tyr Tyr Cys Gln Gln Tyr Tyr Thr His Ser Arg
                 85                  90                  95

Thr Phe Gly Gln Gly Thr Gln Val Glu Ile Thr Arg Thr Val Ala Ala
            100                 105                 110

Pro

<210> SEQ ID NO 49
<211> LENGTH: 339
<212> TYPE: DNA
<213> ORGANISM: Homo sapiens

<400> SEQUENCE: 49
gacatccaga tgacccagtc tccttccacc ctgtctgcat ctgtgggaga cacagtcacc      60
atcgcttgcc gggccagtca gagtattaat ggctacttgg cctggtatca gcagaaacct     120
```

```
gggaaagccc ctaacctcct gatctttaag gcatctactt tacaaagtgg ggtcccatca    180
aggttcagcg gcagtggata tgcgagagaa ttcacgctca ccatcagcag cctgcagcct    240
gatgattttg caacttatta ctgccaacag tattatactc actcccggac gttcggccaa    300
gggacccagg tggaaatcac acgaactgtg gctgcacca                          339
```

<210> SEQ ID NO 50
<211> LENGTH: 9
<212> TYPE: PRT
<213> ORGANISM: Homo sapiens

<400> SEQUENCE: 50

Met Glu Glu Asp Gly Val Arg Lys Cys
 1               5

<210> SEQ ID NO 51
<211> LENGTH: 6
<212> TYPE: PRT
<213> ORGANISM: Homo sapiens

<400> SEQUENCE: 51

Cys Glu Gly Pro Cys Arg
 1               5

<210> SEQ ID NO 52
<211> LENGTH: 11
<212> TYPE: PRT
<213> ORGANISM: Homo sapiens

<400> SEQUENCE: 52

Lys Gln Ile Ile Asn Met Trp Gln Glu Val Gly
 1               5                  10

<210> SEQ ID NO 53
<211> LENGTH: 4
<212> TYPE: PRT
<213> ORGANISM: Homo sapiens

<400> SEQUENCE: 53

Ala Met Tyr Ala
 1

<210> SEQ ID NO 54
<211> LENGTH: 7
<212> TYPE: PRT
<213> ORGANISM: Homo sapiens

<400> SEQUENCE: 54

Leu Ala Asn Gly Val Glu Leu
 1               5

<210> SEQ ID NO 55
<211> LENGTH: 7
<212> TYPE: PRT
<213> ORGANISM: Homo sapiens

<400> SEQUENCE: 55

Asp Asn Gln Leu Val Val Pro
 1               5

<210> SEQ ID NO 56
<211> LENGTH: 7
<212> TYPE: PRT
<213> ORGANISM: Homo sapiens

```
<400> SEQUENCE: 56

Pro Lys Lys Lys Met Glu Lys
1               5

<210> SEQ ID NO 57
<211> LENGTH: 7
<212> TYPE: PRT
<213> ORGANISM: Homo sapiens

<400> SEQUENCE: 57

Phe Val Phe Asn Lys Ile Glu
1               5
```

COVALENTLY REACTIVE TRANSITION STATE ANALOGS AND METHODS OF USE THEREOF

This application is a continuation in part application of U.S. application Ser. No. 09/862,849 filed May 22, 2001, which is divisional application of U.S. application Ser. No. 09/046,373 filed Mar. 23, 1998, now U.S. Pat. No. 6,235,714. This application also claims priority to U.S. Provisional Application 60/280,624 filed Mar. 31, 2001, the entire disclosure of each of the foregoing applications being incorporated by reference herein.

Pursuant to 35 U.S.C. §202(c) it is acknowledged that the U.S. Government has certain rights in the invention described herein, which was made in part with funds from the National Institutes of Health, Grant Numbers: HLA4126, HL59746, AI31268, CA80312, and AI46029.

FIELD OF THE INVENTION

This invention relates to the fields of immunology, molecular biology and medicine. More specifically, the invention provides novel methods and compositions for stimulating the production of novel catalytic antibodies and inhibitors thereof. Also provided are improved methods for screening phage display libraries expressing catalytic antibodies.

BACKGROUND OF THE INVENTION

Several publications and patent documents are referenced in this application in order to more fully describe the state of the art to which this invention pertains. The disclosure of each of these publications is incorporated by reference herein.

The observation that vasoactive intestinal peptide (VIP) is cleaved by antibodies (Abs) from asthma patients provided early evidence that Abs may possess peptidase activity. This observation has been reproduced independently by Suzuki et al. Autoantibody catalysis is not restricted to catalysis of VIP. Autoantibodies in Hashimoto's thyroiditis catalyze the cleavage of thyroglobulin. Further evidence for autoantibody catalysis has been provided by reports of DNase activity in Abs from lupus patients. The bias towards catalytic antibody (Ab) synthesis in autoimmune disease is supported by observations that mouse strains with a genetic predisposition to autoimmune disease produce esterase Abs at higher levels when compared to control mouse strains in response to immunization with a transition state analog.

Like noncatalytic Abs, peptidase Abs are capable of binding antigens (Ags) with high specificity mediated by contacts at residues from the VL and VH domains. The purified H and L subunits are known to be independently capable of binding Ags, albeit with lower affinity than the parent Ab. X-ray crystallography of Ab-Ag complexes have shown that the VL and VH domains are both involved in binding the antigen (Ag). The precise contribution of the two V domains varies in individual Ab-Ag complexes, but the VH domain may contribute at a somewhat greater level, because CDRH3 tends to be longer and more variable in sequence compared to CDRL3.

The initial complexation of a polypeptide Ag by a peptidase Ab is followed by cleavage of one or more peptide bonds. Just prior to cleavage, contacts with the catalytic residues of the antibody are established with the peptide bond in the transition state. See FIG. 1. The ability to hydrolyze peptide bonds appears to reside in the VL domain. This conclusion is based on the cleavage of VIP by polyclonal autoantibody L chains, monoclonal L chains isolated from multiple myeloma patients and their recombinant VL domains, and recombinant L chains raised by immunization with VIP. The H chains of polyclonal and monoclonal Abs to VIP are capable of VIP binding but are devoid of the catalytic activity. The VH domain can nevertheless influence the peptidase activity by "remote control", because in binding to VIP remote from the cleavage site, it can influence the conformation of the binding site as shown by the peptidase activity of F, constructs composed of the catalytic anti-VIP VL domain linked to its VH domain. The anti-VIP VH domain exerted beneficial effects and an irrelevant VH domain exerted detrimental effects on the catalytic activity, as evaluated by the values of VIP binding affinity and catalytic efficiency. The proposed existence of distinct catalytic and antigen binding subsites in catalytic Abs is consistent with data that Abs generally contain large combining sites, capable of accommodating 15–22 amino acids of polypeptide substrates, and that substrate regions distant from the cleavage site are recognized by the Abs. Thus, the VH domain offers a means to control the specificity of the catalytic site.

The present invention provides novel compositions and methods for stimulating production of catalytic antibodies and fragments thereof. Catalytic antibodies with specificity for target antigens provide a valuable therapeutic tool for clinical use. Provided herein are improved methods for identifying, isolating and refining catalytic antibodies for the treatment of a variety of medical diseases and disorders, including but not limited to infectious, autoimmune and neoplastic disease. Such catalytic antibodies will also have applications in the fields of veterinary medicine, industrial and clinical research and dermatology.

SUMMARY OF THE INVENTION

According to one aspect of the invention, methods and compositions are provided herein for stimulating catalytic antibody production to predetermined target antigens, including but not limited to those involved in pathogenic and neoplastic processes. Covalently reactive transition state analogs (CRTSAs) are described which stimulate the production of catalytic antibodies with therapeutic value in the treatment of a variety of medical conditions, including autoimmunity disorders, microbial diseases, lymphoproliferative disorders and cancer. The catalytic antibodies of the invention may also be used prophylatically to prevent certain medical disorders, including but not limited to septic shock, systemic inflammatory disease and acute respiratory distress syndrome.

The covalently reactive transition state analogs, (CRTSAs) of the present invention contain three essential elements and have the following formula: $R_1$-E-$R_2$ wherein $R_1$ is a peptide sequence of an epitope of a target protein antigen, E is an electrophilic covalently reactive center bearing a partial or full negative charge and $R_2$ is an electron withdrawing or electron donating substituent, R2 optionally further comprising a flanking peptide sequence. The CRTSAs of the invention optionally comprise Y which is a basic residue (Arg or Lys or an analog thereof) at the P1 position (first amino acid on the N-terminal side of the reaction center), Y may also comprise an electron withdrawing or electron donating substituent as shown in FIGS. 16 and 17.

In one aspect of the invention, CRTSAs are administered to a living organism under conditions whereby the CRTSAs stimulate production of specific catalytic antibodies. The catalytic antibodies are then purified. Antibodies so purified are then adminstered to a patient in need of such treatment in an amount sufficient to inactivate antigens associated with a predetermined medical disorder.

According to another aspect of the present invention, a method is provided for treating a pathological condition related to the presence of endogenously expressed catalytic antibodies. Examples of such abnormal pathological conditions are certain autoimmune disorders as well as lymphoproliferative disorders. The method comprises administering to a patient having such a pathological condition a pharmaceutical preparation comprising covalently reactive transition state analog capable of irreversibly binding the endogenously produced catalytic antibodies, in an amount sufficient to inhibit the activity of the antibodies, thereby alleviating the pathological condition. In this embodiment, the CRTSA contains a minimal B epitope only to minimize the immunogenicity of the CRTSA.

According to another aspect of this invention, a pharmaceutical preparation is provided for treating a pathological condition related to the presence of endogenously produced catalytic antibodies. This pharmaceutical preparation comprises a CRTSA in a biologically compatible medium. Endogenously produced catalytic antibodies are irreversibly bound and inactivated upon exposure to the CRTSA. The preparation is administered an amount sufficient to inhibit the activity of the catalytic antibodies.

In another aspect of the invention, methods for passively immunizing a patient with a catalytic antibody preparation are provided. Catalytic antibodies are infused into the patient which act to inactivate targeted disease associated antigens.

In an alternative embodiment, should the patient experience unwanted side effects, the activity of the infused catalytic antibodies may be irreversibly inactiviated by administering the immunizing CRTSA to said patient. Again, the immunogenicity of the CRTSA in this embodiment would be reduced via the inclusion of a minimally immunogenic B cell epitope. A T cell universal epitope would be omitted in this CRTSA.

In yet another aspect of the invention, active immunization of patients is achieved by administering the CRTSAs of the invention in a CRTSA-adjuvant complex to a patient to be immunized. At least 2 subsequent booster injections of the CRTSA-adjuvant complex at 4 week intervals will also be adminstered. Following this procedure, the patient sera will be assessed for the presence of prophylactic catalytic antibodies.

A further aspect of the invention comprises methods for screening phage or B cells for expression of catalytic antibodies. In this embodiment, phage or B cells are screened with a CRTSA and those phage or B cell which bind the CRTSA are isolated and characterized further. Methods for isolating and cloning the DNA encoding catalytic antibodies from phage or B cells so isolated are also within the scope of the present invention.

Finally, catalytic sFv and light chains are also with encompassed within the present invention.

The methods and CRTSAs of the present invention provide notable advantages over currently available compounds and methods for stimulating catalytic antibodies specific for predetermined target antigens. Accordingly, the disclosed compounds and methods of the invention provide valuable clinical reagents for the treatment of disease.

BRIEF DESCRIPTION OF THE DRAWINGS

FIG. 1. A free energy diagram for antibody catalysis involving stabilization of the substrate ground state ($\Delta G_s$) and transition state ($\Delta G_{TS}$). $\Delta G^{+}_{uncat}$ and $\Delta G^{+}_{cat}$ correspond to activation energies for the uncatalyzed and catalyzed reactions, respectively. Km is a function of the extent of ground state stabilization ($\Delta G_s$). Kcat/Km is a function of the extent of transition state stabilization relative to the catalyst-substrate ground state complex.

FIG. 2. Compounds 1–5.

FIG. 3. Binding of monoester 3 and diester 5 by trypsin. Streptavidin-peroxidase stained blots of SDS-gels showing trypsin bound to 3 without and with preincubation with DFP (lanes 1 and 2, respectively) and to 5 without and with preincubation with DFP (lanes 3 and 4, respectively). Pretreatment of trypsin (1 μM) with DFP (1 mM) or solvent was for 30 min followed by incubation with 3 (200 M) or 5 (20 M), gel filtration, precipitation of the effluent at the void volume with trichloroacetic acid, dissolution of the pellets in 2% SDS, boiling (5 min) and electrophoresis on SDS-gels.

FIG. 4. Identification of monoester-binding site in trypsin by mass spectrometry. (A) Following treatment of trypsin with 4, the adducts were subjected to tryptic digestion and affinity chromatography on immobilized avidin. The molecular ion at m/z 3738 corresponds to trypsin residues 189–218 derivatized by 4. Also detected were underivatized peptide 189–218 (m/z 3186) and the phosphonic acid derivative from 4 (m/z 569), presumably formed by partial decomposition of the phosphonylated fragment during sample preparation. Signals at m/z 3221 and 2003 are avidin fragments (see text for explanation). (B) Proposed structure of 4-derivatized trypsin fragment. C represents the S-carbamoylmethylated cysteine residue.

FIG. 5. Kinetics of trypsin inactivation by monoester 2 (A) and diester 1(B). Reaction initiated by mixing trypsin [1 mM (2) or 0.1 mM (1)] with varying inhibitor concentrations [2 0.4 (●), 0.6 (■), 0.8 (▲), 1.0 (○), 1.2 (□) mM; 10.5 (●), 1.0 (■), 1.5 (▲), 2.0 (○), 2.5 (□) mM] at 37° C. Aliquots withdrawn at various time points (2, 5–20 min; 1, 0.5–5 min), diluted 500-fold (2) or 50-fold (1), substrate (EAR-MCA, 0.2 mM) added and residual enzyme activity measured fluorometrically. The standard deviation of the residuals (sy.x) for linear regression fits were never more than 0.07 (A) and 0.23 (B).

FIG. 6. Irreversible inhibition of (A) thrombin and (B, C) YZ17 activity by monoester 3. (A)●: Thrombin (4 unit/ml) preincubated with 1000×3 concentrations shown on X-axis (37° C., 30 min) followed by 1000× dilution in buffer containing substrate (VPR-MCA, 25 M) and incubation for 3 h. ○: Thrombin (0.004 unit/ml) incubated with 3 and 25 M substrate without the preincubation step. Data are means of 3 closely agreeing replicates (s.d. <12.7%). Thrombin activity without 3 25.5–27.9 FU/h (3 independent experiments). Background fluorescence 21 FU. (B) YZ17 (20 nM) incubated with 3 and 0.4 mM substrate without the preincubation step. Arrow: final concentration of 3 in panel C. (C) YZ17 (200 nM) preincubated for varying periods (X-axis) with 0.5 mM 3 followed by 100× dilution in solvent containing substrate (EAR-MCA, 0.4 mM) yielding 3 concentration shown by the arrow in panel B. Catalytic activity was measured over 16 h. Data are means of 3 closely agreeing replicates (s.d. <8.3%). YZ17 activity without 3, 16.0–16.9 FU/h. Background fluorescence 19.3 FU.

FIG. 7. Binding of monoester 4 by Fv and L chain clones. Streptavidin-peroxidase stained blots of SDS-gels showing reaction mixtures of monoester 4 (500 μM) treated for 24 h with metal affinity purified recombinant Ab fragments. Clone Fv YZ17 (2 μM) without (lane 1) and with DFP pretreatment (5 mM, lane 2); L chain clone SK-35 (4.4 μM, lane 3); and L chain clone c23.5 (2 gM, lane 4). Lane 5, molecular weight markers. Sample processing for electrophoresis was as in FIG. 3.

Figure 8:
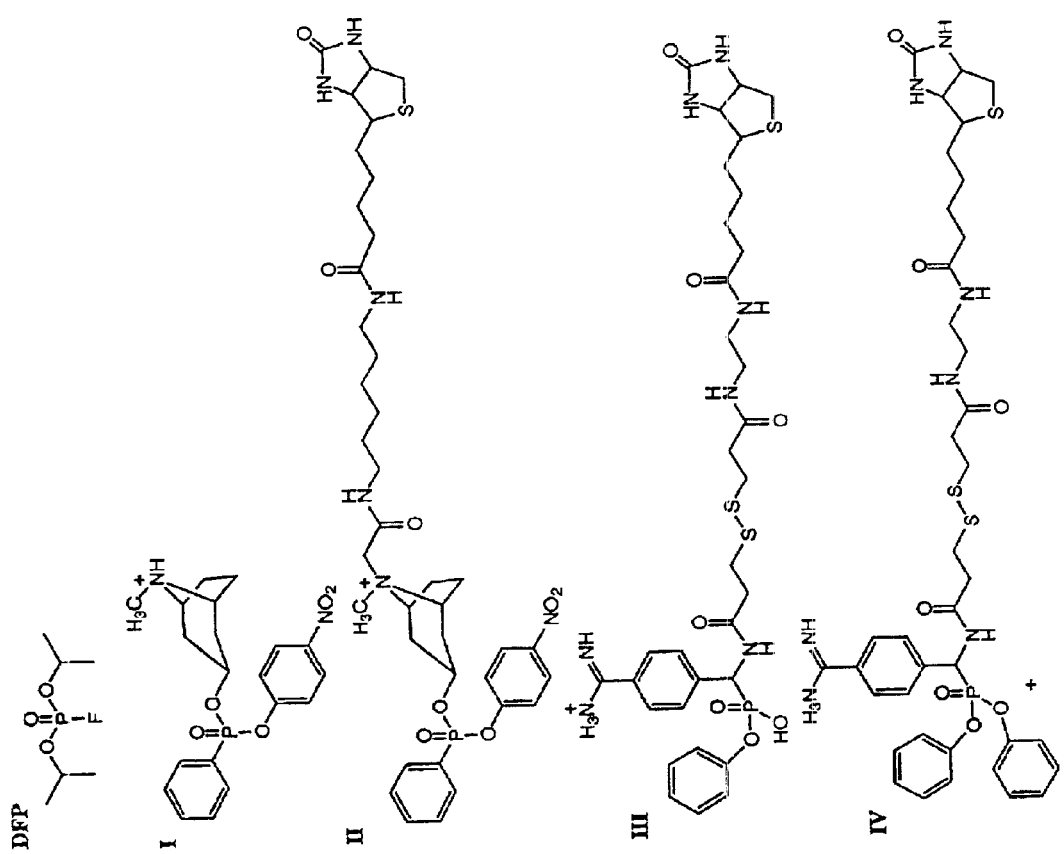

FIG. 8. DFP and phosphonate esters.

Figure 9:
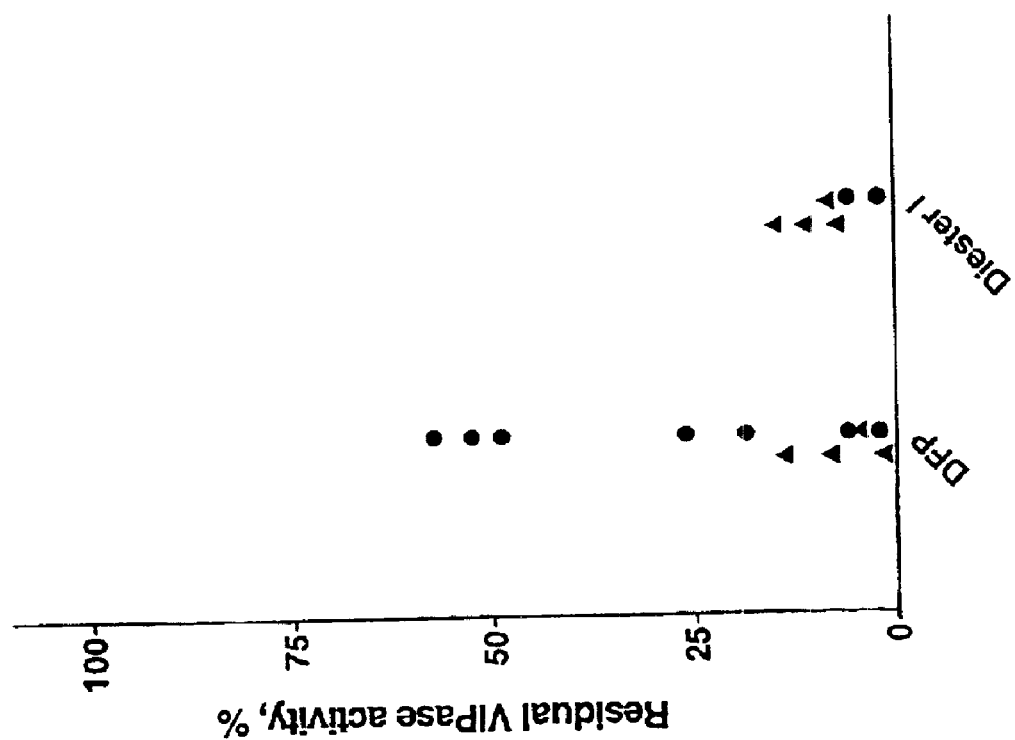

FIG. 9. DFP and diester II inhibition of VIPase antibody fragments. Inhibition of 11 clones by DFP and 6 clones by II was analyzed. (▲) germline L chain c23.5, (♥) somatically mature L clone c23.5, (■) L chain hk14, (♦) Fv mRT3, (●) L chains U2, U19, U15, U7, U30, U4, U16 listed in order of decreasing residual activity in the presence of DFP. L chains U4 and U16 were studied for II inhibition. Substrate about 50 $\mu$M (Tyr $_{10\text{-}125}$ I)VIP (25 K c.p.m.). Inhibitors: DFP 1 mM; II 0.1 mM. Reaction conditions 3 hours, 37° C. Catalyst concentration 2–50 nM [adjusted to give about 40% (Tyr $_{10\text{-}125}$ I)VIP hydrolysis]. Values (means of closely agreeing duplicates) are percent of hydrolysis observed in control assays without inhibitor.

Figure 10:
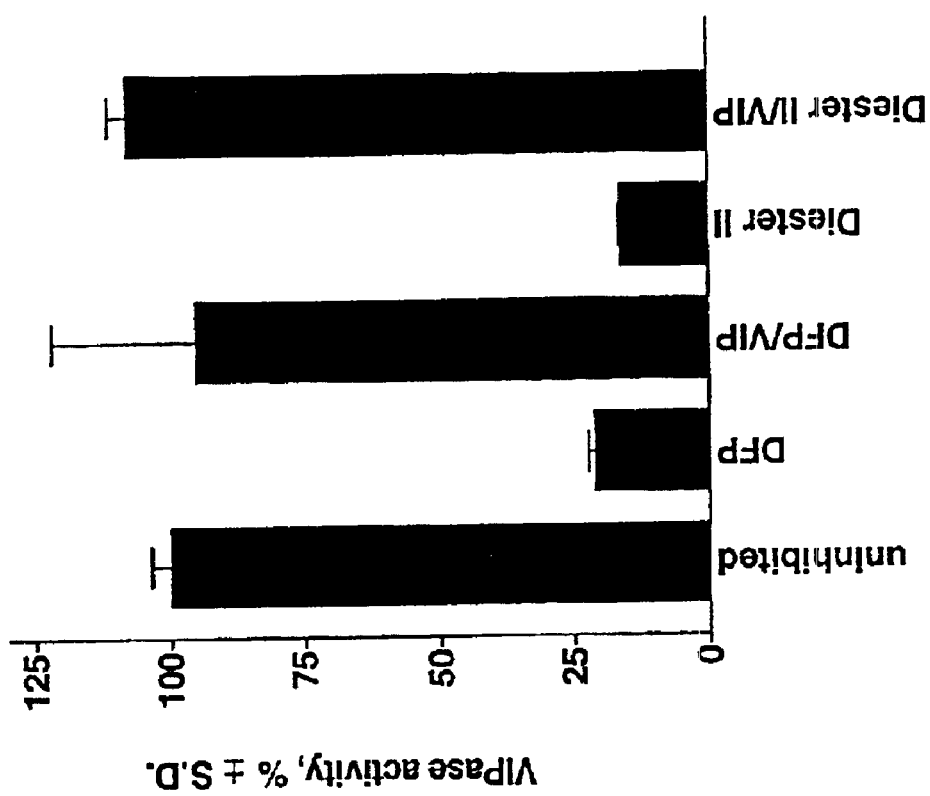

FIG. 10. Irreversible inhibition of peptidase activity by DFP and diester II: effect of substrate. L chain clone U16 (1.3 $\mu$M) was treated the inhibitors (1 mM DFP, 0.1 mM II) or assay diluent in the presence or absence of VIP (1 $\mu$M, 30 min, 37° C.). Excess inhibitor and VIP were removed by gel-filtration and the protein fraction assayed for (Tyr $_{10\text{-}125}$ I)VIP as in FIG. 2 (U16 concentration, 33 nM).

FIG. 11. Diester II binding by proteolytic Ab fragments. (A) Gel filtration of II-Fv mRT3 complexes. Fv (1.3 $\mu$M) was treated with II (100 $\mu$M; 30 min) and the mixture (200 $\mu$l) subjected to chromatography on a Superose-12 column. Aliquots of column fractions (100 $\mu$l) were analyzed in duplicate for II-Fv complexes by ELISA (see Methods). Inset, silver-stained SDS-polyacrylamide gel (8–25%) of fraction 30, corresponding to the Fv peak. (B). Streptavidin-peroxidase stained blots of SDS-polyacrylamide gels showing II-adducts of Fv mRT3 (lane 1), L chain c23.5 (lane 2), L chain hk14 (lane 3) and trypsin (lane 4). Lane 5, 6 and 7 are silver-stained Fv mRT3, L chain c23.5 and L chain hk14. Treatment of Fv mRT3 (0.4 $\mu$M), c23.5 L chain (1.8 $\mu$M), hk14 L chain (0.4 $\mu$M) and trypsin (0.2 $\mu$M) with II (20 $\mu$M) was for 30 min, 37° C. II staining of monomer Ab fragments is evident. Dimeric L chain c23.5 (55 kD) and trypsin breakdown products display low level staining. (C). Streptavidin-peroxidase stained dot blot of L chain c23.5 (1.8 $\mu$M) treated with II (1 $\mu$M, 2 hours, 25° C.) in the absence (dot 1) and presence of 80, 10, 1 and 0.1 $\mu$M VIP (dots 2, 3, 4 and 5, respectively). Dot 6, 2 $\mu$M bovine serum albumin treated with II. Dot 7, background II staining in the absence of protein.

Figure 12A:
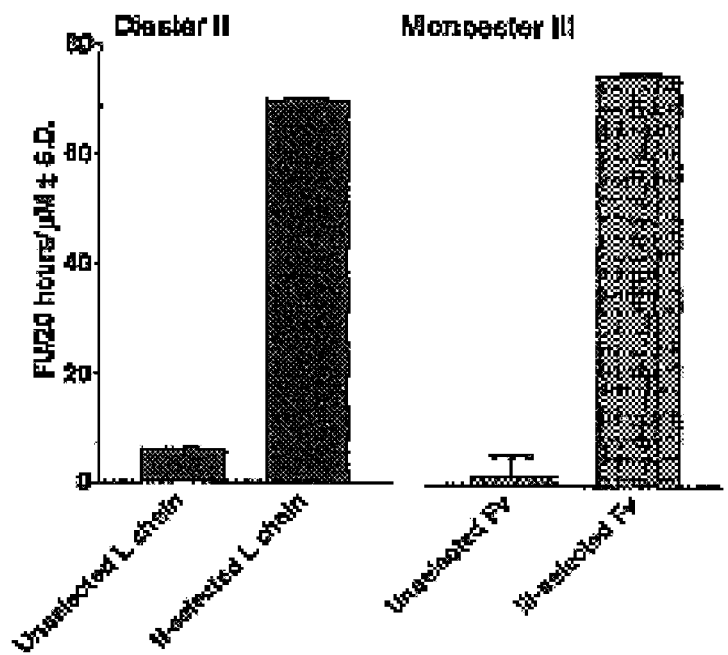

FIG. 12. Enriched catalytic activity in phage Abs selected on diester II and monoester III. Pro-Phe-Arg-MCA cleavage by unselected and II-selected lupus L chains (1 $\mu$M in A, black columns; 1 $\mu$M in B) and lupus III-selected Fv populations (0.2 $\mu$M in A, hatched columns). Substrate 400 $\mu$M. Elution of II-bound L chain phages was with 2-PAM (20 mM, 24h, 25° C.) and of III-bound Fv and L chain phages, with 2-mercaptoethanol. Catalysis assays were carried out using IMAC purified soluble Ab fragments. Values are means of 3 replicates after subtraction of background peptide-MCA cleaving activity in extracts from bacteria harboring phagemid DNA without an Ab insert (about 1 FU/hour).

Figure 13:
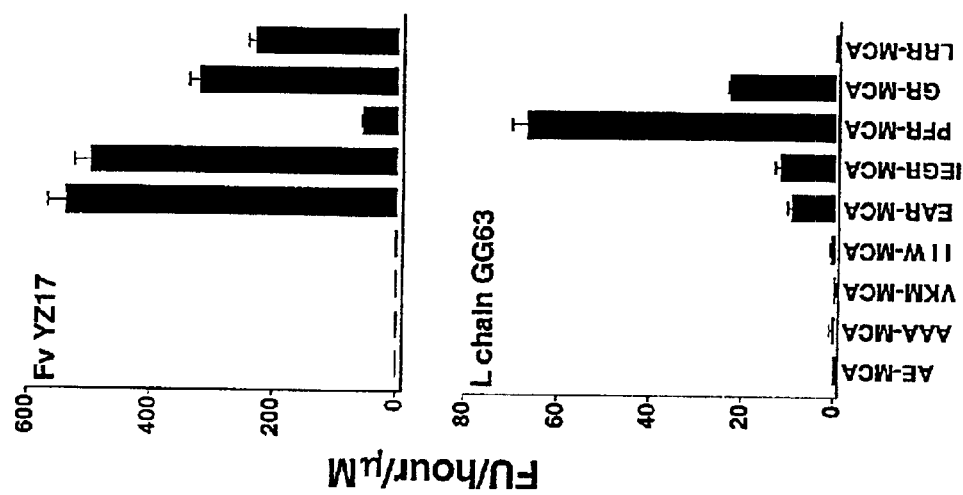

FIG. 13. Substrate selectivity of chemically selected Abs fragments. L chain GG63 (bottom). Fv YZ17 (top). Catalyst, 80 nM; peptide-MCA substrates, 200 $\mu$M. Cleavage rates were computed from duplicate assays by linear regression from plots of fluorescence intensity vs reaction time.

Figure 14:
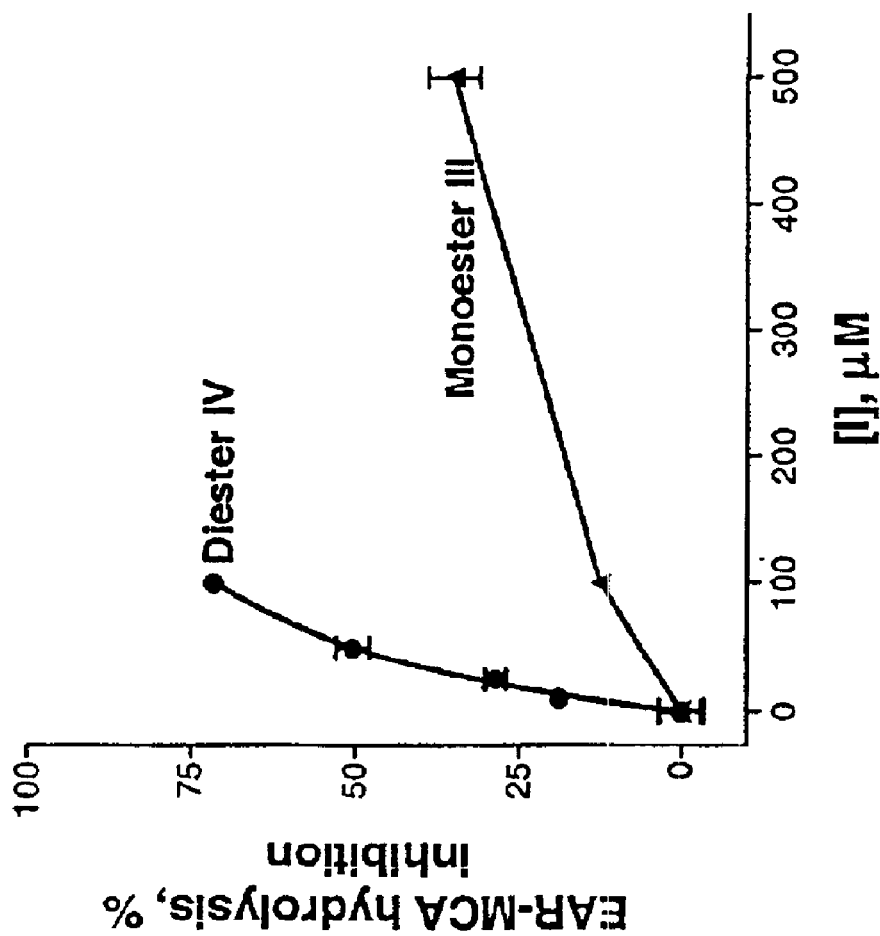

FIG. 14. Inhibition of monoester III-selected Fv YZ17 by diester IV. Substrate EAR-MCA, 200 $\mu$M; Fv YZ17, 20 nM.

Incubation for 15 hours. Substrate hydrolysis in the absence of inhibitor was 194 FU (100%). Inhibitors were preincubated at 1.2-fold the indicated concentration for 1 h with Fv prior to substrate addition. Values are means of 2 replicates.

Figure 15:
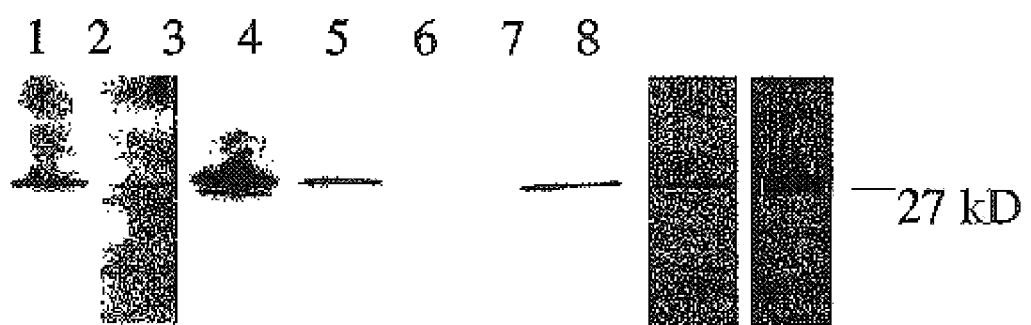

FIG. 15. Monoester III and diester IV binding by chemically selected antibody fragments Streptavidin-peroxidase stained blots of SDS-electrophoresis gels showing purified Fv YZ17 complexed to IV and III (lanes 1 and 2, respectively); purified L chain GG63 complexed to IV and III (lanes 3 and 4, respectively); periplasmic extracts of Fv clone YZ17 and control cells harboring phagemid vector without an antibody insert stained with diester II (lane 5 and 6, respectively). Lane 7, silver-stained SDS-gel of purified Fv clone YZ17; lane 8, anti-c-myc stained blot thereof. Treatment of the purified proteins (1 $\mu$M) and periplasmic extracts (dialyzed against assay diluent) with II (10 $\mu$M), III (100 $\mu$M) and IV (10 $\mu$M) was for 30 min, 37° C.

FIG. 16. Representative CRTSA structures are shown.

FIG. 17. Representative CRTSA structures are shown.

Figure 18:
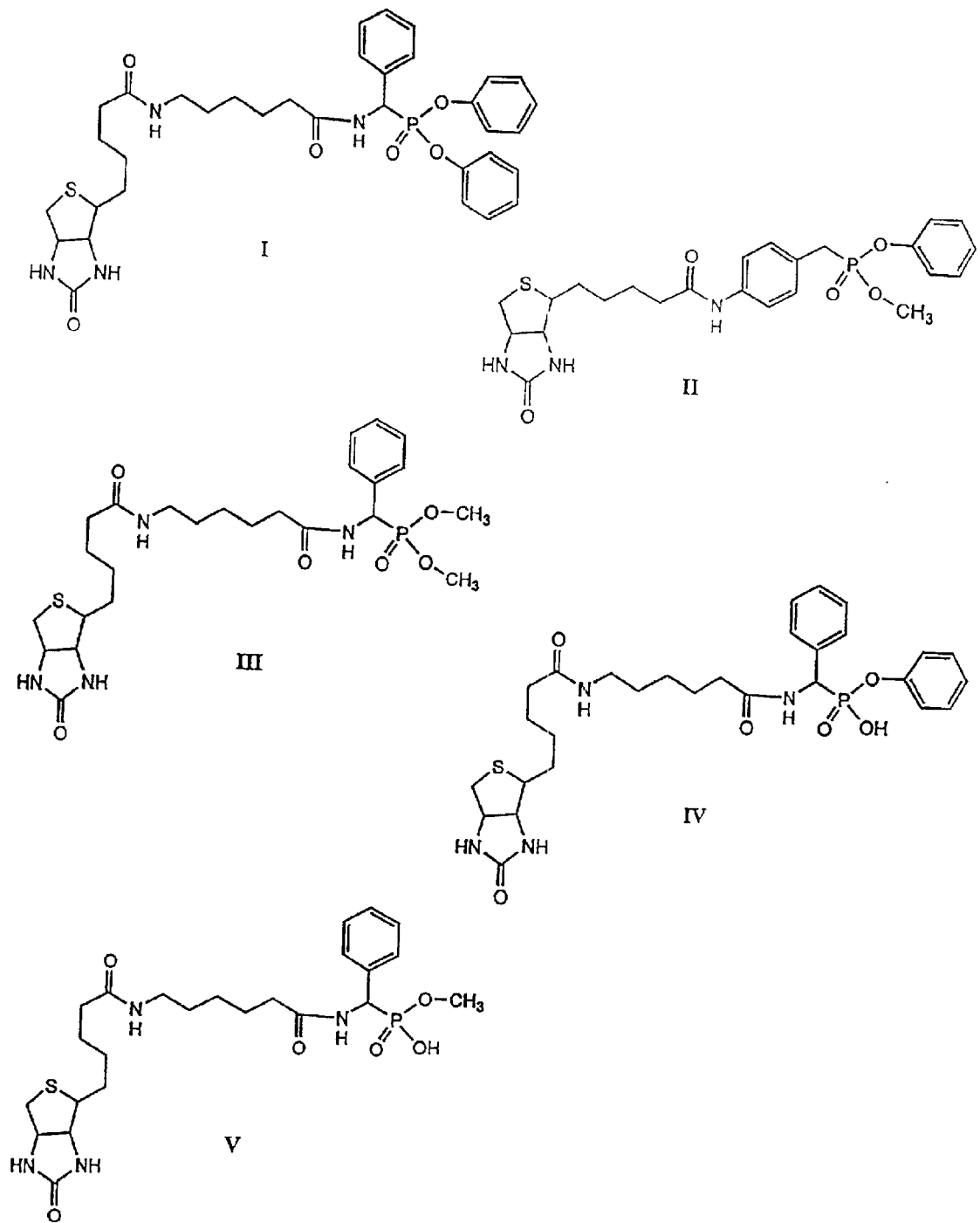

FIG. 18. Neutral diesters and monoesters suitable for use in the methods of the invention are shown.

FIGS. 19A and 19B. A list of antigens targeted by conventional monoclonal antibodies showing clinical promise. Such antigens are suitable targets for the catalytic antibodies of the present invention.

Figure 20:
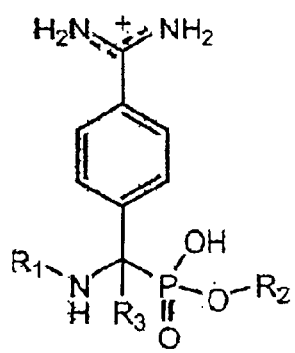

FIG. 20. An exemplary CRTSA of the invention.

DETAILED DESCRIPTION OF THE INVENTION

Methods are disclosed for stimulating synthesis of catalytic antibodies of predetermined specificity by the immune system. In one embodiment of the invention compositions and methods are provided for the generation of catalytic antibodies to a peptide antigen of choice. In another embodiment, compositions and methods are provided which are useful in passive immunotherapy modalities for the treatment of cancer and other medical conditions.

In another embodiment of the invention, vaccination protocols are described which elicit catalytic Ab production to predetermined viral or pathogenic antigens. The covalently reactive transition state antigen analogs disclosed preferentially stimulate the production of catalytic antibodies. Such antibodies provide superior protection against infection due to the presence of catalytic action against the target antigen which results in its permanent inactivation. Additionally, a single catalytic Ab molecule may be reused to inactivate multiple antigen molecules as compared to noncatalytic Abs which bind antigen reversibly and stoichiometrically.

The CRTSA of the invention is composed of certain basic elements. These include an electrophilic reaction center, and at least one peptide sequence corresponding to an epitope in a target antigen. In a preferred embodiment, the electrophilic reaction center is selected from the group of molecules shown in FIGS. 16 and 17. The CRTSA of the invention can optionally comprise a positively charged amino acid residue adjacent to the electrophilic reaction center and a second peptide sequence which together the first flank the electrophilic reaction center.

Immunization with transition state analogs (TSAs) has been proposed as a means to derive Abs that can bind the transition state, and thus lower the activation energy barrier for the reaction. The commonly used phosphonate analogs contain a tetrahedral phosphorus atom and a negatively charged oxygen atom attached to the phosphorus. Formation of the transition state of peptide bond cleavage is thought to involve conversion of the trigonal carbon atom at the cleavage site to the tetrahedral state, and acquisition of a negative charge by the oxygen of the carbonyl group. The conventional phosphonate TSAs may induce, therefore, the synthesis of Abs capable of binding the oxyanion structure and the tetrahedral configuration of the transition state. However, Abs to these TSAs, while capable of accelerating comparatively undemanding acyl transfer reactions, cannot effectively catalyze peptide bond cleavage. An antibody to a phosphinate TSA has recently been reported to slowly cleave a stable primary amide. It is possible that the anti-phosphinate Ab may permit superior transfer of a proton to the amide nitrogen at the scissile bond, compared to the more common anti-phosphonate Abs, which might account for its better catalytic activity.

Most enzymologists hold that phosphonate TSAs fail to elicit efficient catalytic Abs because they are poor transition state mimics, and because multiple transition states are involved. Enzymes use activated amino acid sidechains to catalyze peptide bond cleavage. For instance, the Ser hydroxyl group acquires enhanced nucelophilicity and the capability to mediate covalent catalysis due to formation of an intramolecular, hydrogen bonded network of the Ser, His and Asp residues. The phosphonate analogs do not contain structural elements necessary to bind the nucleophilic reaction center. Induction of the covalent catalysis capability in Abs is therefore unattainable using conventional phosphonate TSAs. Further, these TSAs do not exploit the existence of the germline encoded, serine protease site in Abs.

Covalently reactive antigen analogs (CRAA) have been described in U.S. Pat. No. 6,235,714, the entire disclosure of which is incorporated by reference herein.

Electrophilic CRTSAs are capable of reacting with the nucleophilic serine residue of the catalytic Abs. These antigen analogs have been applied to select catalysts from the antibody libraries. The logical extension of this strategy is to force the utilization of the serine protease sites for the synthesis of antibodies specific for individual target antigens, such as the epidermal growth factor receptor (EGFR). This can be achieved by immunization with the aforementioned electrophilic CRTSAs. Such CRTSAs promote clonal selection of B cells expressing the germline encoded serine protease sites on their cell surface. Further, the specificity for EGFR, for example, can be ensured by incorporating an appropriate antigenic epitope from EGFR which will flank the covalently reactive antigen analog structure.

Catalytic Ab synthesis has been documented in autoimmune disease [2, 4]. Further, the immune system is capable of producing Abs that catalyze the cleavage of exogenous antigens, including the cleavage of MV protein gp120. However, patients infected with the virus do not mount a catalytic Ab response to gp120. The HIV CRTSAs discussed herein will force the immune system to synthesize protective catalytic antibodies to HIV. Data are presented herein which support this approach. gp120 has been selected as the target antigen for the following reasons: (a) It is an essential constituent of HIV-1 for productive infection of host cells; (b) As a virus-surface protein, gp120 is readily accessible to Abs; and (c) Certain anti-gp120 Abs have been shown to arrest HIV infection.

Prior art methods have described combined administration of both CRAA and TSA separately. The CRTSA of the invention combine both of these reactivities in a single molecule. Incorporating all of the features of the transition state in a single analog molecule has unique advantages that are not expressed in analogs known in the art. Simultaneous recognition of these features by the catalysts is essential to ensure that the analog-catalyst binding occurs at the highest possible affinity. Catalysts that bind the CRTSAs can thus be anticipated to stabilize the corresponding transition state more strongly than the catalysts that bind TSAs alone or CRAAs alone. There is no assurance that a CRAA binding catalyst will also bind the TSA, or that a TSA binding catalyst will bind the CRAA. Thus, phage or B cell selection protocols in which sequential binding to TSAs and CRAAs are employed will not yield the same catalysts as those that bind the CRTSAs. Similar considerations apply in response to induction of antibody catalyst synthesis in response to immunization with these analogs. Binding of the analog to Ig on the cell surface stimulates clonal proliferation, during which the antibody variable regions undergo random sequence diversification. Cells expressing mutants with the highest affinity for the analog possess a survival advantage, in that they can preferentially bindg the analog and undergo further rounds of cell division. Sequential immunization with the CRAA and the TSA (heterologous immunization) may provide for selection of mutants that can bind both analogs, but strengthened binding of one analog may be accompanied by weaked binding for the other analog, as there is no selective advantage for the cell to retain its original Ig specificity. Thus, the use of CRTSAs as immunogens can be anticipated to induce the synthesis of catalysts that stabilize the transition state more strongly than antibodies produced following sequential immunization with CRAAs and TSAs.

Phosphonate monoesters have been assumed to serve as noncovalent transition state analogs for enzymes capable of catalyzing transacylation reactions. Here, we present evidence for the covalent reaction of certain serine proteinases and peptidase antibody fragments with monophenyl amino (4-amidinophenyl)methanephosphonate derivatives. Stable adducts of the N-biotinylated monophenyl ester with trypsin and antibody fragments were evident under conditions that disrupt noncovalent interactions. The reaction was inhibited by the active site-directed reagent diisopropyl fluorophosphate. Mass spectrometry of the fragments from monoester-labeled trypsin indicated phosphonylation of the active site. Irreversible inhibition of trypsin- and thrombin-catalyzed hydrolysis of model substrates was observed. Kinetic analysis of inactivation of trypsin by the N-benzyloxycarbonylated monoester suggested that the first-order rate constant for formation of covalent monoester adducts is comparable to that of the diester adducts (0.47 $min^{-1}$ vs. 2.0 $min^{-1}$). These observations suggest that the covalent reactivity of phosphonate monoesters contributes to their interactions with serine proteinases, including certain proteolytic antibodies.

In yet another embodiment of the invention, the reactivity of phosphonate ester probes with several available proteolytic antibody (Ab) fragments was characterized. Irreversible, active-site directed inhibition of the peptidase activity was evident. Stable phosphonate diester-Ab adducts were resolved by column chromatography and denaturing electrophoresis. Biotinylated phosphonate esters were applied for chemical capture of phage particles displaying Fv and light chain repertoires. Selected Ab fragments displayed enriched catalytic activity inhibitable by the selection reagent. Somewhat unexpectedly, a phosphonate monoester also formed stable adducts with the Abs. Improved catalytic activity of phage Abs selected by monoester binding was also evident. Turnover values ($k_{cat}$) for a selected Fv construct and a light chain against their preferred model peptide substrates were, respectively, 0.5 min$_{-1}$ and 0.2 min$_{-1}$, and corresponding Michaelis-Menten constants (Km) were, 10 $\mu$M and 8 $\mu$M. The covalent reactivity of Abs with phosphonate esters suggests their ability to recapitulate the catalytic mechanism utilized by classical serine proteases.

The CRTSAs of the invention and the resulting catalytic antibodies have at least three major applications. The first application is directed to the generation of catalytic antibodies in either humans or animals following immunization with a CRTSA designed for a particular medical disorder. The catalytic antibodies so generated would then be administered to patients to inactivate targeted antigen moieties. In this scenario, should the patient experience adverse side effects, the immunizing CRTSA may be administered to irreversibly inactivate the catalytic antibody. The CRTSAs in this embodiment would be synthesized with a B cell epitope only in order to minimize immunogenicity.

In the second application, CRTSAs may be administered to patients for the purposes of actively immunizing the patient against particular pathological to generate a state of protective immunity. These CRTSAs would be administered as a CRAA-adjuvant complex.

Finally, the CRTSAs of the invention may be administered to patients who are currently expressing catalytic antibodies in association with a medical disorder such as autoimmune disease or multiple myeloma. CRTSAs may be designed with specifically react with the antibodies present. Inhibition of catalytic function should result in an amelioration of the disease state. Again, these CRTSAs are designed to contain a minimally immunogenic B cell epitope only.

The detailed description set forth below describes preferred methods for practicing the present invention. Methods for selecting and preparing CRTSAs, stimulating the production of catalytic antibodies to predetermined antigens and improved methods for isolating the same are described.

I. Selection and Preparation of CRTSAs

The covalently reactive transition state antigen analogs of the invention are prepared using conventional organic synthetic schemes. The novel CRTSAs of the invention contain an electron withdrawing or electron donating substituent flanked by at least one peptide sequence derived from proteins associated with a particular peptide antigen to be targeted for cleavage and the intended use of the CRTSA.

Selection of suitable flanking amino acid sequences depends on the particular peptide antigen targeted for cleavage. For example, viral coat proteins, certain cytokines, and tumor-associated antigens contain many different epitopes. Many of these have been mapped using conventional monoclonal Ab-based methods. This knowledge facilitates the design of efficacious covalently reactive transition state antigen analogs useful as catalytic antibody inhibitors as well as inducers of catalytic antibodies with catalytic activities against predetermined target antigens.

The amino acids flanking the reaction center represent the sequence of the targeted epitope in defined polypeptides that play a role in disease, or to which autoantibodies are made in disease.

The structural features of the CRTSAs are intended to permit specific and covalent binding to immature, germline encoded antibodies as well as mature antibodies specialized to recognize the targeted epitope. Based on the tenets of the clonal selection theory, the CRTSAs are also intended to recruit the germline genes encoding the catalytic antibodies for the synthesis of mature antibodies directed towards the targeted epitope.

Polypeptides to be targeted include soluble ligands and the membrane bound receptors for these ligands.

Microbial proteins can also be targeted for catalysis by the antibodies of the present invention. These include but are not limited to gp120, gp160, Lex 1 repressor, gag, pol, hepatitis B surface antigen, bacterial exotoxins (diptheria toxin, *C. tetani* toxin, *C. botulinum* toxin, pertussis toxin).

Neoplastic antigens will also be incorporated into therapeutically beneficial CRTSAs. These include but are not limited to EGF, TGF$\alpha$, p53 products, prostate specific antigen, carcinoembryonic antigen, prolactin, human chorionic gonadotropin, c-myc, c-fos, c-jun, p-glycoproteins, multidrug resistance associated proteins, metalloproteinases and angiogenesis factors.

Receptors for neoplastic antigens will also be targeted for antibody-mediated catalysis. These include EGFR, EGFR mutants, HER-2, prolactin receptors, and steroid receptors.

Inflammatory mediators are also suitable targets for catalysis. Exemplary molecules in this group include TNF, IL-1 beta, IL-4 as well as their cognate receptors.

Preexisting catalytic antibodies are found in autoimmune disease and lymphoproliferative disorders. The harmful actions of these catalytic antibodies will be inhibited by administering CRTSAs to patients. CRTSAs designed to be weakly immunogenic will be administered which covalently interact with antibody subunits with specificity for VIP, Arg-vasopressin, thyroglobulin, thyroid peroxidase, IL-1, IL-2, interferons, proteinase-3, glutamate decarboxylase.

For maximum selectivity, the flanking peptide sequences comprise an epitope which is targeted for cleavage. For example, an epitope present in the epidermal growth factor receptor is incorporated in a CRTSA of the present invention. In another embodiment of the invention, an epitope present in HIV gp120 is incorporated into a CRTSA.

The discussion below relates to an exemplary CRTSA for the treatment of HIV infection which comprises both a B cell epitope and a T cell epitope to maximize the immunogenicity of the CRTSA. While HIV specific CRTSA are described one of ordinary skill in the art appreciates that the following concepts and methodology may be applied to design CRTSA immunologically specific for any target epitope. CRTSAs of the B cell epitope will be designed to elicit catalytic Abs. An exemplary B cell epitope is derived from the CD4 binding site, which is generally conserved in different HIV-1 strains. The CD4 binding site of gp120 is a suitable target, further, because unlike many other epitopes, it is accessible to Abs on the native viral surface. It is known that the CD4 binding site is a conformational determinant.

In the present invention, preparation of a catalytic Ab that recognizes a specific portion of the CD4 binding site (as opposed to the entire CD4 binding site) is described. Additional peptide epitopes in gp120 (or other HIV proteins) that might be suitable targets for catalytic Abs will also be identified. Because cleavage of gp120 may lead to global changes in the protein conformation, accompanied by loss of biological activity, certain gp120 peptide epitopes may be appropriate targets of catalytic Abs even if they do not participate directly in HIV-1 binding to host cells or HIV-1 interactions with intracellular components. These and other targets are also contemplated to be within the scope of the present invention.

T cell help for Ab synthesis is potentially subject to restriction in different individuals due to major histocompatibility complex (MHC) polymorphism. In the present invention, mouse strains with well-defined genetic backgrounds will be used as models for the elicitation of catalytic immunity in response to B-T epitope conjugates. A "universal" T-helper epitope recognized promiscuously by various MHC class II alleles will be utilized. Another benefit of this approach is that it is readily adaptable to human clinical trials.

The envelope glycoproteins of HIV-1 are synthesized as a single 160 kD precursor, gp160. This protein is cleaved at the Arg511-Ala512 bond by a cellular protease, producing gp120 and the integral membrane protein gp41. The biological activity of gp120 is a key ingredient in initial binding of host cells by HIV-1, propagation of the virus, and its toxic effects on uninfected neurons and other cells. Binding of a conformational epitope of gp120 to CD4 receptors on host cells is the first step in HIV-1 infection. Individual amino acids constituting this epitope appear to be located in the second (C2), third (C3), and fourth (C4) conserved gp120 segments. These are gp120 residues 256, 257, 368–370, 421–427 and 457. Monoclonal antibodies that bind the CD4 binding site have been described. Since the CD4 binding site is a conformational epitope, distant residues that are not themselves constituents of the epitope may be important in maintaining the ability to bind CD4.

gp120 interactions with other host cell proteins are also essential for virus propagation. For example, binding of gp120 by calmodulin may be involved in HIV-1 infectivity, as revealed by the inhibitory effect of calmodulin antagonists. Asp180 located between the V1 and V2 regions of gp120 is critical for viral replication. Similarly, the V3 loop may be essential for infectivity. It is clear, therefore, that structural determinants in gp120 other than those constituting the CD4 binding site are necessary for virus genome replication, coat protein synthesis, and virus particle packaging.

Trypsinization of gp120 blocks its neurotoxic effects. Treatment of HIV-1 particles with trypsin, mast cell tryptase or Factor Xa attenuates their infectivity. Cleavage of gp120 at residues 269–270 or 432–433 destroys CD4 binding capability, whereas cleavage at residues 64–65, 144–145, 166–167, 172–173 or 315–316 does not affect CD4 binding. On the other hand, cleavage at the Arg315-Ala316 peptide bond located in the V3 loop of gp120 by a cellular protease is believed to be essential for productive viral infection. A dipeptidylpeptidase expressed on the host cell-surface (CD26) has been proposed as being responsible for cleavage at Arg315-Ala316. This cleavage site is located in the principal neutralizing determinant (PND), which is a component of the V3 gp120 loop to which protective Abs are readily synthesized. It has been hypothesized that Ab binding to the PND blocks the cleavage of gp120 by a host cell protease, resulting in HIV neutralization. There is no evidence that the PND plays a direct role in HIV binding by CD4, but its participation in binding by the HIV coreceptors has been suggested.

Efficient Ab synthesis by B cells is dependent in part on recruitment of T helper cells, which, once sensitized, secrete the necessary stimulatory cytokines and activate B cells by direct contact mediated through accessory molecules, such as CD4 on T helper cells and B7 on B cells. Recruitment of Ag-specific T cells occurs through recognition by the T cell receptor (TCR) of the complex of a processed Ag epitope bound to MHC class II molecules.

The peptide-based vaccines are formulated by covalently linking a T cell epitope to a B cell epitope, against which the host synthesizes Abs. The T epitope binds MHC class II molecules on the surface of antigen-presenting cells, and the MHC class II complex of the B-T epitopes is then bound by the TCR. Different individuals in an outbred species express different MHC class II alleles involved in Ag presentation to T cells (I-E and I-K loci). Ideally, a peptide vaccine should be free of MHC restrictions, i.e., a robust Ab response should be provoked regardless of the MHC class II variations involved in Ag presentation.

The interactions between MHC class II molecules, the TCR and the Ag epitope are quite promiscuous. Thus, certain peptides can serve as universal T epitopes, i.e., these peptides can bind the different MHC class II alleles efficiently. Further, there is no apparent restriction of recognition of the peptides at the level of the different types of TCRs. Such peptides are suitable T epitope components in vaccines designed to neutralize HIV through elicitation of a protective Ab response, as described in the present invention.

By incorporating appropriate structure in the immunogens capable of inducing the synthesis of Abs that combine specificity for gp120 with rapid peptide bond cleaving activity, an immunotherapeutic agent for the treatment of AIDS will be generated.

Methods are provided for the synthesis of peptide analog formulations that elicit the synthesis of specific and efficient catalytic Abs capable of protecting against HIV infection. Earlier studies have suggested that polyreactive catalytic activity of germline encoded Abs can be recruited and improved by immunization of mice with the serine-reactive CRTSA of a gp120 peptide. The elicitation of a catalytic Ab response should provide superior protection against HIV-1 infection compared to a noncatalytic Ab response.

The following synthetic immunogens will be prepared and assessed:

A) synthetic immunogens
  a) the phosphonate monoester CRTSA of a B cell epitope of gp120 (residues 421–436) conjugated to a T-helper epitope from tetanus toxoid (residues 830–844) [designated B-T epitope];
  (b) the unmodified peptide form of the B-T epitope.
(B) Immunize non-autoimmune mice (strain B10.BR) and autoimmune mice (MRL/1 pr) with the two immunogens from (A) and study the following activities of IgG purified from the sera:
  (a) binding and cleavage of the CRTSA B-T epitope, and the unmodified B-T epitope;
  (b) binding and cleavage of monomer full-length gp120; and (c) binding and cleavage of native cell-surface-bound gp120.

Immunogens

The prototype vaccine capable of eliciting catalytic antibodies to HIV contains: 1) an epitope to which B cells can make high affinity antibodies (B epitope); 2) an epitope that is bound by MHC class II antigens and presented to T cells (T epitope); and 3) a structural mimic of the transition state formed during peptide bond cleavage, which is intended to provoke the synthesis of antibodies capable of stabilizing the transition state, and thus catalyzing the cleavage reaction.

B epitope component: Loss of infectivity following cleavage of gp120 can be achieved by directing the catalyst to cleave a peptide bond located in an epitope of gp120 that plays an important role in the infection process. Note that cleavage of gp120 at a bond distant from the biologically important determinants may also lead to loss of gp120 function, because the conformation of the gp120 fragments may be altered "globally" relative to the parent protein. The probability of neutralizing viral infectivity can be increased by directing the Ab to recognize an epitope that is a known target of neutralizing Abs. Cleavage of the CD4 binding site is an attractive mechanism to achieve HIV neutralization for the following reasons: CD4-gp120 binding is an essential step in HIV entry into host cells; cleavage of the CD4 binding at the 432–433 bond by trypsin is known to block the ability of gp120 to bind CD4; Abs to the CD4 binding site are known to inhibit HIV infection; the CD4 binding site on native gp120 expressed on the HIV surface is exposed to the environment (as opposed to several other epitopes of monomeric gp120 that are buried in native gp120 oligomers) [32]; and, the CD4 binding site is quite conserved in different subtypes of HIV-1. The linear peptide sequence composed of gp120 residues 421–436 has been selected as the B epitope component of the immunogen in the present project (KQIINMWQEVGKAMYA (SEQ ID NO: 1)). Mutagenesis studies have shown that this region of gp120 make important contributions in CD4 binding.

T epitope component: To recruit T cell help for synthesis of anti-gp120 Abs, a fifteen amino acid peptide (QYIKANSKFIGITEL (SEQ ID NO: 2) corresponding to residues 830–844 of tetanus toxin will be placed on the N terminal side of the B epitope. The presence of the T epitope in the vaccine construct eliminates the need to conjugate the B epitope to a large carrier protein. Several previous studies have shown that comparatively short linear peptides that include a T and a B epitope are capable of provoking efficient Ab synthesis to the B epitope [42]. The tetanus toxin T epitope to be employed in the present invention is known to serve as a T epitope in hosts expressing diverse class II alleles, and has been characterized, therefore, as a "universal" T epitope [43]. Further, a gp120 B epitope linked to this T epitope is described to induce anti-gp120 Ab synthesis. The "universality" of the T epitope, although deduced from human studies, probably extends to the mouse, because class II restrictions tend to be conserved phylogenetically. Regardless of the possible differences on this point between man and mouse, the mouse strains to be utilized in the present invention have been matched for class II alleles involved in recruitment of T cell help for Ab synthesis ($A^k E^k$ haplotype), eliminating concern that differential T helper recruitment might contribute to variations in catalytic Ab responses.

Assembly of immunogens: Synthesis of the 31 residue ground state B-T construct (designated unmodified B-T epitope) composed of tetanus toxin residues 830–844 at the N terminus and gp120 residues 421–436 at the C terminus will be done by conventional solid phase synthesis on an Applied Biosystems synthesizer. Mass spectrometry and $^1$H and $^{13}$CNMR will be done to confirm the structures.

II. Administration of CRTSAs

CRTSAs as described herein are generally administered to a patient as a pharmaceutical preparation. The term "patient" as used herein refers to human or animal subjects.

The pharmaceutical preparation comprising the CRTSAs of the invention are conveniently formulated for administration with a acceptable medium such as water, buffered saline, ethanol, polyol (for example, glycerol, propylene glycol, liquid polyethylene glycol and the like), dimethyl sulfoxide (DMSO), oils, detergents, suspending agents or suitable mixtures thereof. The concentration of CRTSAs in the chosen medium will depend on the hydrophobic or hydrophilic nature of the medium, as well as the other properties of the CRTSA. Solubility limits may be easily determined by one skilled in the art.

As used herein, "biologically acceptable medium" includes any and all solvents, dispersion media and the like which may be appropriate for the desired route of administration of the pharmaceutical preparation, as exemplified in the preceding paragraph. The use of such media for pharmaceutically active substances is known in the art. Except insofar as any conventional media or agent is incompatible with the CRTSA to be administered, its use in the pharmaceutical preparation is contemplated.

Conventional immunization methods will applied to induce catalytic Ab synthesis. Three intraperitoneal and one intravenous injections of the immunogens (about 100 µg peptide each) will be administered. The final immunization will be carried out intravenously. RIBI will be used in the animal studies. For human use, alum will be employed as the adjuvant. Alum is approved for human use and has previously been shown to provoke Ab synthesis to a B-T epitope similar to those proposed in the present invention. RIBI is a low toxicity replacement for Freund's Complete Adjuvant, and reproducibly facilitates good Ab responses to a variety of Ags. Analysis of two adjuvants is advantageous because the quality and magnitude of Ab responses to vaccines can be influenced by adjuvants, via effects of the cytokines and TH subpopulations recruited by the adjuvants on B.

CRTSAs may be administered parenterally by intravenous injection into the blood stream, or by subcutaneous, intramuscular or intraperitoneal injection. Pharmaceutical preparations for parenteral injection are commonly known in the art. If parenteral injection is selected as a method for administering the molecules of the invention, steps must be taken to ensure that sufficient amounts of the molecules reach their target cells to exert a biological effect.

The pharmaceutical preparation is formulated in dosage unit form for ease of administration and uniformity of dosage. Dosage unit form, as used herein, refers to a physically discrete unit of the pharmaceutical preparation appropriate for the patient undergoing treatment. Each dosage should contain a quantity of active ingredient calculated to produce the desired effect in association with the selected pharmaceutical carrier. Procedures for determining the appropriate dosage unit are well known to those skilled in the art.

The pharmaceutical preparation comprising the CRTSA may be administered at appropriate intervals, for example, twice a day until the pathological symptoms are reduced or alleviated, after which the dosage may be reduced to a maintenance level. The appropriate interval in a particular case would normally depend on the condition and the pathogenic state sought to be treated in the patient.

III. Administration of Catalytic Antibodies

The catalytic antibodies described herein are generally administered to a patient as a pharmaceutical preparation.

The pharmaceutical preparation comprising the catalytic antibodies of the invention are conveniently formulated for administration with a acceptable medium such as water, buffered saline, ethanol, polyol (for example, glycerol, propylene glycol, liquid polyethylene glycol and the like), dimethyl sulfoxide (DMSO), oils, detergents, suspending agents or suitable mixtures thereof. The concentration of catalytic antibodies in the chosen medium will depend on the hydrophobic or hydrophilic nature of the medium, as well as the other properties of the catalytic antibodies. Solubility limits may be easily determined by one skilled in the art.

As used herein, "biologically acceptable medium" includes any and all solvents, dispersion media and the like which may be appropriate for the desired route of administration of the pharmaceutical preparation, as exemplified in the preceding paragraph. The use of such media for pharmaceutically active substances is known in the art. Except insofar as any conventional media or agent is incompatible with the catalytic antibody to be administered, its use in the pharmaceutical preparation is contemplated.

Conventional passive immunization methods will be employed when administering the catalytic antibodies of the invention. In a preferred embodiment, Abs will be infused intravenously into the patient. For treatment of certain medical disorders, steps must be taken to ensure that sufficient amounts of the molecules reach their target cells to exert a biological effect.

The lipophilicity of the molecules, or the pharmaceutical preparation in which they are delivered may have to be increased so that the molecules can arrive at their target locations. Furthermore, the catalytic antibodies of the invention may have to be delivered in a cell-targeted carrier so that sufficient numbers of molecules will reach the target cells. Methods for increasing the lipophilicity and targeting of therapeutic molecules, which include capsulation of the catalytic antibodies of the invention into antibody studded liposomes, are known in the art.

The catalytic antibodies that are the subject of the present invention can be used as antibody fragments or whole antibodies or they can be incorporated into a recombinant molecule or conjugated to a carrier such as polyethylene glycol. In addition any such fragments or whole antibodies can be bound to carriers capable of causing the transfer of said antibodies or fragments across cell membranes as mentioned above. Carriers of this type include but are not limited to those described (Cruikshank et al. in the Journal of Acquired Immune Deficiency Syndromes and Human Retrovirology, March 1997).

The pharmaceutical preparation is formulated in dosage unit form for ease of administration and uniformity of dosage. Dosage unit form, as used herein, refers to a physically discrete unit of the pharmaceutical preparation appropriate for the patient undergoing treatment. Each dosage should contain a quantity of active ingredient calculated to produce the desired effect in association with the selected pharmaceutical carrier. Procedures for determining the appropriate dosage unit are well known to those skilled in the art. For example, the half-life of syngeneic IgG in the human is about 20 days. Over this period, 60,480 Ag molecules will be cleaved by one molecule of an antibody with a turnover of 2.1/min (which is the turnover of a human anti-VIP L chain isolated from a phage display library [14]. It can be seen, therefore, that the peptidase antibodies can express considerably more potent antigen neutralizing activity than stoichiometric, reversibly-binding molecules. Note that the antibody light chains discussed here were selected based on their antigen-binding affinity, a procedure that favors tight binding to the antigen, but will not select catalysts with the best turnover. Antibodies produced by immunization with CRTSAs and isolated by appropriate selection methods, as disclosed here, will express considerably greater turnover. Such catalytic antibodies can be used to treat disease at substantially lower doses of corresponding noncatalytic antibodies.

The pharmaceutical preparation comprising the catalytic antibodies may be administered at appropriate intervals, for example, twice a week until the pathological symptoms are reduced or alleviated, after which the dosage may be reduced to a maintenance level. The appropriate interval in a particular case would normally depend on the condition and the pathogenic state sought to be treated in the patient.

CRTSAs will be selected that will generate catalytic antibodies for passive or active immunotherapy that will fulfill the standard criteria for acceptable prophylatic or therapeutic agents: (1) Cleavage of the target peptide antigen by the catalytic antibody will lead to a beneficial change in a pathological process by either functionally activating or functionally inactivating the target peptide antigen; and (2) Administation of said catalytic antibodies or the induction of their production in the body by means of immunization with a CRTSA will result in a favorable therapeutic index such that the clinical benefit gained outweighs the morbidity associated with andy side-effects. Discussions of how such criteria are established for the acceptability of prophylatic or therapeutic agents are common in the art can can be found in such texts as *Guide to Clinical Trials* by Bert Spilker, Raven Press, New York, 1991.

Suitable categories of prophylatic or therapeutic target peptide antigens for the practice of the present invention include but are not limited to cytokines, growth factors, cytokine and growth factor receptors, proteins involved in the transduction of stimuli intiated by growth factor receptors, clotting factors, integrins, antigen receptors, enzymes, transcriptional regulators particularly those involved in cellular program (differentiation, proliferation and programmed cell death) control, other inducers of these cellular programs, cellular pumps capable of expelling anticancer agents, microbial and viral peptide antigens.

Conventional monoclonal antibodies that act to inhibit the function of particular target molecules are among the most common type of therapeutic agent under development for clinical use by biotechnology and pharmaceutical companies. Some of these have shown substantial clincal promise and any exposed peptide target antigens that are part of the same molecular functional unit are therefore shown to be particularly well suited as potential targets for the catalytic antibodies that are the subject of the present invention. The catalytic antibodies comtmplated in the present invention will constitute a major inprovement over such conventional monoclonals becaule of their ability to affect many target molecules vs. just one and because of the resulting dramatic decrease in the cost of treatment. The availability of peptide bonds within these targeted antigens can be determined by methods well established in the art including but not limited to a demonstration of cleavage following exposure to proteolytic enzymes and catalytic light chains capable of cleaving a range of peptide bonds.

A listing of some of the antigens targeted by conventional monoclonal antibodies showing clinical promise and the corresponding medical indications are shown in FIGS. 19A and 19B.

Thus, it is an object of the present invention to provide a covalently reactive transition state antigen analog, and a method of producing it, which is capable of 1) provoking the generation of catalytic and nucleophilic antibodies specific to a predetermined antigen of the invention and/or 2) irreversibly inhibiting the catalysis by antibodies associated with autoimmune disease and certain lymphoproliferative disorders. Further objects reside in providing processes for preparing antigens and their corresponding antibodies, and in providing assays and methods of using these antibodies as beneficial therapeutic agents.

The following examples are provided to facilitate an understanding of the present invention. They are not intended to limit the invention in any way.

EXAMPLE 1

Irreversible Inactivation of Trypsin by a Phosphonate Monoester Derivative

Phosphonate monoesters are comparatively stable compounds thought to approximate the stereoelectronic features of the rate-limiting transition state of certain transacylation reactions ($TAs^2$). Consequently, they are useful in study of catalytic mechanisms, particularly for ceratin Abs capable of catalyzing esterolytic reactions (1,2). TA binding by enzyme active sites is usually viewed as involving noncovalent interactions at the tetrahedral phosphorus atom and its oxyanion, corresponding to the tetrahedral carbon atom and the developing charge on the carbonyl group in the transition state (3,4, and references therein). Recently, phosphonate monoester derivatives were observed to bind irreversibly to certain naturally occurring proteolytic Abs (5), suggesting that noncovalent mimicry of the oxyanionic transition state may not fully explain the reactivity of these compounds. Previously, the monoesters have been held inert to nucleophilic attack by serine proteinase active sites owing to the delocalized negative charge carried by the oxygen atoms. Phosphonate diesters, on the other hand, are well known to bind the active site of serine proteinases covalently by phosphonylation of the hydroxyl function of active site serine residue (6).

The catalytic mechanisms utilized by naturally occurring Abs are understood only minimally. In the present study, therefore, we employed a better-characterized catalyst to study the covalent reactivity of the phosphonate monoesters, i.e., trypsin. Phosphonate monoesters were bound covalently by the active site of trypsin, the catalytic activity was inhibited irreversibly, and the rate constant for formation of the monoester-enzyme adduct was comparable to that of the homologous diester. Studies using thrombin and recombinant Ab fragments confirmed the irreversible binding and inhibition of catalytic activity, suggesting that the covalent reactivity is a general feature of phosphonate monoester interaction with serine proteinases.

Materials and Methods (2-Biotinamido)ethylamido-3,3'-dithiodipropionic acid N-hydroxysuccinimide ester, succinimidyl 6-(biotinamide) hexanoate, trypsin (porcine, type IX), diisopropyl fluorophosphate (DFP), and VPR-MCA were from Sigma (St. Louis, Mo.); acetonitrile (HPLC grade) was from Fisher Scientific (Pittsburgh, Pa.); EAR-MCA was from Peptides International (Louisville, Ky.); 8–25% PHAST electrophoresis gels, ECL molecular mass markers, streptavidin-horseradish peroxidase conjugate, and ECL kits were from Amersham Pharmacia Biotech (Piscataway, N.J.); and N-tosyl-phenylalanine chloromethyl ketone-treated bovine trypsin was from Pierce (Rockford, Ill.). 1-Methyl-2-pyrrolidinone, N,N-dimethylformamide and N,N-diisopropylethylamine were of peptide synthesis grade (Applied Biosystems, Foster City, Calif.). Other reagents for chemical synthesis were of reagent grade. Thrombin (human, a) was purified as described in (7). HPLC was conducted using a Waters DELTA-600 system equipped with a 2487 UV/VIS detector (Milford, Mass.) and YMC-pack ODS AM columns [YMC USA (Milford, Ma.); 4.6.times.250 mm (for analysis) and 20.times.250 mm (for purification)] with the following mobile phase: A, 0.05% trifluoroacetic acid in water; B, 0.05% trifluoroacetic acid in acetonitrile [flow rate 1.0 ml/min (for analysis) or 10 ml/min (for purification)]. Purity of the compounds obtained is represented by % peak area of the desired compound in HPLC chromatograms at 220 nm. $^1$H-NMR (400 MHz) spectra were measured in $D_{20}$-acetonitrile-d3 containing 3-(trimethylsilyl)-1-propanesulfonic acid sodium salt as internal standard. Stock solutions of compounds 1–5 (10 mM) in N,N-dimethylformamide were stored at −80° C. and were analyzed by HPLC periodically to confirm their integrity.

Synthesis of Phosphonate Compounds 1–5

Diphenyl N-(benzyloxycarbonyl)amino(4-amidinophenyl)methanephosphonate (1). This compound was synthesized according to (8) with slight modifications. The iminoester prepared from diphenyl [N-(benzyloxycarbonyl)amino](4-cyanophenyl)methane phosphonate (1.5 g, 3.0 mmol) was dissolved in a mixture of methanol (30 ml) and 0.5 M $NH_3$ in 1,4-dioxane (15 ml), the solution stirred at room temperature overnight, solvent was removed and the oily residue dissolved in $CHCl_3$ (30 ml). Diethyl ether (100 ml) was added, the precipitate collected by filtration, washed with diethyl ether (30 ml×5) and dried in vacuo [yield 1.2 g (73%)]. The crude product was judged sufficiently pure for biotinylation. For use in kinetic studies, further purification was carried out by HPLC (100 mg crude 1) yielding 36 mg 1. [$t_R$ 31.58 min, purity 99% (A:B 80:20 to 20:80 in 60 min); m/z (ESI) 516 $(M+H)^+$, 1031 $(2M+H)^+$].

Monophenyl N-(benzyloxycarbonyl)amino(4-amidinophenyl)methanephosphonate (2). Crude 1 (200 mg) was allowed to hydrolyze in acetonitrile (5 ml) and 2.5% aq. $Na_2CO_3$ (15 ml) at room temperature overnight, pH was adjusted to 3 with 6 N HCl, and the mixture subjected to preparative HPLC and lyophilization, yielding a colorless powder [yield 83 mg; $t_R$ 17.70 min, purity 91% (A:B 80:20 to 20:80 in 60 min); m/z (ESI) 440 $(M+H)^+$, 880 $(2M+H)^+$].

Monophenyl-N-[2-(biotinamido)ethylamido-3,3'-dithiodipropionyl]amino(4-amidinophenyl) methanephosphonate (3). 2 (83 mg, 0.19 mmol) was dissolved in 30% HBr in acetic acid (5 ml) and the resulting yellow solution was stirred at room temperature for 3 h. Procedures described for 1 were carried out to precipitate, wash and dry the amine derivative. The resulting anine and (2-biotinamido)ethylamido-3,3'-dithiodipropionic acid N-hydroxysuccinimide ester (100 mg, 0.17 mmol) were allowed to react in 1-methyl-2-pyrrolidinone (4 ml) containing N,N-diisopropylethylamine (88 ml, 0.56 mmol) overnight at room temperature. Preparative HPLC and lyophilization yielded a colorless fluffy powder [yield 110 mg (83%); $t_R$ 18.11 min, purity 94% (A:B 90:10 to 20:80 in 45 min); m/z (ESI) 766 $(M+H)^+$; $^1$H-NMR spectrum consistent with assigned structure].

Monophenyl N-[6-(biotinamido)hexanoyl]amino(4-amidinophenyl)methanephosphonate (4). The benzyloxycarbonyl group of 2 was removed and the resulting amine (50 mg, 0.09 mmol) was biotinylated by means of succinimidyl 6-(biotinamide)hexanoate (49 mg, 0.11 mmol) as described for 3. The crude product was purified by HPLC to give a colorless fluffy powder [yield 51 mg (89%); $t_R$ 15.05 min, purity >99% (A:B 90:10 to 20:80 in 45 min); m/z (ESI) 645 $(M+H)^+$].

Diphenyl-N-[2-(biotinamido)ethylamido-3,3'-dithiodipropionyl]amino(4-amidinophenyl) methanephosphonate (5). The benzyloxycarbonyl group of crude 1 was removed and biotin was incorporated in the resulting amine (110 mg, 0.18 mmol) by means of (2-biotinamido)ethylamido-3,3'-dithiodipropionic acid N-hydroxysuccinimide ester (125 mg, 0.22 mmol) as described for 3. The crude product was purified by HPLC to give a colorless fluffy powder [yield 20 mg (13%); $t_R$ 24.95 min, purity 96% (A:B 90:10 to 20:80 in 45 min); m/z (ESI) 843 $(M+H)^+$, 865 $(M+Na)^+$; $^1$H-NMR spectrum consistent with assigned structure].

Binding and Enzyme Acivity Assays

Binding assay. Trypsin and Ab fragment clones were allowed to react with phosphonates 3 and 4 under conditions described in legends for FIGS. 3 and 7. The reaction mixtures were subjected to gel filtration, precipitated with an equal volume of 20% (w/w) trichloroacetic acid, the pellet was collected by centrifugation, SDS was added to 2%, the samples boiled in a water bath for 5 min and analyzed by SDS-PAGE on 8–25% PHAST gels. The gels were electroblotted onto nitrocellulose membrane (TransBlot; Biorad, Hercules, Calif.), blocked with 5% nonfat milk in PBS-T, washed with PBS-T, treated with a streptavidin-horseradish peroxidase conjugate (1:1000) in 10 mM sodium phosphate, pH 7.4, containing 137 mM NaCl, 2.7 mM KCl, and 0.025% Tween-20 (PBS-T) and enzyme-bound phosphonate detected using an ECL kit and X-OMAT film (Kodak).

Inactivation assay. Trypsin (0.75 nM) in PBS-T was incubated in the presence of 3 (12.5 M–2.5 mM) at 37° C. for 30 min in 96-well Microfluor II white plates (Dynex Technologies, Va.). EAR-MCA was added to the solutions (concentrations of trypsin, substrate and 3 in the assay medium were 0.6 nM, 0.2 mM and 10 M–2.0 mM, respectively) and the resulting coumarin derivative after 1 h incubation was determined by fluorometry ($l_{em}$ 470 nm, $l_{ex}$ 360 nm; LS50B luminescence spectrometer equipped with a plate reader, Perkin Elmer, Shelton, Colo.). To assess irreversibility, phosphonate compounds in the reaction mixtures were removed by gel-filtration in PBS-T (Spin-out 6000 columns; Chemicon International, Temecula, Calif.) or diluted to noninhibitory concentrations prior to measurement of catalytic activity. For kinetic analyses, aliquots of the trypsin-phosphonate reaction mixtures were withdrawn at various intervals and diluted 500-fold (1) or 50-fold (2) with PBS-T. EAR-MCA (0.4 mM, 25 l) was added to 25 l of the diluted reaction mixtures, and the residual activity was measured fluorometrically. Dissociation constants for the initial noncovalent complex ($K_i$) and the rate constants for the conversion of the noncovalent complex to the irreversibly inactivated enzyme ($k_2$) were determined from Kitz-Wilson's plots (9), in which the reciprocal apparent first-order inactivation rate constant ($k_{app}$) was plotted versus reciprocal inhibitor concentration. Thrombin and Ab catalysis assays were carried out similarly using VPR-MCA (25 mM) and EAR-MCA (0.4 mM), respectively. Preparation of recombinant Ab fragments and their sources have been described in (5,10).

Mass Spectrometry

Trypsin (1 mg) was allowed to react with 4 (3 mg) in 1 ml 100 mM $NH_4HCO_3$ (pH 8.0) at room temperature. Unreacted 4 was removed by gel filtration (10DG column, Bio-Rad). The protein-containing fraction (2 ml) was treated with urea (8 M) and dithiothreitol (20 mM, 22° C., 30 min), followed by iodoacetamide (50 mM, 22° C., 30 min), and then desalted by HPLC (Vydac protein C4 column; 0.1% trifluoroacetic acid in 5% acetonitrile/water, 5 min, then 0.1% trifluoroacetic acid in 59% acetonitrile/water, 10 min, 1.0 ml/min). The protein fraction was concentrated to 950 μl by vacuum centrifugation, the pH adjusted to 8.0 using 2 M Tris base, and then treated with N-tosyl-phenylalanine chloromethyl ketone-treated bovine trypsin (50 μg) at room temperature overnight. To separate biotinylated peptides, the solution was allowed to bind SoftLink Avidin Resin in 10 mM sodium phosphate, pH 7.4, containing 137 mM NaCl, and 2.7 mM KCl (1 ml gel; Promega, Madison, Wis.; 30 min with rotation). The slurry was packed in a polypropylene column and washed with the same buffer (10 ml), and bound peptides eluted with 8 M urea in 100 mM ammonium bicarbonate, pH 8.0, containing 10 mM methylamine. The eluate was desalted, lyophilized, and subjected to MALDI-TOF MS with a-cyano-4-hydroxycinnamic acid as the matrix.

Results

Syntheses of phosphonates 1–5. The structure of phosphonates 2–5 (FIG. 2) is based on diphenyl N-benzyloxycarbamido(4-amidinophenyl) methanephosphonate (1), which has previously been described to be a potent and irreversible inhibitor of trypsin, thrombin and certain other serine-proteinases (8). N-Benzyloxycarbonylated diester 1 was synthesized essentially according to the reported procedure (8), and its monoester derivative 2 was prepared by hydrolysis of 1. The protecting group N-benzyloxycarbonyl was removed from diphenyl phosphonate 1 and its monophenyl derivative 2, and biotin was introduced at the amino function to yield diester 5 and monoester 3, respectively. This permitted sensitive detection of enzyme-phosphonate adducts on electrophoresis gels by an electrochemiluminescence reaction using a streptavidin-horseradish peroxidase conjugate. Monoester 4 was prepared by essentially the same method as for 3 (the two compounds are identical except that 4 contains a non-reducible linker to allow mapping of the trypsin binding site under reducing conditions).

Figure 3:
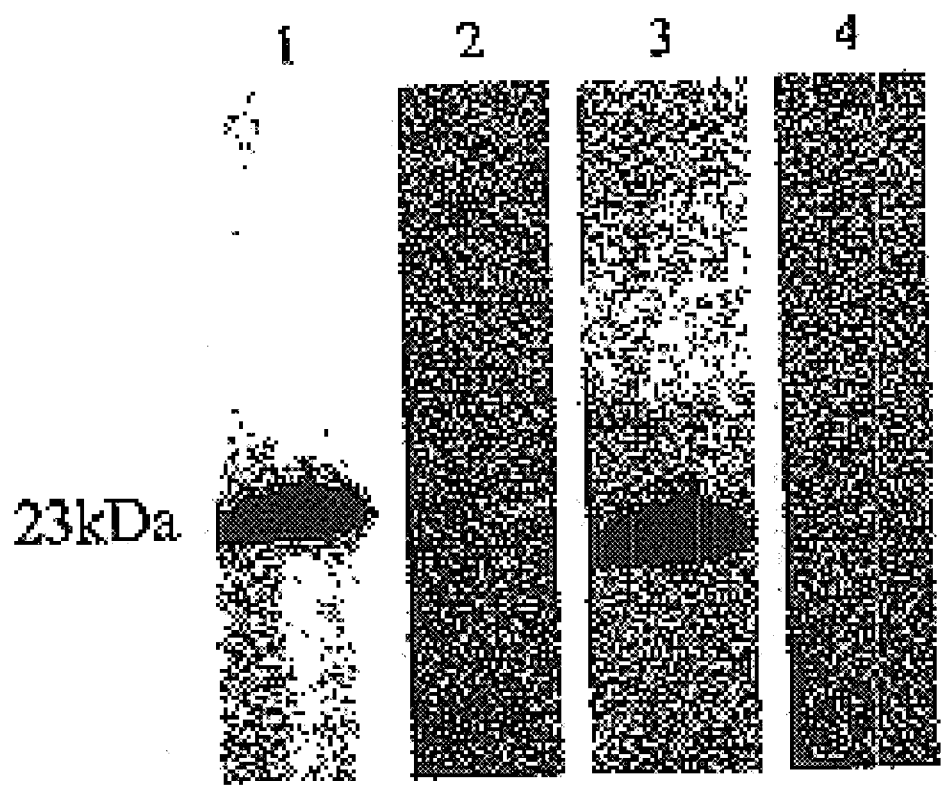

Active site-directed covalent binding. Trypsin incubated with 3 and 5 was subjected to gel filtration, precipitation with trichloroacetic acid and then boiled in SDS prior to electrophoresis to remove unbound and non-covalently bound phosphonate. Trypsin bands labeled with monoester 3 and diester 5 were observed using a biotin-specific electrochemiluminescence reaction (FIG. 3). Pretreatment with 1 mM DFP, a classical active site-directed inhibitor of serine proteinases, completely inhibited labeling of the enzyme by 3 and 5, indicating that both phosphonate esters bind the enzyme active site.

Figure 4A:
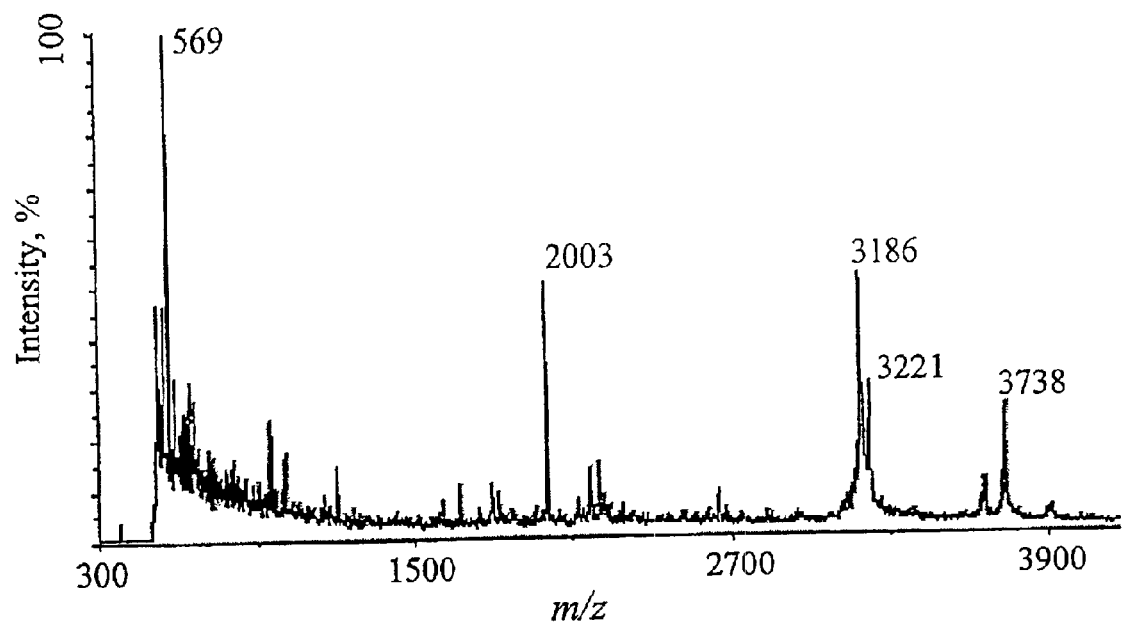
Figure 4B:
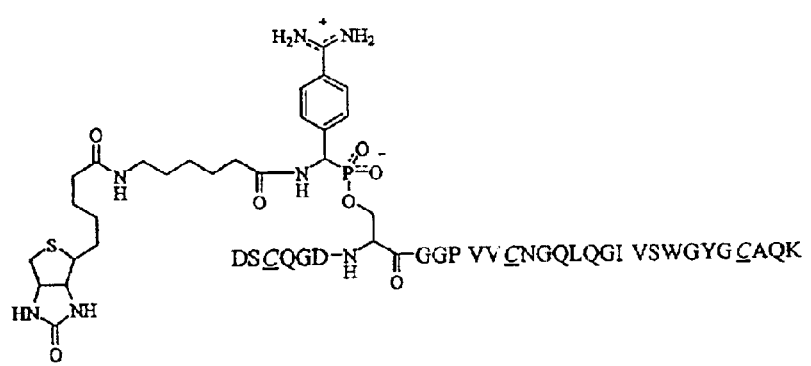

Direct evidence for active site modification by the phosphonate monoester was obtained by MS analysis of fragments obtained by tryptic digestion of trypsin adduct followed by affinity chromatography on immobilized avidin monomers. The molecular ion of the phosphonylated fragment 189–218 (m/z 3738) was evident (FIG. 4A). This fragment contains the active site Ser195 residue. The proposed structure of the adduct (FIG. 4B) is consistent with the observed m/z and is identical to the "aged" complex formed by phosphonate diesters with a serine proteinase (11,12). Additional constituents identified were: (a) fragment ions corresponding to the dephosphonylated peptide and the free phosphonic acid derivative of 4 (m/z 3186 and 569, respectively); and (b) avidin fragments at m/z 3221 and 2003 corresponding to residues 101–128 and 112–128, respectively. As the samples analyzed by MS were purified by affinity chromatography on immobilized avidin, coincidental contamination with the free phosphonic acid derivative (m/z 569) and unreacted peptide (m/z 3186) is unlikely. Presumably, these constituents were detected because of partial degradation of the phosphonylated peptide adduct during sample handling. Avidin fragments detected are attributable to tryptic digestion of the affinity column matrix (the tryptic digest was applied to the avidin column without inactivation of the enzyme).

Irreversible inactivation. The reactions of an enzyme (E) with a covalent active site modifier (I) can be represented by the following scheme:

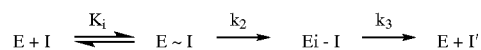

where $K_i$ is the dissociation constant for the noncovalent complex (E-I), $k_2$, the first-order rate constant for formation of the covalent complex Ei-I, and $k_3$, the first-order rate constant for decomposition of Ei-I.

Concentration-dependent inhibition of trypsin-catalyzed EAR-MCA hydrolysis by monoester 3 was observed [9.9–80% inhibition at 0.01–2.0 mM 3; s.d. <5.6%, n=3;

enzyme 0.6 nM; substrate 0.2 mM; enzyme activity without 3,301 FU/h]. The inhibitory effect was irreversible, as judged by the following observations. Trypsin (200 nM) was pretreated with 3 (1.0 mM) for 30 min followed by dilution of the reaction mixture to non-inhibitory concentrations of 3 prior to assay for enzyme activity (1000-fold dilution; 3 concentration during enzyme assay 1.0 mM). Marked inhibition of trypsin activity was observed (85% inhibition; activity without 3, 92–105 FU/h; no inhibition by 1.0 mM 3 was observed unless the enzyme was pretreated with the compound prior to incubation with substrate). Evidently, the dilution step failed to dissociate the enzyme-monoester complexes formed during the pretreatment step, suggesting an apparent irreversible inhibition mode. Removal of unbound phosphonates by gel filtration of trypsin pretreated with monoester 3 (800 mM) and diester 5 (80 mM) at 37° C. (22 h) did not restore the enzyme activity [activity levels following gel filtration of 3-treated and 5-treated trypsin: 27.6±2.6 FU/h and 5.0±0.1 FU/h, respectively, compared 33.2±2.6 FU/h and 6.5±0.2 FU/h without removal of 3 and 5, respectively; activity levels in control trypsin without phosphonate: 288.4±8.4 FU/h (without gel filtration) and 308.2±13.4 FU/h (t=0 following gel filtration)]. Moreover, incubation of the 3-enzyme adduct isolated by gel filtration for 17 h in buffer failed to restore the activity appreciably (50.2±7.0 FU/h), suggesting that the Ei-I complex does not decompose to yield active enzyme ($k_3 \sim 0$). Under these conditions, Kitz-Wilson plots (9) of inhibitor concentration vs apparent first-order inactivation rate constants ($k_{app}$) can be applied for determination of $K_i$ and $k_2$.

Figure 5A:
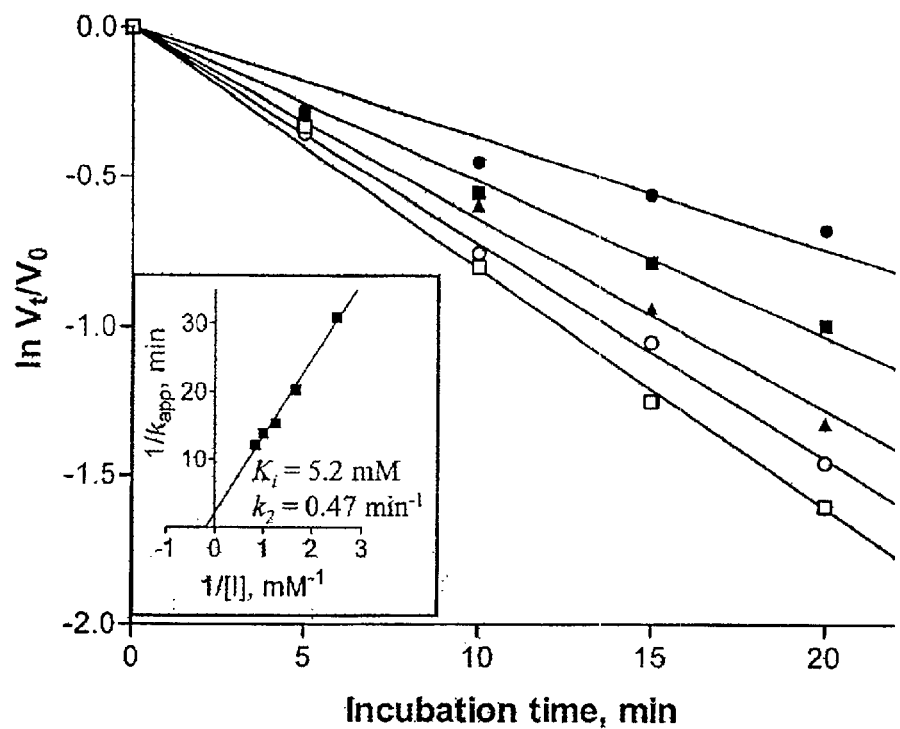
Figure 5B:
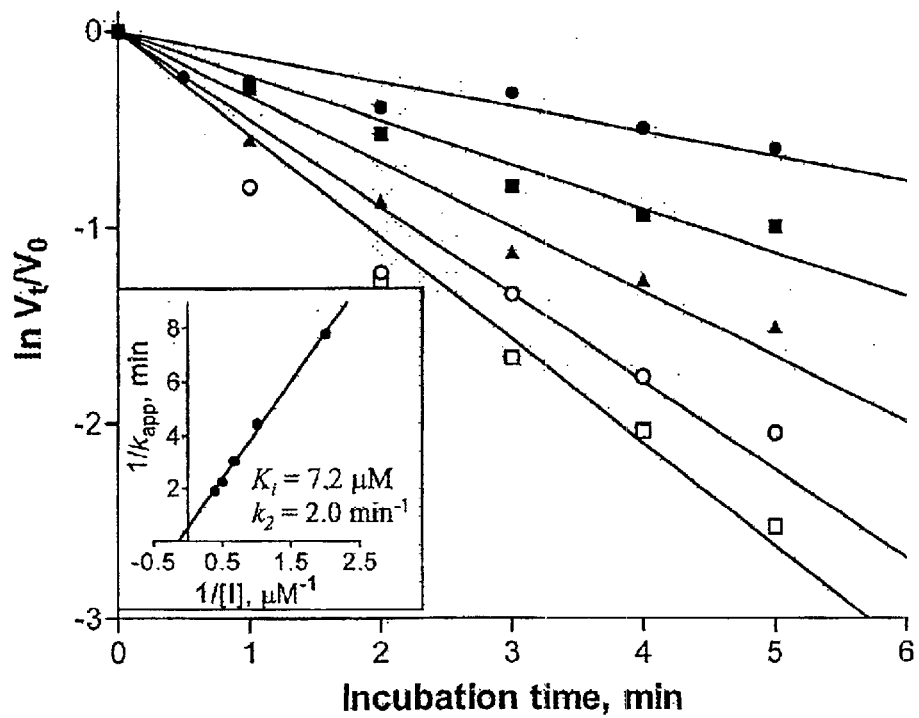

Kinetic studies were carried out using diester 1 and monoester 2 containing N-benzyloxycarbonyl in place of the biotin substituent. Diester 1 has previously been described to inhibit trypsin (8), and preliminary kinetic analysis in the present study indicated that 1 is a superior inhibitor of trypsin compared to the biotin-containing diester 5 utilized for catalyst binding studies ($k_{app}/[I]$ 3703 and 0.23 $M^{-1}$ $sec^{-1}$, respectively; determined at 1.5 mM 1 and 0.3 mM 5). Apparently, inclusion of the biotin group interferes with the enzyme-phosphonate interactions. $k_{app}$ values for monoester 2 and diester 1 were obtained as the slope of plots of $In[V_t/V_0]$ vs time at varying phosphonate concentration, where $V_0$ represents initial velocity of substrate hydrolysis in the absence of phosphonate and $V_t$, initial velocity after treatment with phosphonate esters (FIG. 5). $k_2$ for formation of the covalent monoester adduct was only 4-fold lower than the diester adduct (0.47 $min^{-1}$ vs. 2.0 $min^{-1}$). $K_i$ values for the monoester 2 and diester 1 noncovalent complexes were 5.2 mM and 7.2 M, respectively.

Figure 6A:
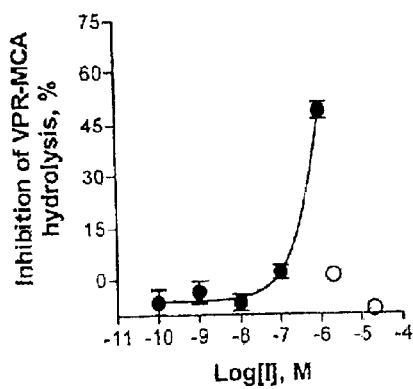
Figure 6B:
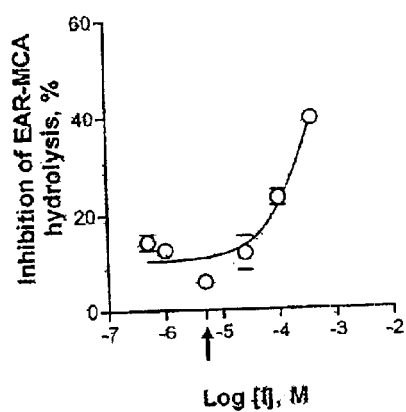
Figure 6C:
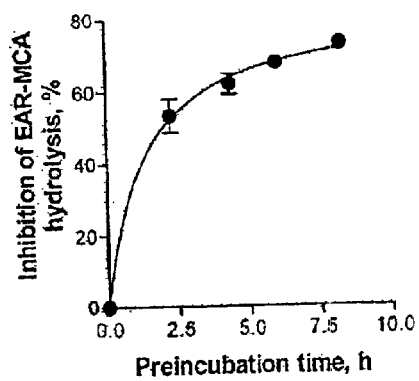
Figure 7:
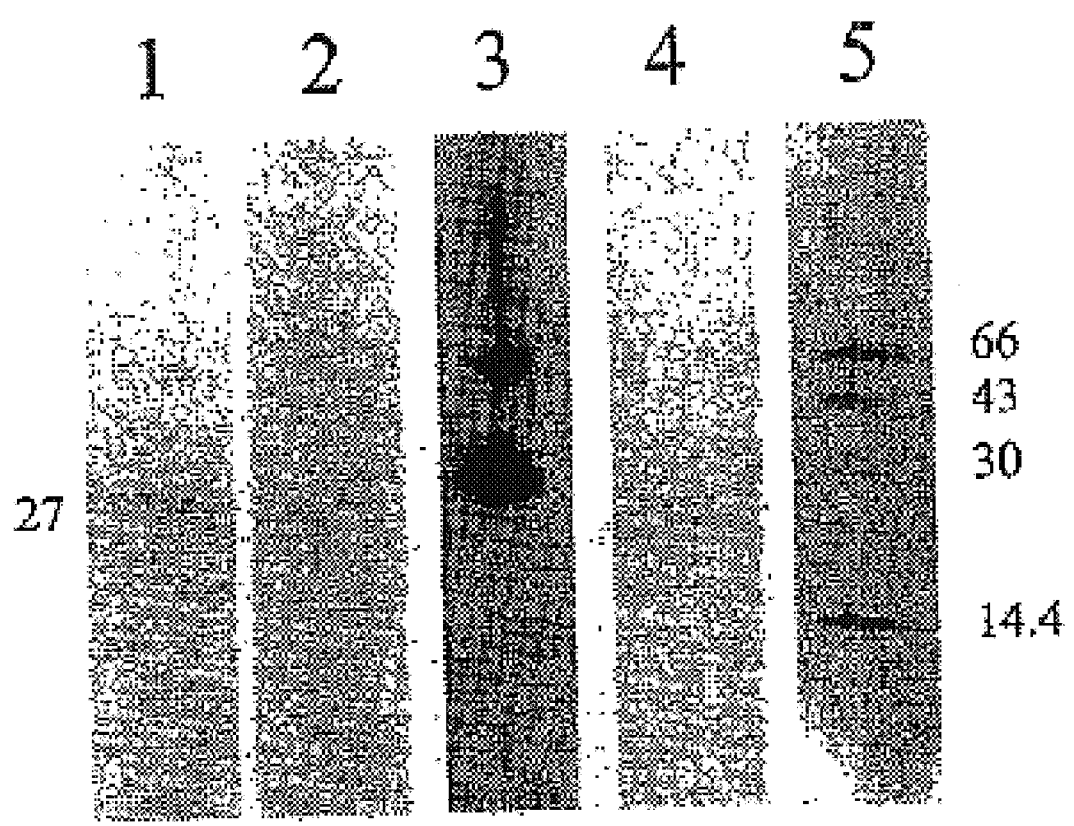

Irreversible inactivation and binding of thrombin and Ab fragments. Procedures identical to those used for trypsin were applied to study effect of monoester on thrombin and a catalytic Ab fragment (clone YZ17, GenBank accession number 12957377; FIG. 6). Pretreatment of the catalysts with 3 produced inhibition of activity despite dilution of the reaction to non-inhibitory concentrations. Ab clones isolated by selection of phage libraries on a phosphonate monoester (Fv clone YZ17) and a diester (L chain clone SK35; GenBank accession number AF425258) were analyzed for monoester 4 binding. Biotin-containing 27 kD adducts stable to denaturing treatments were observed (boiling, trichloroacetic acid-precipitation, SDS treatment; FIG. 7). Consistent with the tendency of L chains to form aggregates, the dimer and higher order 4-labeled states of SK35 L chain were observed. Under equivalent conditions, an Ab fragment identified as a catalyst based on random screening assays (10) failed to form stable 4-adduct [L chain clone c23.5 (lane 4); GenBank accession numbers 896288]. The adduct formation was inhibited by DFP (FIG. 7, lane 2), suggesting that the binding is active site directed.

Phosphonate monophenyl esters 24 were observed to irreversibly bind and inhibit the active site of trypsin. Irreversible interactions of monoester 4 with thrombin and a proteolytic Fv clone were also evident. The first-order rate constant for formation of the covalent trypsin adduct of monoester 2 ($k_2$) is comparable to the corresponding value for diester 1 adduct. This is noteworthy because the delocalized negative charge carried by the oxygen atoms is anticipated to result in reduced electrophilicity. For instance, spontaneous hydrolysis of the phosphonate monoesters under basic conditions occurs 2–3 orders of magnitude slower than of the diesters[3] (13). Moreover, trypsin inactivation by 2 occurs rapidly ($k_2/K_i$=90 $M^{-1}$ $min^{-1}$) compared to spontaneous hydrolysis of analogous monoaryl esters[4] (these reactions correspond to dephenoxylation by the enzyme and dephenoxylation by $OH^-$, respectively; 13–15). Thus, the inactivation of trypsin by monoester 2 may be accelerated by the enzyme itself, as reported to be the case with other organophosphorus inhibitors (16,17). Increased electrophilic reactivity of the phosphorus atom can be anticipated, for instance, if the enzyme active site disrupts resonance hybridization around the O—P—O center, resulting in a greater localization of the negative charge on one of the oxygens. An analogous activation scheme is proposed for the covalent reaction of phosphonate monoesters with -lactamase (18).

$K_i$ values computed from Kitz-Wilson plots indicate that the overall strength of noncovalent enzyme-2 interactions is weaker than for enzyme-1 interactions ($\Delta G$ 3.2 and 7.3 kcal/mol at 37° C., respectively; $\Delta G = -RTlnK_i$, where $\Delta G$, R and T represent the Gibbs free energy change, gas constant and absolute temperature, respectively). Interpreting the low affinity of monoester 2 for trypsin, however, is complicated by the following factors. First, the binding strength derived from $K_i$ values potentially includes contacts at subsites in the ground states as well as those unique for the transition state (e.g., oxyanion stabilization). Second, in the case of the diester, stabilizing hydrophobic interactions at the second phenyl group can not be excluded in view of reports describing preferential recognition of hydrophobic moieties by the $S_1'$ subsite of trypsin (19,20). The $K_i$ values, therefore, do not shed light on the energetic contribution of phosphonate oxyanion interactions with trypsin. Previous studies have provided strong support for the role of the phosphonate oxyanion as a mimic of the negative charge found on the carbonyl oxygen in the transition state of transacylation reactions (21). Despite the comparatively large $K_i$ value, phosphonate monoesters hold promise as analogs capable of combining noncovalent and covalent reaction pathways to probe serine proteinase active sites. In future studies, the available means to improve inhibitory potency include optimization of contacts in the transition state as well as the ground state of the enzyme-inhibitor complex, for instance, by incorporation of peptidic groups on the flanks of the phosphonate group and removal of steric conflicts that may interfere with oxyanion binding.

With respect to proteolytic Abs, distinct levels of monoester binding by different L chain clones prepared under identical conditions were observed, and one L chain clone did not show detectable covalent binding, judged by denaturing electrophoresis. The apparent presence of Ab nucleophiles with varying levels of monoester 4 binding activity is consistent with the sequence diversity of Ab combining sites. The identity of the nucleophiles in different clones, the structural factors governing their chemical reactivity and the relationship of the phosphonate binding sites with catalysis remain to be elucidated. Moreover, the catalytic activities need not be directly correlated with the level of covalent binding, as catalysis requires additional hydrolysis and product release steps. Previous studies have focused on the link between noncovalent binding of phosphonate monoesters and the esterolytic activity of certain Abs (22). No explanation has been available for the unusual properties of several esterolytic Abs raised by immunization with the monoesters, including unusual kinetic behavior inconsistent with simple oxyanion stabilization[5] (23), apparent irreversible binding to the substrate (24), and the presence of a serine proteinase-like Ser-His catalytic dyad in the Ab combining site (25). Recognition of phosphonate monoester covalent reactivity may help explain the discrepancies, as the immunization procedure can be hypothesized to allow adaptive maturation of nucleophilic Abs.

REFERENCES FOR EXAMPLE I

1. Tramontano, A., Janda, K. D., and Lerner, R. A. (1986) *Science* 234, 1366–1570.
2. Pollack, S. J., Jacobs, J. W. and Schultz, P. G. (1986) *Science* 234, 1570–1573.
3. Hasserodt, J. (1999) *Synlett*, 2007–2022.
4. Golineli-Pimpaneau, B. (2000) *Curr. Opin. Struct. Biol.* 10, 697–708.
5. Paul, S., Tramontano, A., Gololobov, G., Zhou, Y.-X., Taguchi, H., Karle, S., Nishiyama, Y., Planque, S., and George, S. (2001) *J. Biol. Chem.* 276, 28314–28320.
6. Oleksyszyn, J. and Powers, J. C. (1994) in *Methods in Enzymology, Vol. 244. Proteolytic Enzymes: Serine and Cysteine Peptidases* (Barrett, A. J. ed.) pp. 423–441, Academic Press, New York.
7. Fenton, J. W., II, Fasco, M. J. and Stackrow, A. B. (1977) *J. Biol. Chem* 252, 3587–3598.
8. Oleksyszyn, J., Boduszek, B., Kam, C.-M. and Powers, J. C. (1994) *J. Med. Chem.* 37, 226–231.
9. Kitz, R. and Wilson, I. B. (1962) *J. Biol. Chem.* 237, 3245–3249.
10. Gao, Q. S., Sun, M., Rees, A. R. and Paul, S. (1995) *J. Mol. Biol.* 253, 658–664.
11. Bertrand, J. A., Oleksyszyn, J., Kam, C.-M., Boduszek, B., Presnell, S., Plaskon, R. R., Suddath, F. L., Powers, J. C. and Williams, L. D. (1996) *Biochemistry* 35, 3147–3155.
12. Bone, R., Sampson, N. S., Bartlett, P. A., Agard, D. A. (1991) *Biochemistry* 30, 2263–2272.
13. Behrman, E. J., Biallas, M. J., Brass, H. J., Edwards, J. O., and Isaks, M. (1970) *J. Org. Chem.* 35, 3063–3075.
14. Whithey, R. J. (1969) *Can. J. Chem.* 47, 4383–4387.
15. Moss, R. A. and Ragunathan, K. G. (1999) *Langmuir* 15, 107–110.
16. Schowen, R. L. (1978) in *Transition States of Biochemical Processes* (Gandour, R. D., Schowen, R. L. eds.) pp.86, Plenum, New York.
17. Kovach, I. M., Larson, M., and Schowen, R. L. (1986) *J. Am. Chem. Soc.* 108, 5490–5495.
18. Pratt, R. F. (1989) *Science* 246, 917–919.
19. Schellenberger, V., Turck, C. W., Hedstrom, L., and Rutter, W. J. (1993) *Biochemistry* 32, 4349–4353.
20. Schellenberger, V., Turck, C. W. and Rutter, W. J. (1994) *Biochemistry* 33, 4251–4257.
21. Gigant, B., Charbonnier, J.-B., Eshhar, Z., Green, B. S. and Knossow, M. (1997) *Proc. Natl. Acad. Sci. USA* 94, 7857–7861.
22. Stewart, J. D. and Benkovic, S. J. (1995) *Nature* 375, 388–391.
23. Tramontano, A. (1994) *Appl. Biochem. Biotechnol.* 47, 257–275.
24. Rao, G. and Philipp, M. (1991) *J. Protein Chem.* 10, 117–122.
25. Zhou, G. W., Guo, J., Huang, W., Fletterick, R. J. and Scanlan, T. S. (1994) *Science* 265, 1059–1064.

Footnotes for Example I

[2] Abbreviations: Ab, antibody; DFP, diisopropyl fluorophosphate; EAR-MCA, N-tert-butoxycarbonyl- -benzyl-Glu-Ala-Arg 4-methylcoumaryl-7-amide hydrochloride; ESI, electrospray ionization; FU, fluorescence unit; L chain, light chain; MALDI-TOF MS, matrix-assisted laser desorption ionization time-of-flight mass spectrometry; TA, transition state analog; $t_R$, retention time; VPR-MCA, tert-butoxycarbonyl-Val-Pro-Arg 4-methylcoumaryl-7-amide.

[3] For example, the apparent first-order rate constant for hydrolysis of monophenyl methanephosphonate (2.0 mM) in 2.12 M aq. NaOH at 39° C. is $0.228 \times 10^{-3}$ min$^{-1}$, corresponding to a half life of 50 h, whereas hydrolysis of diphenyl esters by equimolar NaOH is complete within minutes.

[4] Second-order rate constants (M$^{-1}$ min$^{-1}$) of p-nitrophenyl methanephosphonate, which contains a more reactive leaving group than 2–4, are on the order of $10^{-11}$–$10^{-9}$ for hydrolysis in buffered solutions (pH 7.6, 30° C.) and $10^{-7}$–$10^{-3}$ in alkaline solutions (pH 8–10, 30–50° C.).

[5] Observed $K_i/K_m$ are frequently unequal to $k_{cat}/k_{uncat}$. Simple charge complementarity, therefore, does not explain the observed rate accelerations.

EXAMPLE II

Phosphonate Ester Probes for Proteolytic Antibodies

Abs and Ab L chains are reported to catalyze the cleavage of VIP$_2$ (1,2), the HIV coat proteins gp41 (3) and gp120 (4), Arg-vasopressin (5), thyroglobulin (6), factor VIII (7), prothrombin (8) and various model peptidase substrates (5,9, 10). Recent studies suggest that the peptidase activity is a heritable function encoded by a germline V region gene(s) (11,12). In principle, the immune system may be capable of recruiting the catalyst-encoding germline V gene(s) to elaborate specific proteolytic Abs directed to diverse polypeptide antigens, much like noncatalytic Abs capable of high affinity binding to different antigens can be developed by somatic sequence diversification of the same germline V genes. Introduction of single replacement mutations in Ab combining sites can result in gain of proteolytic (13) and esterase activities (14), underscoring the potential contributions of V region diversification in maturation of Ab catalytic activities.

The presence of a serine protease-like catalytic triad in a model proteolytic Ab L chain has previously been deduced from site-directed mutagenesis studies (15). Formation of a covalent complex between the nucleophilic serine residue and the substrate (the acyl-enzyme intermediate) is an essential step en route to peptide bond cleavage by non-Ab serine proteases (16). Phosphonate diesters, like the classical inhibitor DFP, can bind the active site of non-Ab serine proteases and serine esterases covalently (17–19).

In comparison, negatively phosphonate monoesters have traditionally been assumed to bind esterolytic Abs (20,21) and non-Ab serine esterases (22) via noncovalent electrostatic interactions. The aim of the present study was to characterize the reactivity of recombinant proteolytic Abs with phosphonate diesters and monoesters. Irreversible, active-site directed inhibition of catalytic activity by the phosphonate diesters was evident, stable Ab-phosphonate ester adducts were resolved under denaturing conditions; and, the catalytic activity was enriched by chemical selection of phage displayed Ab libraries on immobilized phosphonate esters. Although less potent, a phosphonate monoester displayed a reactivity profile similar to the diester, suggesting that Ab covalency contributes to the monoester binding. These observations help establish the serine protease character of natural Ab catalysts, offer a means towards isolation of efficient catalysts, and offer an explanation for unexpected catalytic mechanisms encountered in the case of certain esterase Abs raised by immunization with phosphonate monoesters.

Experimental Methods

Phosphonate esters: The asymmetric diester I (FIG. 8) was prepared in two steps: condensation of phenylphosphinic acid and tropine by means of icyclohexylcarbodiimide in dichloromethane and the subsequent oxidation in the presence of p-nitrophenol and triethylamine (18,19). Biotinylated diester II was prepared from compound I by alkylation with iodoacetyl-LC-biotin (Pierce) in DMF at 60° C. for 4 h. Monoester III was prepared from Sulfo-NHS-SS-biotin (Pierce) and phenyl amino(4-amidinophenyl) methanephosphonate. Diester IV was prepared from biotin disulfide N-hydroxysuccinimide ester (Sigma) and diphenyl amino(4-amidinophenyl)methanephosphonate. All products were purified by RP-HPLC and characterized by $_1$H-NMR and electrospray ionization mass spectrometry. Stock solutions of the compounds were in 30% acetonitrile.

Peptidase assay: Synthetic VIP (HSDAVFTDNYTRLRKQMAVK KYLNSILN-NH2 (SEQ ID NO: 3); Bachem, Torrance, Calif.) was radiolabeled with 125 I and (Tyr 10–125 I)VIP was separated by RP-HPLC (23). Hydrolysis of (Tyr 10–125 I)VIP treated with Abs was determined and corrected for background radioactivity in the absence of catalyst (3–15% of available radioactivity) (24). Preliminary assays showed the cleavage of (Tyr 10–125 I)VIP (0.2 nM) to be a linear function of catalyst concentration. Kinetic constants were computed by fitting rate data to the Michaelis-Menten equation $v=(Vmax.[S])/(Km+[S])$ (25). Cleavage of peptide-MCA conjugates (Peptides International) by antibody fragments was assayed fluorimetrically in 96-well plates (11). Background fluorescence of substrate in diluent was <10 FU. DFP and other protease inhibitors were from Sigma.

Recombinant Abs: Preparation of somatically matured L chain clone c23.5 (15; GenBank accession 896288), germline L chain clone c23.5 (12), L chain clone hk14 (25; GenBank accession 1850134) and the single chain Fv clone mRT3 (26) has been described. Unless otherwise specified, data reported here are for the mature L chain c23.5. Standard methods (25–27) were applied to prepare these libraries: (a) human lupus L chains cloned in pCANTAB5his6 vector (from 3 patients); (b) human lupus single chain Fv constructs in pHEN2 (from 2 patients; vector kindly provided by Centre for Protein Engineering, MRC, England; patent WO9201047-A, GenBank accession 1926701); (c) L chains from a mouse immunized with VIP in pCANTAB5his6 [source details in ref. 28; sequence of 2 L chains from this library available in GenBank in (U4 and U16, accession AF329094 and AF329095, respectively]; and (d) single chain Fv constructs from mice immunized with the extracellular domain of epidermal growth factor receptor in pCANTAB5his6 (immunization method to be described elsewhere). The murine and human Fv libraries were cloned as VH-linker-VL [linker: (GGGGS)3] and VL-linker-VH [linker: SS(GGGGS)2GGSA)] constructs, respectively. Both Fv orientations support antigen-binding (25,29)]. Following hypotonic lysis of erythrocytes in murine splenocytes ($2\times10^7$ cells) or peripheral blood leukocytes (from 100 ml blood), total RNA was isolated, a cDNA copy prepared using forward primers, and the cDNA for full-length L chains and the VH, Vκ, and Vλ domains was prepared by PCR (corresponding to residues 1-214; 1-123; 1-107; and, 1-107, respectively; Kabat numbering). Mouse Fv primers are described by Pharmacia (Recombinant Antibody Manual).

Primers for remaining libraries are:

(a) Human full-length L chain: VLK back (Sfi 1 site underlined)—
GTCCTCGCAACTGC GGCCCAGCCGGCCATGGCCGACATCCAGATGACC CAGTCTCC (SEQ ID NO: 4),
GTCCTCGCAACTGC GGCCCAGCCGGCCATGGCCGATGTTGTGATGAC TCAGTCTCC (SEQ ID NO: 5),
GTCCTCGCAACTGC GGCCCAGCCGGCCATGGCCGAAATTGTGTTGA CGCAGTCTCC (SEQ ID NO: 6),
GTCCTCGCAACTGC GGCCCAGCCGGCCATGGCCGACATCGTGATGA CCCAGTCTCC (SEQ ID NO: 7),
GTCCTCGCAACTGC GGCCCAGCCGGCCATGGCCGAAACGACACTCA CGCAGTCTCC (SEQ ID NO: 8),
GTCCTCGCAACTGC GGCCCAGCCGGCCATGGCCGAAATTGTGCTGA CTCAGTCTCC (SEQ ID NO: 9),
Ck forward (Not I site underlined)—
CCATCCT GCGGCCGCACACTCTCCCCTGTTGAAGCTCTT (SEQ ID NO: 10);

(b) Human single chain Fv: VLk back B see back primers, full-length L chain; VLk forward (Xho I site underlined) B
GCCTGAACCGCCTCCACCA CTCGAGCGTTTGATTTCCACCTTGGTCCC (SEQ ID NO:11),
GCCTGAACCGCCTCCACCA CTCGAGCGTTTGATCTCCAGCTTGGTCCC(SEQ ID NO: 12),
GCCTGAACCGCCTCCACCA CTCGAGCGTTTGATATCCACTTTGGTCCC (SEQ ID NO: 13),
GCCTGAACCGCCTCCACCA CTCGAGCGTTTGATCTCCACCTTGGTCCC (SEQ ID NO: 14),
GCCTGAACCGCCTCCACCA CTCGAGCGTTTAATCTCCAGTCGTGTCCC (SEQ ID NO: 15);
VLk back (Sfi I site underlined) B
GTCCTCGCAACTGC GGCCCAGCCGGCCATGGCCCAGTCTGTGTTGA CGCAGCCGCC (SEQ ID NO: 16),
GTCCTCGCAACTGC GGCCCAGCCGGCCATGGCCCAGTCTGCCCTGA CTCAGCCTGC (SEQ ID NO: 17),
GTCCTCGCAACTGC GGCCCAGCCGGCCATGGCCTCCTATGTGCTGA CTCAGCCACC (SEQ ID NO: 18),
GTCCTCGCAACTGC GGCCCAGCCGGCCATGGCCTCTTCTGAGCTGA CTCAGGACCC (SEQ ID NO: 19), GTCCTCGCAACTGC
GGCCCAGCCGGCCATGGCCCACGTTATACTGA
CTCAACCGCC (SEQ ID NO: 20),
GTCCTCGCAACTGC
GGCCCAGCCGGCCATGGCCCAGGCTGTGCTCA
CTCAGCCGTC (SEQ ID NO: 21),
GTCCTCGCAACTGC
GGCCCAGCCGGCCATGGCCAATTTTATGCTGA
CTCAGCCCCA (SEQ ID NO: 22);
VLk forward (Xho I underlined) B
GCCTGAACCGCCTCCACCA
CTCGAGCCTAGGACGGTGACCTTGGTCCC (SEQ ID NO: 23),
GCCTGAACCGCCTCCACCA
CTCGAGCCTAGGACGGTCAGCTTGGT CCC (SEQ ID NO: 24),
GCCTGAACCGCCTCCACCA
CTCGAGCCTAAAACGGTGAGCTGGGTCCC (SEQ ID NO: 25);
CL_forward B
TGAAGATTCTGTAGGGGCCACTGTCTT (SEQ ID NO: 26);
VH back (ApaL site underlined) B
CATGACCACA
GTGCACTTCAGGTGCAGCTGGTGCAGTCTGG
(SEQ ID NO: 27),
CATGACCACAGTGCACTTCAGGTCAACT-
TAAGGGAGTCTGG (SEQ ID NO: 28),
CATGACCACA
GTGCACTTGAGGTGCAGCTGGTGGAGTCTGG
(SEQ ID NO: 29),
CATGACCACAGTGCACTTCAGGTG-
CAGCTGCAGGAGTCGGG (SEQ ID NO: 30),
CATGACCACA
GTGCACTTCAGGTGCAGCTGTTGCAGTCTGC
(SEQ ID NO: 31),
CATGACCACAGTGCACTTCAGGTA-
CAGCTGCAGCAGTCAGG (SEQ NO: 32);
VH forward (Not I site underlined) B
GAGTCATTCT
GCGGCCGCGGGGAAGATGGGCCCTTGGT (SEQ ID NO: 33),
GAGTCATTCTGCGGCCGCGGG-
GAAAAGGGTTGGGGCGGATGC (SEQ ID NO: 34);
(c) Mouse full-length L chain: VLk back (Sfi I site underlined) B
GTCCTCGCAACTGC
GGCCCAGCCGGCCATGGCCGATGTTTTGATGA
CCCAAACTCCA (SEQ ID NO: 35),
GTCCTCGCAACTGC
GGCCCAGCCGGCCATGGCCGATATTGTGATAA
CCCAGGATGAA (SEQ ID NO: 36),
GTCCTCGCAACTGC
GGCCCAGCCGGCCATGGCCGACATTGTGCTRA
CCCAGTCTCCA (SEQ ID NO: 37),
GTCCTCGCAACTGC
GGCCCAGCCGGCCATGGCCGACATCCAGATGA
CNCAGTCTCCA (SEQ ID NO: 38),
GTCCTCGCAACTGC
GGCCCAGCCGGCCATGGCCCAAATTGTTCTCA
CCCAGTCTCCA (SEQ ID NO: 39),
GTCCTCGCAACTGC
GGCCCAGCCGGCCATGGCCGAAAATGTGCTCA
CCCAGTCTCCA (SEQ ID NO: 40);
C_forward (Not I site underlined) B
GAGTCATTCT
GCGGCCGCCTCATTCCTGTTGAAGCTCTTGAC
(SEQ ID NO: 41)

Linkage of mouse VL/VH domains was according to Pharmacia. Cloning of human Fv library in pHEN2 was by a two-step procedure—VH cDNA insertion via the ApaLI/NotI sites, and VL cDNA insertion via the SfiI/XhoI sites. Library sizes were—murine L chain, $1.2 \times 10^5$; murine Fv, $3.3 \times 10^7$; human L chain, $1.2 \times 10^6$; human Fv, $1.4 \times 10^7$. Randomly picked clones (at least five from each library) were sequenced by the dideoxy nucleotide sequencing method; 100, 75, 100 and 60% of the clones, respectively, contained full-length, stop codon-free, non-identical sequences.

Phage selection and Ab purification: Phage particles displaying Ab fragments as g3 fusion proteins ($2-5 \times 10^{13}$ CFU) treated with biotinlyated phosphonate esters (100 μl binding buffer, 50 mM sodiumphosphate, pH 8.0; 30 min, 37° C.) were precipitated with PEG (30) and adsorbed (60 min) on streptavidin coated Immunotubes (2 μg/tube, blocked with 5% BSA). The tubes were washed 4x with binding buffer containing 0.05% Tween-20 and 0.5 M NaCl; 4x with 0.1 M glycine-HCl, pH 2.7, 0.05% Tween-20; and 2x with binding buffer containing 0.05% Tween-20. Bound phages were eluted with 20 mM 2-PAM (24 hours, 25° C.) or 10 mM 2-mercaptoethanol (30 min, 25° C.) in 50 mM sodium phosphate, pH 8.0, respectively. Soluble Ab fragments in the periplasmic extracts of HB2151 cells were quantified by dot-blotting for the c-myc tag (30; expression level 0.4–6 mg/liter). Purification was by IMAC (31). For initial screening, the extracts (0.6 ml) were dialyzed against the column binding buffer and subjected to one round of IMAC (Bio-Spin columns, BioRad; 50 μl Ni-NTA agarose gel, Qiagen; elution with 0.25 ml pH 5 buffer). Large scale purifications from 250 ml cultures were carried out by two IMAC rounds.

SDS-gel electrophoresis (Phast gels 8–25%) showed a major 27 kD silver stained recombinant protein that was immunoblottable with anti-c-myc antibody (corresponding to Fv and L chain monomers). Some preparations contained a minor 55 kD dimer band and a 17 kD C-terminal fragment of the recombinant proteins, both of which were stained with anti-c-myc antibody (the fragment contains the C-terminal metal binding poly(his) tag and copurifies with the full-length proteins, ref 15). Non-denaturing gel filtration (2) of purified Ab fragments yielded the proteins as a major 27–28 kD peak with peptidase activity essentially identical to the preparations loaded on the column. In the case of clone YZ17 Fv, higher order aggregation was evident in preparations purified by IMAC. Further purification was by anion exchange chromatography on a Mono-Q column (Pharmacia; 0–0.5 M NaCl, 30 min), yielding an electrophoretically homogeneous 27–28 kD Fv fraction eluting at 0.37M NaCl.

Phosphonate ester-Ab binding: Complex formation was monitored by gel filtration (Superose-12 column, Pharmacia; 0.5 ml/min in 50 mM Tris-HCl, 100 mM glycine, pH 8, 0.15 M NaCl, 0.025% Tween-20, 0.02% sodium azide). The column was calibrated with thyroglobulin, IgG, albumin, ovalbumin and ribonuclease (Pharmacia). ELISA for bound phosphonate ester was incubation of column fractions in streptavidin coated 96-well plates (60 min, 37° C., React-Bind™; blocked with Blocker™ SA, Pierce). Unbound protein was removed by washing with 0.1 M sodium phosphate, pH 7.4, 0.1% BSA, 0.025% Tween-20 (PBS-T), and adducts were quantified using mouse anti-c-myc (60 min; 100 μl, 1:500 ascites fluid from hybridoma 9EI0, ATCC) and peroxidase conjugated goat anti-mouse IgG ($f_{Fc}$ specific, 1:1000; Sigma) (30). Phosphonate ester binding data reported here are for the monomer protein fraction recovered by gel filtration. The binding was also determined by a dot blot method after separating adducts and free phosphonate esters by gel filtration (Biospin 6 columns, BioRad, exclusion limit 6 kD). The excluded fraction (50 μl) was allowed to pass through a nitrocellulose membrane (0.2 μm; Trans-Blot; Biorad) using a 96-well blotting apparatus (Biorad), the membrane blocked with 5% nonfat milk, treated with peroxidase conjugated streptavidin (1:1000, Sigma) in PBS-T, and bound phosphonate esters determined using an electrochemiluminscence kit (Amersharn-Pharmacia) and X-OMAT film (Kodak). For SDS-polyacrylamide gel electrophoresis (4–20% gels), the Ab fragments were incubated with phosphonate esters (30 min), the complexes recovered by precipitation with 10% TCA, the pellets redissolved in electrophoresis buffer containing 2% SDS and 5 mM 2-mercaptoethanol, boiled for 2 min and subjected to electrophoresis. The gels were electroblotted onto nitrocellulose membranes (Transblot; Biorad), the blots treated overnight with 5% nonfat milk in PBS-T, washed with PBS-T, and biotinylated bands detected as described for the dot blots.

Results

Figure 11A:
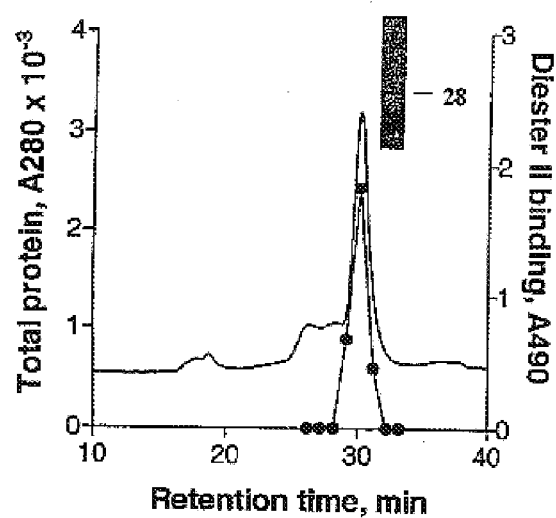
Figure 11B:
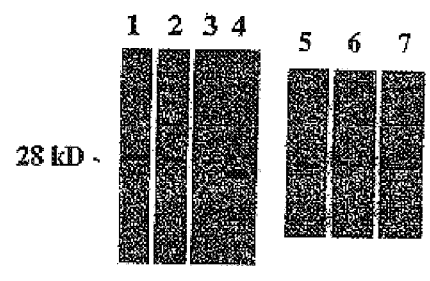
Figure 11C:
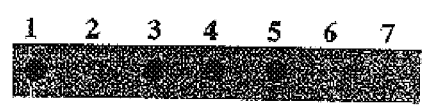

Phosphonate diester reactivity of Abs. VIP cleavage by anti-VIP L chain clones hk14 and c23.5 (germline and somatically matured proteins) has been described (12,15, 27). In initial studies, additional proteolytic Ab fragments were identified to study the inhibitory effect of DFP and phosphonate diester II (FIG. 8). Nineteen randomly picked L chain clones (from a mouse immunized with VIP, U series clones) and an Fv clone isolated by McAfferty and coworkers by binding of phage Abs to a phosphonate monoester (mRT3, ref 26) were screened for VIP cleaving activity. Seven L chains and the Fv displayed ($Tyr_{10}-_{125}I$)VIP cleaving activity (>10% cleavage; catalyst concentration 20 nM). Confirmation of the peptidase activity as belonging to the Ab fragments was based on the observed electrophoretic homogeneity of the catalysts, elution of the activity in the 27–28 kD light chain monomers purified by gel filtration (2), and the absence of detectable peptidase activity in equivalently purified extracts from several L chain clones (e.g., clone U21) and extracts from bacteria containing the control vector (no Ab insert). DFP and diester II at concentrations of 1 mM and 0.1 mM, respectively, inhibited the catalytic activity of every Ab fragment analyzed by at least 40% (n=11 and 6 clones, respectively). See FIG. 9. Near-equivalent inhibition of the activities of the germline and mature forms of L chain c23.5 by II was observed. The inhibitory effect was relieved to varying extent at 5-fold lower DFP and II concentrations in every case. Inhibition was also evident using a peptide-MCA substrate [83, 71, 92 and 79% inhibition of cleavage of PFR-MCA (200 μM) by II (50 μM) using as catalysts L chain c23.5, L chain hk14, Fv mRT3 and L chain U16; catalyst concentration 0.5 μM]. Removal of free II from the Ab reaction mixture by gel filtration did not restore the catalytic activity, suggesting that the inhibition was irreversible (FIG. 10). The substrate (VIP) protected against II inhibition of catalytic activity. II contains a biotin tag, permitting determination of its its binding to the Ab fragments with a streptavidin-peroxidase conjugate. II-labeled Fv was resolved by gel filtration (Superose-12 column) as a biotin-containing 27–28 kD peak coeluting with the A280 optical density peaks of Fv monomers (FIG. 11A). Inclusion of excess I in the reaction mixture (10 mM; I is the nonbiotinylated form of II) inhibited the labeling by >90%. Essentially similar results were observed by gel filtration of II-containing adducts of L chain clones c23.5, hk14 and U16 (labeling of the monomer L chains was at 18, 33 and 51% of the Fv level in FIG. 11, respectively). SDS-electrophoresis of reaction mixtures followed by staining with streptavidin-peroxidase permitted identification of II-Ab fragment adducts at the correct mass corresponding to the Fv and L chain monomers (FIG. 11B). II binding by the Fv was reduced in the presence of the substrate (FIG. 11C). Control extracts of bacteria harboring vector without an Ab insert did not bind II. These observations indicate irreversible, active site-directed II binding by the Ab fragments.

Figure 12B:
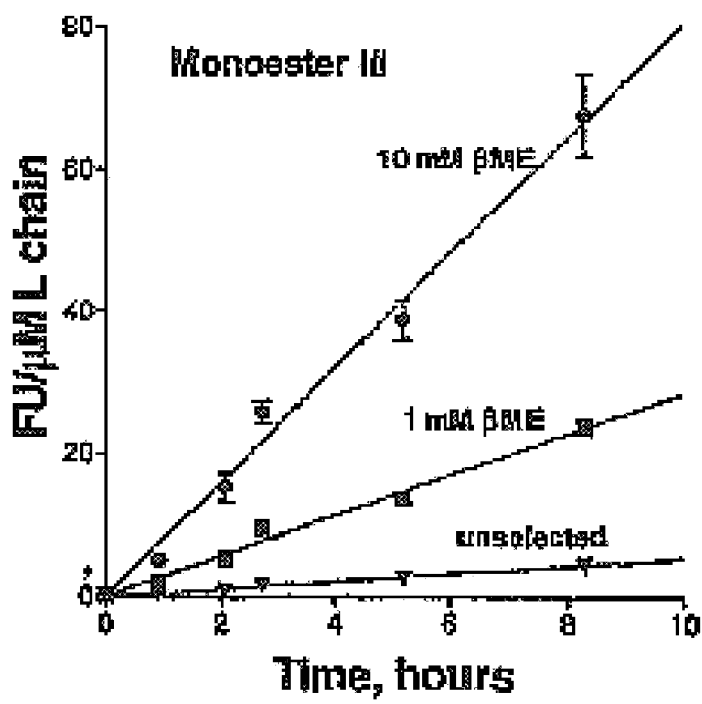

Covalent phage selection. A compound similar to diester II is described to permit isolation of catalytically active subtilisin mutants from a phage library (32). Monoester III-like compounds are generally thought bind esterolytic Abs by noncovalent electrostatic interactions (20,21). However, Fv mRT3, which had been initially identified based on binding to a phosphonate monoester (26), also displayed the ability to bind diester II irreversibly (FIG. 11). Therefore, both diester II and monoester III were analyzed for the ability to capture phage displayed catalytic Abs. II- and III-phage Ab complexes are trapped on immobilized streptavidin via the biotin tag. Noncovalently bound phages were removed by exhaustive washing at pH 2.7 (and additional pH 12 washes with 0.1 M triethylamine in the case of selection with monoester III). Elution of II-bound phages was by treatment with 2-PAM, which is described to cleave the P-O bind in DFP-serine esterase adducts (33), and of III-bound phages, by reduction of the S—S bond in III. The Ab fragments encoded by selected phagemid DNA were expressed in soluble form, purified by IMAC and analyzed for catalytic activity along with the control unselected Abs. To determine selection efficacy, cleavage of the model substrate PFR-MCA was measured at equivalent concentrations of polyclonal selected and unselected Ab fragments (FIG. 12). About 10–40 fold enrichment of the PFR-MCA cleaving activity was evident in the selected Abs from the human lupus L chain, human lupus Fv and murine Fv libraries. Increasing levels of catalytic activity were evident as a function of increasing length of elution of II-bound phages with PAM (20 and 70 FU/16 h/μM lupus light chains following elution for 3 and 24 hours, respectively) and increasing concentration of 2-mercaptoethanol applied for elution of III-bound phages (FIG. 12B). Essentially similar levels of catalyst enrichment were evident in the selected Ab populations using VIP as substrate (not shown). II-selected L chains displayed increased II binding (by 11-fold) compared to unselected L chains, analyzed by gel filtration and detection of adducts by ELISA as in FIG. 9. Taken together, these studies demonstrate the ability of diester 11 and monoester III to preferentially bind the catalyst subset present in the phage Abs.

Individual catalytic Fv and L chains from the selected populations were identified by screening for peptidase activity. Sixty percent of III-selected Fv clones and 69% of II-selected L chain clones displayed PFR-MCA cleaving activity >2 FU/h/μM above the background level (activity of equivalently purified periplasmic extracts from bacteria harboring vector without an Ab insert; substrate 200 μM). Preferential cleavage of peptide-MCA substrates on the C terminal side of a basic residue (Arg) by a II-selected light chain (clone GG63) and a III-selected Fv (clone YZ17) was evident (FIG. 13). Cleavage of substrates containing MCA linked to acidic or neutral residues was undetectable. Saturation kinetics consistent with the Michaelis-Menten-Henri equation were observed for both clones using their preferred peptide-MCA substrates (YZ17 Fv, EAR-MCA; GG63 L chain, PFR-MCA; Table 1). DFP inhibited the proteolytic activity of both Ab fragments, confirming the mechanistic class of the catalysts (Table 1). Inhibitors of other protease classes did not influence the reaction detectably (iodoacetamide, phenanthroline, pepstatin A). Interestingly, diester IV inhibited the catalytic activity of Fv YZ17 more potently than monoester III Fv YZ17 Fv, even though this clone had been isolated by binding the monoester (FIG. 14). Moreover, Fv YZ17 was stained strongly by diester IV assessed by SDS-electrophoresis, whereas staining with monoester III was barely visible (FIG. 15). L chain GG63, which had been isolated by binding to diester II was also stained more strongly by diester IV compared monoester III. SDS-electrophoresis of a crude periplasmic extract of Fv clone YZ17 treated with diester II revealed a single biotinylated band corresponding to 27–28 kD Fv. Other periplasmic proteins in the extract were not stained, and staining of periplasmic proteins in a control extract of bacteria harboring vector without an antibody insert was not evident. It may be concluded that phosphonate diesters and monoesters bind the proteolytic Abs irreversibly, with the monoester displaying a lower level of reactivity.

According to their cDNA sequences, light chain clone belongs to family 1, subgroup I (Kabat database). The VL and VH domains of Fv cone YZ17 (GenBank AF329093, Appendix 2) belong to family XXVI, subgroup V and subgroup I, respectively (VH family designated 'Miscellaneous' in Kabat database). The VL domains of GG63 and YZ17 contain 17 and 2 amino acid substitutions compared to their germline gene counterparts, respectively (GenBank accession numbers 33197 and 5305062, respectively). The germline counterpart of YZ17 VH domain could not be determined with certainty.

TABLE I

| Catalyst | $K_m$, µM | $k_{cat}$, $min_{-1}$ | Inhibition, % | | | |
|---|---|---|---|---|---|---|
| | | | DFP | Phenan-throline | Iodo-acetamide | Pepstatin A |
| Fv YZ17 | 10.1 (1.2) | 0.5 (0.09) | 84.6 (3.3) | 0.2 (2.3) | 4.4 (3.1) | 1.2 (2.9) |
| L chain GG63 | 7.9 (2.4) | 0.2 (0.05) | 74.4 (0.1) | 0.6 (0.7) | 5.8 (4.5) | 0.2 (1.3) |

Table 1: Apparent kinetic constants and inhibition profile of CRAA-selected antibody fragments. Substrate, EAR-MCA (YZ17 Fv) and PFR-MCA (GG63 light chain). Values in parentheses, standard deviation. Rate data at increasing substrate concentration (2.5, 5, 10, 20, 40, 80, 160 Mm) were gathered over 7 hours and fitted to the Michaelis-Menten equation. Reaction conditions 7 hours, 37° C. Inhibition was assayed by preincubation of catalysts with various protease inhibitor # (30 min, 37° C.), addition of substrate to 200 µM, and measurement of reaction rate over 5 hours. DFP 0.5 mM; phenanthroline 10 mM; iodacetamide 0.5 mM; pepstatin A 10 µM. Fv YZ17 40 nM. L chain GG63 80 nM. Inhibition data are expressed as percent of fluorescence in the absence of inhibitor (Fv YZ17, 93 FU; L chain GG63, 71 FU).

Discussion

Formation of the tetrahedral transition state of peptide bond cleavage by non-Ab serine proteases involves covalent attack by the active site nucleophile and transfer of a negative charge to the carbonyl oxygen in the substrate. The phosphonate diester group mimics the substrate carbonyl, and the phosphorous atom is sufficiently electrophilic to permit covalent binding to the active site of serine proteases (18,19). Phosphonate diesters have recently been applied to isolate mutants of a non-Ab serine protease (subtilisin) displayed on a a phage display library (32). A positive charge was placed close to the phosphonate esters utilized as probes for proteolytic Abs in the present study, because most known proteolytic antibodies cleave peptide bonds on the C-terminal side of basic residues (3,5–8,31). In FIG. 9, identification of Ab fragments as proteases had been achieved without reliance on the mechanistic class of the catalysts (i.e., by binding to VIP, random screening for catalytic activity). Yet, the diester inhibited the proteolytic activity of all six Abs analyzed. The inhibition was irreversible and active site-directed. Formation of stable adducts of the phosphonate diester with proteolytic L chains and a Fv construct was evident by column chromatography and denaturing electrophoresis. Evidently, therefore, a serine protease-like mechanism is recurrently encountered in Abs expressing proteolytic activity. The phage selections confirmed this conclusion. As predicted, selection of the phages by binding to the diester enriched the proteolytic activity.

Results from phosphonate monoester studies presented in Example I offer interesting insights to certain aspects of Ab catalysis. McAfferty et al. (26) isolated Fv mRT3 by immunization and phage selection with a phosphonate monoester. This Fv was observed in the present study to bind diester II irreversibly and to express proteolytic activity. Phosphonate monoesters have previously been advanced as oxyanionic transition state analogs that bind catalytic Ab active sites solely by noncovalent means. [The electrophilicity of the monoesters is generally held to be too weak to permit covalent binding to the active site]. On the other hand, catalytic mechanisms that are not predicted from models of simple noncovalent binding interactions have been encountered in Abs following immunization with phosphonate monoesters (reviewed in ref 34), for instance an anti-monoester Ab with an apparently fortuitous serine esterase activity (35). In the present study, the utility of phosphonate monoesters in selecting proteolytic L chains and Fv has been confirmed directly, as is evident from the enriched catalytic activity of monoester III-selected Ab populations in FIG. 12. Remarkably, Fv clone YZ17 selected by binding to monoester III was even more reactive with the diester analog IV. Monoester III also formed stable adducts with a classical serine protease, trypsin, and it inhibited enzyme activity irreversibly. It may be concluded that the monoester can mimic the transition state of peptide bond hydrolysis by virtue of its covalent reactivity in addition to the oxyanionic character. These observations are not without precedent. A survey of the literature has identified two relevant reports. One describes the covalent reactivity of phosphonate monoesters with P-lactamase based on inspection of inhibition kinetics (36; this enzyme utilizes an active site serine nucleophile for catalysis). The second reports covalent binding of a phosphonic acid compound to a cholineesterase (37; phosphonic acid has two negative charges—its reactivity with active site nucleophiles is predicted to be even lower than the monoester). It appears safe to conclude, therefore, that covalent binding to the active site may, in part, underlie the ability of the phosphonate monoester to select proteolytic Abs from the libraries. The foregoing conclusions are not in conflict with an early report describing the failure to isolate Phe-Ile or Ile-Gly cleaving monoclonal IgG Abs from mice immunized with a phosphonate monoester (38). The catalysts identified in the present report display specificity for cleavage on the C terminal side of basic residues, which may account for lack of cleavage at peptide bonds linking neutral residues. Moreover, the methods applied in ref 38 were designed to identify Abs capable of noncovalent phosphonate monoester binding, whereas our phage selection protocols were biased to enrich covalently reactive Abs at the expense of noncovalent binders. There is also the issue of structural differences remote from the active site—ref 38 studied full-length IgG whereas recombinant single chain Fv and L chain subunits were analyzed in the present study. The catalytic characteristics of IgG, Fv and the L chain subunit can differ profoundly (28,31,39). Ab combining sites can be quite diverse because of the existence of multiple germline V genes and somatic mechanisms permitting sequence diversification of the V domains (V-J/V-D-J rearrangement; CDR hypermutability). Whether a single phosphonate ester structure can serve as an efficient binding reagent for proteolytic Abs with different substrate specificities depends on the extent of active site conservation. Synthetic peptides corresponding to antigen regions distant from the cleavage site can inhibit proteolytic Abs (40). Moreover, mutations that decrease binding to the antigen ground state do not decrease the rate of catalysis by an Ab L chain (15), suggesting the existence of distinct subsites responsible for the chemical reactivity and initial antigen binding (corresponding to the transition state and ground state stabilization steps, respectively). A comparatively conserved catalytic subsite may be compatible, therefore, with differing Ab specificities for individual antigens derived from distinct noncovalent interactions at the ground state binding subsite. This model is consistent with preservation of a germline-encoded catalytic subsite in the V domain over the course of B cell clonal selection, even as antigen binding affinity improves due to remote mutations. Note, however, that the chemical reactivity of active site nucleophiles is determined in part by intramolecular interactions, for instance, by formation of hydrogen bonds between Ser, His and Asp residues (16). Depending on the specific structural changes introduced by V domain sequence diversification, improvements or deteriorations of the catalytic machinery are feasible. The level of catalytic activity expressed by Abs may depend in part, therefore, upon the immunological history of the repertoires employed as the source of the phage libraries. In particular, the somatically mature repertoire in certain autoimmune and lymphoproliferative disorders frequently expresses Ab catalysts (6,8,41–43), and may be suitable for isolating Ab catalysts. The phage experiments in the present study were intended to study the phosphonate ester reactivity of Abs, as opposed to isolating the highest activity catalysts. Whether chemical isolation of medically useful catalysts is feasible will depend on further technological improvments. The turnover numbers for phosphonate ester-selected Fv YZ17 and L chain GG63 are greater than observed for proteolytic Ab fragments identified by random screening (9,10). More refined phage selection protocols may help identify high turnover, antigen-specific proteolytic Abs, e.g., repeated rounds of selection using phosphonate esters flanked by appropriate peptide sequences. The phosphonate esters could also be applied as immunogens to elicit the synthesis of serine protease-like Abs on demand, assuming that covalent antigen binding by Abs on the surface of B cells can drive clonal selection and Ab affinity maturation. A similar strategy has been previously been proposed to elicit the synthesis of aldolase Abs (44) The pitfall, of course, is that irreversible immunogen binding by B cells may tolerize the cells, as is believed to occur upon persistent occupancy of the B cell receptor by noncovalent immunogens (45).

GenBank Accession numbers and information for U4L chain, U16L chain, YZ17Fv and G63 L chain are provided below.

GenBank Accession No. and Information for U4L chain

```
AF329094.
Mus musculus dome...[gi:12751402]
LOCUS       AF329094              330 bp    mRNA    linear   ROD Jul. 24, 2001
DEFINITION Mus musculus domesticus U4 recombinant antibody light chain VL
     domain mRNA, partial cds.
ACCESSION   AF329094
VERSION     AF329094.1  GI:12751402
KEYWORDS
SOURCE  western European house mouse.
  ORGANISM Mus musculus domesticus
       Eukaryota; Metazoa; Chordata; Craniata; Vertebrata; Euteleostomi;
       Mammalia; Eutheria; Rodentia; Sciurognathi; Muridae; Murinae; Mus.
REFERENCE 1 (bases 1 to 330)
  AUTHORS Paul,S., Tramontano,A., Gololobov,G., Zhou, Y.X., Taguchi,H.,
      Karle,S., Nishiyama, Y., Planque,S. and George,S.
  TITLE  Phosphonate ester probes for proteolytic antibodies
  JOURNAL J. Biol. Chem. 276 (30), 28314–28320 (2001)
  MEDLINE 21359358
  PUBMED  11346653
REFERENCE 2 (bases 1 to 330)
  AUTHORS Paul,S., Zhou, Y.-X., Nishiyama, Y., Taguchi,H., Karle,S.,
      Gololobov,G., Planque,S., George,S. and Tramontano,A.
  TITLE  Direct Submission
  JOURNAL Submitted (Dec. 14, 2000) Pathology and Laboratory Medicine,
      University of Texas-Houston Medical School, 6431 Fannin, Houston,
      TX 77030, USA
FEATURES         Location/Qualifiers
   source       1..330
                /organism="Mus musculus domesticus"
                /strain="BALB/c"
                /sub_species="domesticus"
                /db_xref="taxon:10092"
                /clone="U4"
                /cell_type="B-lymphocyte"
                /tissue_type="hyperimmunized spleen"
                /dev_stage="young adult"
```

```
                            -continued
         /note="mice immunized with VIP-KLH conjugate"
CDS      <1..>330
         /codon_start=1
         /product="recombinant antibody light chain VL domain"
         /protein_id="AAK07643.1"
         /db_xref="GI:12751403"
```

/translation="DVLMTQSPLSLPVSLGDQASISCRSSQSIVHSNGNTYLEWYL

QKPGQSPKLLIYKVSNRFSGVPDRFSGSGSGTDFTLKISRVEAEDLGVYYC

FQGSHVPYTFGGGQTGK (SEQ ID NO: 42)"

BASE COUNT   87 a   79 c   79 g   85 t
ORIGIN 1 gatgttttga tgacccaatc tccactctcc ctgcctgtca gtcttggaga tcaagcctcc 61 atctcttgca gatctagtca gagcattgta catagtaatg gaaacaccta tttagaatgg 121 tacctgcaga aaccaggcca gtctccaaag ctcctgatct acaaagtttc caaccgattt 181 tctggggtcc cagacaggtt cagtggcagt ggatcaggga cagatttcac actcaagatc 241 agcagagtgg aggctgagga tctgggagtt tattactgct ttcaaggttc acatgttccg 301 tacacgttcg gaggggggcca aactggaaaa (SEQ ID NO: 43)

```
GenBank Accession number and information for U16 L chain
AF329095. Mus musculus dome...[gi:12751404]
LOCUS       AF329095               307 bp    mRNA    linear   ROD Jul. 24, 2001
DEFINITION Mus musculus domesticus U16 recombinant antibody light chain VL
           domain mRNA, partial cds.
ACCESSION  AF329095
VERSION    AF329095.1 GI:12751404
KEYWORDS
SOURCE     western European house mouse.
 ORGANISM Mus musculus domesticus
           Eukaryota; Metazoa; Chordata; Craniata; Vertebrata; Euteleostomi;
           Mammalia; Eutheria; Rodentia; Sciurognathi; Muridae; Murinae; Mus.
REFERENCE 1 (bases 1 to 307)
 AUTHORS Paul,S., Tramontano,A., Gololobov,G., Zhou, Y.X., Taguchi,H.,
           Karle,S., Nishiyama, Y., Planque,S. and George,S.
 TITLE   Phosphonate ester probes for proteolytic antibodies
 JOURNAL J. Biol. Chem. 276 (30), 28314-28320 (2001)
 MEDLINE 21359358
 PUBMED  11346653
REFERENCE 2 (bases 1 to 307)
 AUTHORS Paul,S., Zhou, Y.-X., Nishiyama, Y., Taguchi,H., Karle,S.,
           Gololobov,G., Planque,S., George,S. and Tramontano,A.
 TITLE   Direct Submission
 JOURNAL Submitted (Dec. 14, 2000) Pathology and Laboratory Medicine,
           University of Texas-Houston Medical School, 6431 Fannin, Houston,
           TX 77030, USA
FEATURES         Location/Qualifiers
   source   1..307
            /organism="Mus musculus domesticus"
            /strain="BALB/c"
            /sub_species="domesticus"
            /db_xref="taxon:10092"
            /clone="U16"
            /cell_type="B-lymphocyte"
            /tissue_type="hyperimmunized spleen"
            /dev_stage="young adult"
            /note="mice immunized with VIP-KLH conjugate"
   CDS      <1..>307
            /codon_start=1
            /product="recombinant antibody light chain VL domain"
            /protein_id="AAK07644.1"
            /db_xref="GI:12751405"
```

/tranlaslation="QNVLTQSPALMSASPGEKVTITCSASPSVSYMHWFQQKPGTS

PKLWIYSTSNLASGVPARFSGSGSGTSYSLTISRMEAEDAATYYCQQRSSY

PWTFGGAPS (SEQ ID NO: 44)"

BASE COUNT   74 a   90 c   72 g   71 t
ORIGIN

-continued

```
  1 caaaatgttc tcacccagtc tccagcactc atgtctgcat ctccagggga gaaggtcacc 61 ataacctgca gtgccagccc aagtgtaagt tacatgcact ggttccagca gaagccaggc 121 acttctccca aactctggat ttatagcaca tccaacctgg cttctggagt ccctgctcgc 181 ttcagtggca gtggatctgg gacctcttac tctctcacaa tcagccgaat ggaggctgaa 241 gatgctgcca cttattactg ccagcaaagg agtagttacc cgtggacgtt cggtggagca 301 ccaagct (SEQ ID NO: 45)
```

GenBank Accession Number and Information for YZ17 Fv
AF329093. Synthetic constru...[gi:12957377]

```
LOCUS       AF329093                 795 bp    mRNA       linear   SYN Jul. 24, 2001
DEFINITION  Synthetic construct recombinant single-chain Fv antibody mRNA,
            partial cds.
ACCESSION   AF329093
VERSION     AF329093.1  GI:12957377
KEYWORDS
SOURCE   synthetic construct.
 ORGANISM synthetic construct
    artifical sequence.
REFERENCE 1 (bases 1 to 795)
 AUTHORS   Paul,S., Tramontano,A., Gololobov,G., Zhou, Y.X., Taguchi,H.,
    Karle,S., Nishiyama, Y., Planque,S. and George,S.
 TITLE    Phosphonate ester probes for proteolytic antibodies
 JOURNAL  J. Biol. Chem. 276 (30), 28314-28320 (2001)
 MEDLINE  21359358
 PUBMED   11346653
REFERENCE 2 (bases 1 to 795)
 AUTHORS   Paul,S., Zhou, Y.-X., Nishiyama, Y., Taguchi,H., Karle,S.,
    Gololobov,G., Planque,S., George,S. and Tramontano,A.
 TITLE    Direct Submission
 JOURNAL  Submitted (Dec. 13, 2000) Pathology and Laboratory Medicine,
     University of Texas-Houston Medical School, 6431 Fannin, Houston,
     TX 77030, USA
FEATURES           Location/Qualifiers
  source    1..795
          /organism="synthetic construct"
          /db_xref="taxon:32630"
          /focus
   CDS      <1..795
          /codon_start=1
          /transl_table=11
          /product="recombinant single-chain Fv antibody"
          /protein_id="AAK09206.1"
          /db_xref="GI:12957378"
```

/translation="QVKLQQSGPELVKPGASVKISCKASGYTFTDYTMDWVKQS

HGKSLEWIGYIYPNNGGTGYNQKFKSKATLTVDKSSSTAYMELHSLTSED

SAVYYCARFSSFDYWGQGTTVTVSSGGGGSGGVGSGGGGSDIQMTQSPS

SLSASLGDTITITCHASQNINVWLSWYQQKPGNIPKLLIYRASNLHTGVPS

RFSGSGSGTGFTLTISSLQPEDIATYYCQQGQSYPLTFGTGTKLEIKRAAAH

HHHHHGAAEQKLISEEDLNGAA (SEQ ID NO: 46)"

```
  misc_feature 1..339
          /note="VH domain; Region: antibody heavy chain variable
          domain"
   source     1..714
          /organism="Mus musculus domesticus"
          /strain="MRL/Mp-lpr"
          /sub_species="domesticus"
          /db_xref="taxon:10092"
          /clone="YZ-17"
          /cell_type="B-lymphocyte"
          /tissue_type="hyperimmunized spleen"
          /dev_stage="young adult"
          /note="selection with Bt-Z monoester from mouse library
          immunized with exEGFR"
  misc_feature 340..390
          /note="Region: linker between VH and VL domains"
  misc_feature 391..714
          /note="VL domain; Region: antibody light chain variable
          domain"
```

```
                                         -continued
    misc_feature   724..741
           /note="Region: poly-histidine tag"
    misc_feature   751..783
           /note="Region: c-myc tag"
BASE COUNT       213 a    205 c    199 g    178 t
ORIGIN 1 caggtgaaac tgcagcagtc aggacctgaa ctggtgaagc tggggcttc agtgaagata 61 tcctgcaagg cttctggtta cacattcact gactacacca tggactgggt gaagcagagc 121 catggaaaga gccttgagtg gattggatat atttatccta acaatggtgg tactggctac 181 aaccagaagt tcaagagcaa ggccacattg actgtagaca agtcctccag cacagcctac 241 atggagctcc acagcctgac atctgaggac tctgcagtct attactgtgc aagattttcc 301 tcttttgact actggggcca agggaccacg gtcaccgtct cctcaggtgg aggcggttca 361 ggcggagttg gctctggcgg tggcggatcg gacatccaga tgactcagtc tccatccagt 421 ctgtctgcat cccttggaga cacaattacc atcacttgcc atgccagtca gaacattaat 481 gtttggttaa gctggtacca gcagaaacca ggaaatattc ctaaactatt gatctatagg 541 gcttccaact tgcacacagg cgtcccatca aggtttagtg gcagtggatc tggaacaggt 601 ttcacattaa ccatcagcag cctgcagcct gaagacattg ccacttacta ctgtcaacag 661 ggtcaaagtt atcctctcac gttcggcacg ggcaccaagc tggaaatcaa acgggcggcc 721 gcacatcatc atcaccatca cggggccgca gaacaaaaac tcatctcaga agaggatctg 781 aatggggccg catag (SEQ ID NO: 47)
```

GenBank Accession Number and Information for G63 L chain
AF352557. *Homo sapiens* GG-6...[gi:13549147]
LOCUS     AF352557              339 bp    mRNA    linear   PRI Jul. 24, 2001
DEFINITION *Homo Sapiens* GG-63 immunoglobulin light chain variable region mRNA,
     partial cds.
ACCESSION AF352557
VERSION   AF352557.1 GI:13549147
KEYWORDS  
SOURCE    human
 ORGANISM *Homo sapiens*
     Eukaryota; Metazoa; Chordata; Craniata; Vertebrata; Euteleostomi;
     Mammalia; Eutheria; Primates; Catarrhini; Hominidae; Homo.
REFERENCE 1 (bases 1 to 339)
 AUTHORS  Paul,S., Tramontano,A., Gololobov,G., Zhou, Y.X., Taguchi,H.,
    Karle,S., Nishiyama, Y., Planque,S. and George,S.
 TITLE    Phosphonate ester probes for proteolytic antibodies
 JOURNAL  J. Biol. Chem. 276 (30), 28314-28320 (2001)
 MEDLINE  21359358
 PUBMED   11346653
REFERENCE 2 (bases 1 to 339)
 AUTHORS  Paul,S., Zhou, Y.-X., Nishiyama, Y., Taguchi,H., Karle,S.,
    Gololobov,G., Planque,S., George,S. and Tramontano,A.
 TITLE    Direct Submission
 JOURNAL  Submitted (Feb. 22, 2001) Pathology and Laboratory Medicine,
     University of Texas-Houston Medical School, 6431 Fannin, Houston,
     TX 77030, USA
FEATURES         Location/Qualifiers
  source   1..339
           /organism="*Homo sapiens*"
           /db_xref="taxon:9606"
           /clone="GG-63"
           /cell_type="peripheral blood lymphocyte"
           /dev_stage="adult"
  CDS      <1..>339
           /note="selected on Bt-X (phenylphosphonate 4-nitrophenyl
           [N-(6-biotinylhexanediamin-1-yl)carboxymethyl]tropan-3-ol
           diester)"
           /codon_start=1
           /product="immunoglobulin light chain variable region"
           /protein_id="AAK29667.1"
           /db_xref="GI:13549148"

/translation="DIQMTQSPSTLSASVGDTVTIACRASQSINGYLAWYQQKPGK

APNLLIFKASTLQSGVPSRFSGSGYAREFTLTISSLQPDDFATYYCQQYYT

```
                              -continued
HSRTFGQGTQVEITRTVAAP (SEQ ID NO: 48)"

BASE COUNT    85 a   98 c   79 g   77 t

ORIGIN 1 gacatccaga tgacccagtc tccttccacc ctgtctgcat ctgtgggaga cacagtcacc 61 atcgcttgcc gggccagtca gagtattaat ggctacttgg cctggtatca gcagaaacct 121 gggaaagccc ctaacctcct gatctttaag gcatctactt tacaaagtgg ggtcccatca 181 aggttcagcg gcagtggata tgcgagagaa ttcacgctca ccatcagcag cctgcagcct 241 gatgattttg caacttatta ctgccaacag tattatactc actcccggac gttcggccaa 301 gggaccagg tggaaatcac acgaactgtg gctgcacca   (SEQ ID NO: 49)
```

REFERENCES FOR EXAMPLE II

1. Paul, S., Volle, D. J., Beach, C. M., Johnson, D. R., Powell, M. J., and Massey, R. J. (1989) *Science.* 244, 1158–1162
2. Sun, M., Mody, B., Eklund, S. H., and Paul, S. (1991) *J. Biol. Chem.* 266, 15571–15574
3. Hifumi, E., Okamoto, Y., and Uda, T. (1999) *J. Biosci. Bioengin.* 88, 323–327
4. Paul, S., Kalaga, R., Gololobov, G., and Brenneman, D. (2000) *Appl. Biochem. Biotech.* 83, 71–84
5. Matsuura, K., and Sinohara, H. (1996) *Biol. Chem.* 377, 587–589
6. Li, L., Paul, S., Tyutyulkova, S., Kazatchkine, M., and Kaveri, S. (1995) *J. Immunol.* 154, 3328–3332
7. Lacroix-Desmazes, S., Moreau, A., Sooryanarayana, Bonnemain, C., Stieltjes, N., Pashov, A., Sultan, Y., Hoebeke, J., Kazatchkine, M. D., and Kaveri, S. V. (1999) *Nat. Med.* 5, 1044–1047
8. Thiagarajan, P., Dannenbring, R., Matsuura, K., Tramontano, A., Gololobov, G., and Paul, S. (2000) *Biochemistry* 39,6459–6565
9. Matsuura, K., Yamamoto, K., and Sinohara, H. (1994) *Biochem. Biophys. Res. Commun.* 204, 57–62
10. Paul, S., Li, L., Kalaga, R., Wilkins-Stevens, P., Stevens, F. J., and Solomon, A. (1995) *J. Biol. Chem.* 270, 15257–15261
11. Kalaga, R., Li, L., O'Dell, J., and Paul, S. (1995) S. *J. Immunol.* 155, 2695–2702
12. Gololobov, G., Sun, M., and Paul, S. (1999) *Mol. Immunol.* 36, 1215–1222
13. Liu, E., Prasad, L., Delbaere, L. T., Waygood, E. B., and Lee, J. S. (1998) *Mol. Immunol.* 35, 1069–1077
14. Baldwin, E., and Schultz, P. G. (1989) *Science* 245, 1104–1107
15. Gao, Q.-S., Sun, M., Rees, A., and Paul, S. (1995) *J. Mol. Biol.* 253, 658–664
16. Schowen, R. L. (1988) *Mechanistic principles of enzyme activity,* 119–164
17. Harel, M., Su, C. T., Frolow, F., Ashani, Y., Silman, I., and Sussman, J. L. (1991) *J. Mol. Biol.* 221, 909–918
18. Bone, R., Sampson, N. S., Bartlett, P. A., and Agard, D. A. (1991) *Biochemistry* 30, 2263–2272
19. Sampson, N. S., and Bartlett, P. A. (1991) *Biochemistry* 30, 2255–2263
20. Tramontano, A., Janda, K. D., and Lerner, R. A. (1986) *Proc. Natl. Acad. Sci. USA* 83, 6736–6740
21. Charbonnier, J. B., Golinelli-Pimpaneau, B., Gigant, B., Tawfik, D. S., Chap, R., Schindler, D. G., Kim, S. H., Green, B. S., Eshhar, Z., and Knossow, M. (1997) *Science* 275, 1140–1142
22. Bencsura, A., Enyedy, I., and Kovach, I. M. (1995) *Biochemistry* 34, 8989–8999
23. Mody, R. K., Tramontano, A., and Paul, S. (1994) *Int. J. Pept. Prot. Res.* 44, 441–447
24. Paul, S., Sun, M., Mody, R., Eklund, S. H., Beach, C. M., Massey, R. J., and Hamel, F. (1991) *J. Biol. Chem.* 256, 16128–16134
25. Clackson, T., Hoogenboom, H. R., Griffiths, A. D., and Winter, G. (1991) *Nature* 352, 624–628
26. McCafferty, J., Fitzgerald, K. J., Earnshaw, J., Chiswell, D. J., Link, J., Smith, R., Kenten, J. (1994) *Appl. Biochem. Biotechnol.* 47, 157–173
27. Tyutyulkova, S., Gao, Q.-S., Thompson, A., Rennard, S., and Paul, S. (1996) *Biochimica. Biophysica. Acta.* 1316, 217–223
28. Paul, S., Sun, M., Mody, R., Tewary, H. K., Stemmer, P., Massey, R. J., Gianferrara, T., Mehrotra, S., Dreyer, T., Meldal, M. (1992) *J. Biol. Chem.* 267, 13142–13145
29. Anand, N. N., Mandal, S., MacKenzie, C. R., Sadowska, J., Sigurskjold, B., Young, N. M., Bundle, D. R., and Narang, S. A. (1991) *J. Biol. Chem.* 266, 21874–21879
30. Tyutyulkova, S., Gao, Q.-S., and Paul, S. (1995) *Antibody Engineering Protocols* 51, 377–394
31. Sun, M., Gao, Q.-S., Kirnarskiy, L., Rees, A., and Paul, S. (1997) *J. Mol. Biol.* 271, 374–385
32. Legendre, D., Laraki, N., Graslund, T., Bjornvad, M. E., Bouchet, M., Nygren, P. A., Borchert, T. V., Fastrez, J. (2000) *J. Mol. Biol.* 296, 87–102
33. Wong, L., Wong, L., Radic, Z., Bruggemann, R. I., Hosea, N., Berman, H. A., and Taylor, P. (2000) *Biochemistry* 39, 5750–5757
34. Tramontano, A. (1994) *Appl. Biochem. Biotechnol.* 47, 257–275
35. Zhou, G. W., Guo, J., Huang, W. Fletterick, R. J., and Scanlan, T. S. (1994) *Science* 265, 1059–1064
36. Rahil, J., and Pratt, R. F. (1994) *Biochemistry* 33, 116–25
37. Haux, J. E., Quistad, G. B., and Casida, J. E. (2000) *Chem Res Toxicol* 13, 646–51
38. Pollack, S. J., Hsiun, P., and Schultz, P. G. (1989) *J. Am. Chem. Soc.* 111, 5961–5962
39. Li, L., Sun, M., Gao, Q.-S., and Paul, S. (1996) *Mol. Immunol.* 33, 593–600
40. Paul, S., Volle, D. J., Powell, M. J., and Massey, R. J. (1990) *J. Biol. Chem.* 265, 11910–11913
41. Shuster, A. M., Gololobov, G. V., Kvashuk, O. A., Bogomolova, A. E., Smirnov, I. V., and Gabibov, A. G. (1992) *Science* 256, 665–667
42. Tawfik, D. S., Chap, R., Green, B. S., Sela, M., and Eshhar, Z. (1995) *Proc. Natl. Acad. Sci.* 92, 2145–2149
43. Takahashi, N., Kakinuma, H., Hamada, K., Shimazaki, K., Yamasaki, Y., Matsushita, H., Nishi, Y. (2000) *J Immunol Methods* 235, 113–120

44. Wirsching, P., Ashley, J. A., Lo, C. H., Janda, K. D., Lerner, R. A. (1995) *Science* 270, 1775–82
45. Nossal, G. J. V. (1995) *Annu. Rev. Immunol.* 13, 1–27.

EXAMPLE III

CRTAs: Covalently Reactive Transition State Analogs

The unexpected observation that an example phosphonate monoester (1) expresses covalent reactivity with serine proteases has allowed the design of novel CRTSAs. These compounds are mimics of the transition state by virtue of their tetrehedral character and the negative charge carried on the oxygen atom. At the same time, the phosphorous atom is sufficiently electrophilic to permit covalent binding to active site serine residues. Thus, the CRTSAs combines substrate like covalent reactivity with transition state mimicry. These properties impart greater selectivity to the CRTSAs for serine protease binding. When combined with appropriate flanking peptides, the CRTSAs become specific for individual catalytic antibodies directed against different antigens. The CRTSAs of the invention may be utilized in a variety of applications. These include:

Selection of high turnover, specific catalytic Abs from display libraries

Selective inhibition of pathogenic autoantibodies

Use as immunogens to stimulate the stimulate catalytic antibody formation, followed by screening for covalent CRTSA binding to identify the best catalysts.

CRTSA Structure: See FIGS. 16 and 17.

CRTSAs in which the covalent reactivity and transition state mimicry are properly balanced to permit selective catalyst binding are disclosed. Structural principles underlying CRTSA design are:

The R2 group in 2 is an electron withdrawing group composed, for example, of substituents 3–20 shown in FIG. 16. This increases the covalent nucleophilicity of the phosphorous without compromising the transition state character of 2. 3–20 represent substituents with varying electron withdrawing capacity. The ideal substituent is one that permits selective binding to the active site of the desired catalyst without binding other catalysts that utilize nucleophilic covalent mechanisms. For example, increasing the covalency of the phosphorous to very high levels is undesirable because this permits it to bind enzymes essential to life, such as acetylcholinesterase. Decreases in the covalency of the phosphorous are achieved using 21–37 as the R2 substituent.

R1 is a peptide epitope intended to permit high affinity binding to the desired catalytic antibody. The size of this epitope is usually 5–15 amino acids in length. The sequence of the peptide corresponds to epitopes in any desired target of the antibodies, e.g., beta-amyloid, IgE, Il-8, tumor necrosis factor, gp120, EGFR and plasminogen activating inhibitor-1.

To further increase the specificity of CRTSAs for individual antigen-specific catalysts, R2 is composed of 38–47, which consist of electron withdrawing or electron donating groups extended with a peptide epitope capable of being recognized by the desired catalyst. Insertion of peptide sequences on both sides of the phosphorous center is desirable to increase the specificity of the CRTSA.

Determination of optimal CRTSA structure:

Four criteria are considered when designing the structure of the CRTSA.

Potency of inhibtion of catalytic activity (Ki). The best CRTSA is identified by screening a panel of CRTSA structures for the ability to inhibit non-Ab serine proteases and Ab serine proteases.

Irreversible CRTSA binding to non-Ab serine proteases and Ab serine proteases under denaturing conditions (SDS-electrophoresis; see manuscripts for method)

Ability of CRTSAs to select high turnover, specific catalysts from displayed antibody libraries (see manuscripts for phage display methods; other display methods such as bacterial and yeast display are also suitable).

Immunization of experimental animals with CRTSAs followed by analysis of polyclonal serum antibodies and monoclonal antibodies from the immunized animals for the desired catalytic activity.

FIGS. 16 and 17 depict a series of electron withdrawing or electron donating substituents with or without flanking peptide epitopes at position R.

EGFR Met-Glu-Glu-Asp-Gly-Val-Arg-Lys-Cys (SEQ ID NO: 50)

Cys-Glu-Gly-Pro-Cys-Arg (SEQ ID NO: 51)

HIVgp120 Lys-Gln-Ile-Ile-Asn-Met-Trp-Gln-Gllu-Val-Gly (SEQ ID NO: 52)

Ala-Met-Tyr-Ala (SEQ ID NO: 53)

TNF α Leu-Ala-Asn-Gly-Val-Glu-Leu (SEQ ID NO: 54)

Asp-Asn-Gln-Leu-Val-Val-Pro (SEQ ID NO: 55)

IL-1β Pro-Lys-Lys-Lys-Met-Glu-Lys (SEQ ID NO: 56)

Phe-Val-Phe-Asn-Lys-Ile-Glu (SEQ ID NO: 57)

Compounds I–V depicted in FIG. 18 have several utilities.

1. Neutral diester I and similar compounds for phage Ab selection, inhibition of pathogenic Abs and elicitation of Ab responses in experimental animals in instances where the reaction to be catalyzed involves covalent binding and hydrolysis of bonds linking non-positively charged flanking groups.

2. Neutral diester II and III and similar compounds with weakened covalent reactivity for the same purposes as in 1. above. In these compounds, substitution of one or both of the phenyl groups for methyl groups lowers the electrophilicity of the phosphorous and thereby imparts instability to the covalent bond between the phosphorous and the active site nucleophiles in catalysts.

3. Neutral monoester IV and V for the same purposes as described in 1 above.

In another embodiment of the present invention, R1 and R2 are the peptide epitopes corresponding to peptide determinants in the desired target antigen, and R3 is an electron withdrawing or electron donating group designed to increase and decrease the covalent reactivity of the phosphorus atom. For example, structures 3–20 in FIG. 16 can serve as electron withdrawing groups, and structures 21–37 can serve as electron donating groups. Methods for synthesis of these compounds are well-known in the art. It is possible that placing the electron withdrawing group R3 on the N-terminal side of the phosphonate ester leads to a change in the leaving group upon formation of the phosphonyl-catalyst complex, i.e., liberation of the the N-terminal peptide component instead of the C-terminal component that is customarily liberated. However, for the purposes described in this patent application, this alteration in reaction products is inconsequential, as in both cases, the covalent adduct formation will result in inhibition of antibody catalytic activity, selective binding of catalysts for the purpose of their isolation, and stimulation of B cell clonal selection for the purpose of induction of catalytic antibody synthesis. The structure of this type of CRTSA is shown in FIG. 20.

EXAMPLE IV

Passive Immunization with the Catalytic Antibodies of the Present Invention

There are many areas in medicine where monoclonal antibody administration is providing clinical benefit. In the field of organ transplantation, a MoAb (OKT3) which binds to the T cell receptor has been employed to deplete T cells in vivo. Additionally, MoAbs are being used to treate graft v. host disease with some success. A clinical trial has been established which is assessing the ability of anti-CD4 moAB to deplete a subset of T cells in the treatment of multiple schlerosis. Accordingly, methods of administration of monoclonal antibodies are well known to clinicians of ordinary skill in the art. An exemplary method and dosage schedule are provided in a phase III, randomized, controlled study of chemotherapy alone or in combination with a recombinant moAB to the oncogene HER2.

All patients randomized to the recombinant humanized MoAb Her2 arm of the study will receive treatment as a 4 mg/lkg I.V. loading dose on Day 0 (the first day of the MoAb HER2 infusion, or the day of randomization for patients in the control group), then weekly as a dose of 2 mg/kg I.V. through out the course of the study. All patients will be monitored during each study visit by a clinical assessment, a symptom directed physical examination (if appropriate) and laboratory tests. Routine tumor evaluations will be conducted for all patients at prescribed intervals during the study. All adverse events will be recorded.

The administration of the catalytic antibodies of the present invention will be done as described above for the HER2 monoclonal antibody. As in the HER2 study, following infusion, patients will be assessed to determine the efficacy of the administered catalytic antibody.

Should the catalytic antibodies administered as above give rise to undesirable side effects in the patient, the immunizing CRTSAs will be administered to covalently inhibit the action of the catalytic antibodies.

EXAMPLE V

Active Immunization Using the CRTSAs of the Present Invention

Active immunization will be done using previously developed methods with vaccines designed to elicit protective antibody responses against the desired antigens [82, 83]. For example, the CRTSAs mixed with a suitable adjuvant formulation such as alum can be admimestered intramuscularly at a dose optimized for maximum antibody synthesis (100–1000 µg/kg body weight), and two or three booster injectijns can be administed at 4 week intervals, until the catalytic antibody concentration in the serum reaches plateau levels. The protective immunity so generated is anticipated to last for several years, because vaccination will result in formation of specific, long lived memory cells that can be stimulated to produce antibodies upon exposure to the offending organism or cancer cell. Descriptions and methods to determine the catalytic antibody concentrations are set forth in Examples I and II. Because antibody synthetic response to most antigens are T cell dependent, an appropriate T cell epitope can be incorporated into the immunogen by peptide synthesis. Alternatively, a carrier such as keyhole limpet hemocyanin can be conjugated to the CRTSA via coupling through lys side chain amino groups or Cys side chain sulfahydryl groups to maximize the antibody response if necessary.

While certain of the preferred embodiments of the present invention have been described and specifically exemplified above, it is not intended that the invention be limited to such embodiments. Various modifications may be made thereto without departing from the scope and spirit of the present invention, as set forth in the following claims.

What is claimed is:

1. A covalently reactive transition state antigen analog (CRTSA), comprising the following structural formula:

$$R_1\text{-E-}R_2$$

wherein $R_1$ is a peptide sequence of an epitope of a target protein antigen, E is an electrophilic covalently reactive center bearing a partial or full negative charge and $R_2$ is an electron withdrawing or electron donating substituent, $R_2$ optionally further comprising a flanking peptide sequence, further comprising Y between $R_1$ and E, wherein Y is a positively charged amino acid adjacent to the electrophilic center selected from the group consisting of lysine, arginine or analogs thereof.

2. The CRTSA as claimed in claim 1, wherein said electrophilic reaction center is selected from the group consisting of a phosphonate moiety, a boronate moiety and a vanadate moiety.

3. The CRTSA as claimed in claim 1, wherein Y is an amino acid analog further comprising an electron withdrawing or electron donating substituent.

4. The CRTSA of claim 1 wherein Y is an electron withdrawing substituent selected from the group consisting of structures 3–20 of FIG. 16 and structures 38–47 of FIG. 17.

5. The CRTSA of claim 1 wherein Y is an electron donating substituent selected from the group consisting of structures 21–37 of FIG. 17.

6. The CRTSA as claimed in claim 1, wherein said epitope of a target protein antigen is an epitope present in proteins selected from the group consisting of tumor necrosis factor, epidermal growth factor recepor, interleukin-1, gp120, gp160, gag, pol, hepatitis B surface antigen, bacterial exotoxins, EGF, TGFα, p53, prostate specific antigen, carcinoembryonic antigen, prolactin, human chorionic gonadotropin, c-myc, c-fos, c-jun, epidermal growth factor receptor, HER-2, prolactin receptors, steroid receptors, and IL-4.

7. The CRTSA as claimed in claim 1, said CRTSA elicits catalytic antibody production to epidermal growth factor receptor, wherein $R_1$ is Met-Glu-Glu-Asp-Gly-Val-Arg-Lys-Cys (SEQ ID NO: 50); Y is Lys or an analog thereof; E is a phosphonate monoester; and $R_2$ comprises the flanking sequence Cys-Glu-Gly-Pro-Cys-Arg (SEQ ID NO: 51).

8. The CRTSA as claimed in claim 1, said CRTSA elicits catalytic antibody production to gp120, wherein $R_1$ is Lys-Gln-Ile-Ile-Asn-Met-Trp-Gln-Glu-Val-Gly (SEQ ID NO: 52); Y is Lys or an analog thereof; E is a phosphonate monoester; and $R_2$ comprises the flanking sequence Ala-Met-Tyr-Ala (SEQ ID NO: 53).

9. The CRTSA as claimed in claim 1, said CRTSA elicits catalytic antibody production to TNFα, wherein $R_1$ is Leu-Ala-Asn-Gly-Val-Glu-Leu (SEQ ID NO: 54); Y is Lys or an analog thereof; E is a phosphonate monoester; and $R_2$ comprises the flanking sequence Asp-Asn-Gln-Leu-Val-Val-Pro (SEQ ID NO: 55).

10. The CRTSA as claimed in claim 1, said CRTSA elicits catalytic antibody production to IL-1β, wherein R1 is Pro-Lys-Lys-Lys-Met-Glu-Lys (SEQ ID NO: 56); Y is Lys or an analog thereof; E is a phosphonate monoester; and $R_2$ comprising the sequence Phe-Val-Phe-Asn-Lys-Ile-Glu (SEQ ID NO: 57).

* * * * *